United States Patent
Dam et al.

(10) Patent No.: US 7,838,263 B2
(45) Date of Patent: Nov. 23, 2010

(54) METHODS OF IDENTIFYING A PLANT WITH AN NSF1 LOCUS

(75) Inventors: Thao Dam, Bear, DE (US); Anthony D. Guida, Jr., Newark, DE (US); Christine B. Hazel, Port Deposit, MD (US); Bailin Li, Hockessin, DE (US); Mark E. Williams, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 87 days.

(21) Appl. No.: 11/964,871

(22) Filed: Dec. 27, 2007

(65) Prior Publication Data
US 2008/0096218 A1    Apr. 24, 2008

Related U.S. Application Data

(62) Division of application No. 11/683,737, filed on Mar. 8, 2007, now abandoned.

(60) Provisional application No. 60/780,946, filed on Mar. 9, 2006, provisional application No. 60/888,634, filed on Feb. 7, 2007.

(51) Int. Cl.
*C12Q 1/26*    (2006.01)
*C12Q 1/68*    (2006.01)

(52) U.S. Cl. .............................. 435/25; 435/6

(58) Field of Classification Search .................. None
See application file for complete search history.

(56) References Cited

U.S. PATENT DOCUMENTS

| | | | |
|---|---|---|---|
| 5,639,951 A | 6/1997 | Bosemark et al. | |
| 2004/0034888 A1 | 2/2004 | Liu et al. | |
| 2007/0039067 A1* | 2/2007 | Feldmann et al. | 800/278 |

FOREIGN PATENT DOCUMENTS

| WO | WO 2004/062351 | 7/2004 |
|---|---|---|
| WO | WO 2005/107437 | 11/2005 |

OTHER PUBLICATIONS

Harms, et al., Genetic and biochemical characterization of corn inbred lines tolerant to the sulfonylurea herbicide primisulfuron, Theor Appl Genet, (1990), 80:353-358.

Fonne-Pfister, et al., Hydroxylatiopn of Primisulfuron by an Inducible Cytochrome P450-Dependent Monooxygenase System from Maize, Pesticide Biochemistry and Physiology, (1990), 37:165-173.
Kang, M.S., Inheritance of Susceptibility to Nicosulfuron Herbicide in Maize, Journal of Heredity, (1993) 84(3):216-217.
Green et al., Response of Corn (Zea mays L.) Inbreds and Hybrids to Sulfonylurea Herbicides, Weed Science, (1993), 41:508-516.
Green et al., Response of Maize (Zea mays) Inbreds and Hybrids to Rimsulfuron, Pestic. Sci., (1994) 40:187-191.
Brown et al., Recent Advances in Sulfonylurea Herbicides, Chemistry of Plant Protection, (1994), 10:47-81.
Werck-Reichhart, et al., Cytochromes P450 for engineering herbicide tolerance, Trends in Plant Science, (2000), 5(3):116-123.
Li, et al., Development of PPO inhibitor-resistant cultures and crops, Pest Manag Sci, (2005), 61:277-285.
Williams, et al., Cross-sensitivity in Sweet Corn to Nicosulfuron and Mesotrione Applied Postemergence, Hort Science, (2005), 40(6): 1801-1805.
Matringe, et al., p-Hydroxyphenylpyruvate diosygenase inhibitor-resistant plants, Pest Manag Sci., (2005), 61:269-276.
Pan, et al., Map-based cloning of a novel rice cytochrome P450 gene CYP81A6 that confers resistance to two different classes of herbicides, Plant Mol Biol (2006), 61:933-943.
Pan, et al., Map-based cloning of a novel rice cytochrome P450 gene CYUP81A6 that confers resistance to two different classes of herbicides, NCBI Accession No. ABC69856, (2006).
Zhang, et al., Identification of a cytochrome P450 hydroxylase, CYP81A6, as the candidate for the bentazon and sulfonylurea herbicide resistance gene, Bel, in rice, Mol Breeding (2007), 19:59-68.
Moreno, et al., Chromosomal Location of nsf1 Gene in Maize by Use of B-A Translocations, Maize Genetics and Genomics Database (1999).
Kang, et al., nsf1 nicosulfuron susceptible1 (locus), Maize Genetics and Genomics Database (1999).
Didierjean, et al., Engineering Herbicide Metabolism in Tobacco and Arabidopsis with CYP76B1, a Cytochrome P450 Enzyme from Jerusalem Artichoke, Plant Physiol, (2002), 130: 179-189.

* cited by examiner

*Primary Examiner*—Cathy Kingdon Worley

(57) ABSTRACT

This invention relates to polynucleotide sequences encoding a gene that can confer resistance to at least one herbicide. It further relates to plants and seeds of plants carrying chimeric genes comprising said polynucleotide sequences, which enhance or confer resistance to at least one herbicide, and methods of making said plants and seeds. The invention further presents sequences that can be used as molecular markers that in turn can be used to identify the region of interest in corn lines resulting from new crosses and to quickly and efficiently select the best lines for breeding strategies by avoiding sensitive lines. Methods of identifying a plant with an Nsf1 locus using molecular markers are described.

9 Claims, 7 Drawing Sheets

Figure 1a

Multiple Sequence Alignment Results

```
 Symbol comparison table: blosum62.cmp CompCheck: 1102

GapWeight: 8
           GapLengthWeight: 2

AAK38079_pileup_158748.txt  MSF: 750  Type: P  March 7, 2006 17:35
Check: 2632 ..

XP_469851            SEQ ID NO: 12
XP_469852            SEQ ID NO: 13
aak38080             SEQ ID NO: 5
aak38081             SEQ ID NO: 7
BAD27508             SEQ ID NO: 8
aak38079             SEQ ID NO: 6
BAD27507             SEQ ID NO: 9
BAD27506             SEQ ID NO: 10
rice_nsf_hom         SEQ ID NO: 4
xp_469850            SEQ ID NO: 3
XP_469849            SEQ ID NO: 11
nsf_peptide          SEQ ID NO: 2

//
              1                                                  50
    XP_469851  ~~~~~~~~~~ ~~~~~~~~~~ ~~~~~~~~~~ ~~~~~~~~~~ ~~~~~~~~~~
    XP_469852  ~~~~~~~~~~ ~~~~~~~~~~ ~~~~~~~~~~ ~~~~~~~~~~ ~~~~~~~~~~
     aak38080  ~~~~~~~~~~ ~~~~~~~~~~ ~~~~~~~~~~ ~~~~~~~~~~ ~~~~~~~~~~
     aak38081  ~~~~~~~~~~ ~~~~~~~~~~ ~~~~~~~~~~ ~~~~~~~~~~ ~~~~~~~~~~
     BAD27508  ~~~~~~~~~~ ~~~~~~~~~~ ~~~~~~~~~~ ~~~~~~~~~~ ~~~~~~~~~~
     aak38079  ~~~~~~~~~~ ~~~~~~~~~~ ~~~~~~~~~~ ~~~~~~~~~~ ~~~~~~~~~~
     BAD27507  ~~~~~~~~~~ ~~~~~~~~~~ ~~~~~~~~~~ ~~~~~~~~~~ ~~~~~~~~~~
     BAD27506  ~~~~~~~~~~ ~~~~~~~~~~ ~~~~~~~~~~ ~~~~~~~~~~ ~~~~~~~~~~
 rice_nsf_hom  ~~~~~~~~~~ ~~~~~~~~~~ ~~~~~~~~~~ ~~~~~~~~~~ ~~~~~~~~~~
    xp_469850  maflgwavdi ardsgasssv vltcdgygsa lyfspwdsvp lpataspddg
    XP_469849  ~~~~~~~~~~ ~~~~~~~~~~ ~~~~~~~~~~ ~~~~~~~~~~ ~~~~~~~~~~
  nsf_peptide  ~~~~~~~~~~ ~~~~~~~~~~ ~~~~~~~~~~ ~~~~~~~~~~ ~~~~~~~~~~

51                                                100
    XP_469851  ~~~~~~~~~~ ~~~~~~~~~~ ~~~~~~~~~~ ~~~~~~~~~~ ~~~~~~~~~~
    XP_469852  ~~~~~~~~~~ ~~~~~~~~~~ ~~~~~~~~~~ ~~~~~~~~~~ ~~~~~~~~~~
     aak38080  ~~~~~~~~~~ ~~~~~~~~~~ ~~~~~~~~~~ ~~~~~~~~~~ ~~~~~~~~~~
     aak38081  ~~~~~~~~~~ ~~~~~~~~~~ ~~~~~~~~~~ ~~~~~~~~~~ ~~~~~~~~~~
     BAD27508  ~~~~~~~~~~ ~~~~~~~~~~ ~~~~~~~~~~ ~~~~~~~~~~ ~~~~~~~~~~
     aak38079  ~~~~~~~~~~ ~~~~~~~~~~ ~~~~~~~~~~ ~~~~~~~~~~ ~~~~~~~~~~
     BAD27507  ~~~~~~~~~~ ~~~~~~~~~~ ~~~~~~~~~~ ~~~~~~~~~~ ~~~~~~~~~~
     BAD27506  ~~~~~~~~~~ ~~~~~~~~~~ ~~~~~~~~~~ ~~~~~~~~~~ ~~~~~~~~~~
 rice_nsf_hom  ~~~~~~~~~~ ~~~~~~~~~~ ~~~~~~~~~~ ~~~~~~~~~~ ~~~~~~~~~~
    xp_469850  fllprfpdvc vqrsqftnhl apangtgggg srtgvkeeas evlswppptsk
    XP_469849  ~~~~~~~~~~ ~~~~~~~~~~ ~~~~~~~~~~ ~~~~~~~~~~ ~~~~~~~~~~
  nsf_peptide  ~~~~~~~~~~ ~~~~~~~~~~ ~~~~~~~~~~ ~~~~~~~~~~ ~~~~~~~~~~
```

Figure 1b

```
               101                                                    150
   XP_469851   ~~~~~~~~~~ ~~~~~~~~~~ ~~~~~~~~~~ ~~~~~~~~~~ ~~~~~~~~~~
   XP_469852   ~~~~~~~~~~ ~~~~~~~~~~ ~~~~~~~~~~ ~~~~~~~~~~ ~~~~~~~~~~
     aak38080  ~~~~~~~~~~ ~~~~~~~~~~ ~~~~~~~~~~ ~~~~~~~~~~ ~~~~~~~~~~
     aak38081  ~~~~~~~~~~ ~~~~~~~~~~ ~~~~~~~~~~ ~~~~~~~~~~ ~~~~~~~~~~
     BAD27508  ~~~~~~~~~~ ~~~~~~~~~~ ~~~~~~~~~~ ~~~~~~~~~~ ~~~~~~~~~~
     aak38079  ~~~~~~~~~~ ~~~~~~~~~~ ~~~~~~~~~~ ~~~~~~~~~~ ~~~~~~~~~~
     BAD27507  ~~~~~~~~~~ ~~~~~~~~~~ ~~~~~~~~~~ ~~~~~~~~~~ ~~~~~~~~~~
     BAD27506  ~~~~~~~~~~ ~~~~~~~~~~ ~~~~~~~~~~ ~~~~~~~~~~ ~~~~~~~~~~
 rice_nsf_hom  ~~~~~~~~~~ ~~~~~~~~~~ ~~~~~~~~~~ ~~~~~~~~~~ ~~~~~~~~~~
     xp_469850 qsvrrlevae hwyrlyktdn qrlspdsqqv svlaeshcdl asgnwkeisi
    XP_469849  ~~~~~~~~~~ ~~~~~~~~~~ ~~~~~~~~~~ ~~~~~~~~~~ ~~~~~~~~~~
  nsf_peptide  ~~~~~~~~~~ ~~~~~~~~~~ ~~~~~~~~~~ ~~~~~~~~~~ ~~~~~~~~~~

151                                                    200
   XP_469851   ~~~~~~~~~~ ~~~~~~~~~~ ~~~~~~~~~~ ~~~~~~~~~~ ~~~~~~~~~~
   XP_469852   ~~~~~~~~~~ ~~~~~~~~~~ ~~~~~~~~~~ ~~~~~~~~~~ ~~~~~~~~~~
     aak38080  ~~~~~~~~~~ ~~~~~~~~~~ ~~~~~~~~~~ ~~~~~~~~~~ ~~~~~~~~~~
     aak38081  ~~~~~~~~~~ ~~~~~~~~~~ ~~~~~~~~~~ ~~~~~~~~~~ ~~~~~~~~~~
     BAD27508  ~~~~~~~~~~ ~~~~~~~~~~ ~~~~~~~~~~ ~~~~~~~~~~ ~~~~~~~~~~
     aak38079  ~~~~~~~~~~ ~~~~~~~~~~ ~~~~~~~~~~ ~~~~~~~~~~ ~~~~~~~~~~
     BAD27507  ~~~~~~~~~~ ~~~~~~~~~~ ~~~~~~~~~~ ~~~~~~~~~~ ~~~~~~~~~~
     BAD27506  ~~~~~~~~~~ ~~~~~~~~~~ ~~~~~~~~~~ ~~~~~~~~~~ ~~~~~~~~~~
 rice_nsf_hom  ~~~~~~~~~~ ~~~~~~~~~~ ~~~~~~~~~~ ~~~~~~~~~~ ~~~~~~~~~~
     xp_469850 hhkkmpsstt tktttpsrda wivsarsdpf hllleaqapl gikadalsqi
    XP_469849  ~~~~~~~~~~ ~~~~~~~~~~ ~~~~~~~~~~ ~~~~~~~~~~ ~~~~~~~~~~
  nsf_peptide  ~~~~~~~~~~ ~~~~~~~~~~ ~~~~~~~~~~ ~~~~~~~~~~ ~~~~~~~~~~

201                                                    250
   XP_469851   ~~~~~~~~~~ ~~~~~~~~~~m DKAY.IAvfS iAiLFLLvdY frcrrrrgsg
   XP_469852   ~~~~~~~~~~ ~~~~~~~~~~m vKAY.IAifS iAvLlLi..h fLfrrr...g
     aak38080  ~~~~~~~~~~ ~~~~~~~~~~m DKAY.IAiLS cAfLFLvH.Y vLGk..vsdg
     aak38081  ~~~~~~~~~~ ~~~~~~~~~~m DKAY.IAiLS cAflflvH.Y vLGk..vsdg
     BAD27508  ~~~~~~~~~~ ~~~~~~~~~~m DKAY.IAiLS cAfLFLvH.Y vLGk..vsdg
     aak38079  ~~~~~~~~~~ ~~~~~~~~~~m DKAY.IAiLS sAfLFLvH.Y vLGk..vsdg
     BAD27507  ~~~~~~~~~~ ~~~~~~~~~~m DKAY.IAiLS cAfLFLvH.Y vLgk..vshg
     BAD27506  ~~~~~~~~~~ ~~~~~~~~~~m DKAY.IAiLS cAfLFLvH.Y vLgk..vshg
 rice_nsf_hom  ~~~~~~~~~~ ~~~~~~~~~~m DnAYiIAiLS vAiLFLLHyY LLgr..gngg
     xp_469850 aavhqshrnt shirelslam DnAYiIAiLS vAiLFLLHyy LLgr..gngg
    XP_469849  ~~~~~~~~~~ ~~~~~~~~~~m DKAY.IAvfS iviLFLLvdY Lrrl..rggg
  nsf_peptide  ~~~~~~~~~~ ~~~~~~~~~~M DKAY.IAALS AAALFLLH.Y LLGRRAGGEG 251                                                    300
   XP_469851   snngenkgml qLPPSPPAIP FfGHLHLidk PlHaALsRLA eRHGPVFSlR
   XP_469852   rsng.....m pLPPSPPAIP FfGHLHLidk PfHaALsRLA eRHGPVFSlR
     aak38080  .rrgK.kgav qLPPSPPAvP FLGHLHLvdk PiHatmcRLA ARlGPVFSlR
     aak38081  .rrgK.kgav qLPPSPPAvP FLGHLHLvdk PiHatmcRLA ARlGPVFSlR
     BAD27508  .rrgK.kgav qLPPSPPAIP FiGHLHLvek PiHatmcRLA ARlGPVFSlR
     aak38079  .rrgK.kgav qLPPSPPAvP FLGHLHLvek PiHatmcRLA ARlGPVFSlR
     BAD27507  .rrgK.kgav qLPPSPPAIP FiGHLHLvek PiHatmcRLA ARlGPVFSlR
     BAD27506  .rrgK.kgav qLPPSPPAIP FiGHLHLvek PiHatmcRLA ARlGPVFSlR
 rice_nsf_hom  aA........ RLPPgPPAvP ilGHLHLVKk PmHatmsRLA eRyGPVFSlR
     xp_469850 aA........ RLPPgPPAvP ilGHLHLVKk PmHatmsRLA eRyGPVFSlR
    XP_469849  tsngK.nkgm RLPPglPAvP iiGHLHLVKk PmHatLsRLA ARHGPVFSlR
  nsf_peptide  KAKAK.GSRR RLPPSPPAIP FLGHLHLVKA PFHGALARLA ARHGPVFSMR
```

Figure 1c

```
              301                                                                    350
   XP_469851  LGsRnAVVVS  SPeCARECFT  dnDVcFANRP  qFPSqmpAtF  ygAgfgfanY
   XP_469852  LGsRnAVVVS  SPeCARECFT  dnDVcFANRP  rFPSqmLAtF  nGtsLgsanY
     aak38080 LGsRRAVVVS  SseCARECFT  EHDVtFANRP  kFPSqlLvSF  nGtaLvtSSY
     aak38081 LGsRRAVVVS  SseCARECFT  EHDVtFANRP  kFPSqlLvSF  nGtaLvtSSY
     BAD27508 LGsRRAVVVp  SseCARECFT  EHDVtFANRP  kFPSqlLASF  nGtaLvtSSY
     aak38079 LGsRRAVVVS  SseCARECFT  EHDVtFANRP  kFPSqlLvSF  nGtaLvtSSY
     BAD27507 LGsRRAVVVS  SseCARECFT  EHDVtFANRP  ssrrklLASF  nGtaLvtSSY
     BAD27506 LGsRRAVVVS  SseCARECFT  EHDVtFANRP  kFPSqlLASF  nGtaLvtpSY
 rice_nsf_hom LGsRRAVVVS  SPgCARECFT  EHDVtFANRP  rFeSqlLvSF  nGAaLataSY
    xp_469850 LGsRRAVVVS  SPgCARECFT  EHDVtFANRP  rFeSqlLvSF  nGAaLataSY
   XP_469849  LGsRRAVVVS  SPgCARECFT  EHDVaFANRP  rFeSqlLmSF  DGtaLamaSY
  nsf_peptide LGTRRAVVVS  SPDCARECFT  EHDVNFANRP  LFPSMRLASF  DGAMLSVSSY 351                                                                    400
   XP_469851  GahWRNLRRi  AtVhLLSAhR  VrgMAgvvsg  eiRpMVqRMy  RAAAAagvGV
   XP_469852  GPhWRNLRRi  AtVhLLSshR  VsgMsgiIsg  QaRhMVRRMy  RAAtAsaaGV
     aak38080 GPhWRNLRRV  AtVQLLSAhR  VaCMsgvIaA  eVRAMaRRlf  hAteAspdGa
     aak38081 GPhWRNLRRV  AtVQLLSAhR  VaCMsgvIaA  eVRAMaRRlf  hAAeAspdGa
     BAD27508 GPhWRNLRRV  AtVQLLSAhR  VaCMsgvIaA  eVRAMaRRlf  hAAeAspdGa
     aak38079 GPhWRNLRRV  AtVQLLSAhR  VtCMsgvIaA  eVRAMaRRlf  hAAeAspdGa
     BAD27507 GPhWRNLRRV  AtVQLLSAhR  VaCMsgvIaA  eVRAMaRRlf  hAAeAspdGa
     BAD27506 GPhWRNLRRV  AtVQLLSAhR  VaCMsgvIaA  eVRAMaRRlf  hAAeAspgGa
 rice_nsf_hom GahWRNLRRi  vAVQLLSAhR  VGlMsglIag  eVRAMVRRMy  RAAAAspaGa
    xp_469850 GahWRNLRRi  vAVQLLSAhR  VGlMsglIag  eVRAMVRRMy  RAAAAspaGa
   XP_469849  GPhWRNLRRV  AAVQLLSArR  VGlMsglIag  eVRAMVRslc  R....rpaaa
  nsf_peptide GPYWRNLRRV  AAVQLLSAHR  VGCMAPAIEA  QVRAMVRRMD  RAAAAGGGGV 401                                                                    450
   XP_469851  ARVQLKRRLF  ELSLSVLMEa  IAqTKttRpE  adDADtDMSv  EAqEFKnvlD
   XP_469852  ARVQLnRRLF  ELSLSVLMEa  IAqsKTtRrE  apDADtDMSm  EAqElrhvlD
     aak38080 ARVQLKRRLF  ELSLSVLMET  IAqTKatRsE  .ADADtDMSv  EAqEFKevVD
     aak38081 ARVQLKRRLF  ELSLSVLMET  IAqTKatRsE  .ADADtDMSv  EAqEFKevVD
     BAD27508 ARVQLKRRLF  ELSLSVLMET  IAqTKatRsE  .ADADtDMSv  EAqEFKevVD
     aak38079 ARVQLKRRLF  ELSLSVLMET  IAqTKatRsE  .ADADtDMSl  EAqEFKevVD
     BAD27507 tRVQLKRRLF  ELSLSVLMET  IAqTKatRsE  .ADADtDMSv  EAqEFKevVD
     BAD27506 ARVQLKRgpF  ELSLSVLMET  IAqTKatRsE  .aDADtDMSv  EAqEFKevVD
 rice_nsf_hom ARiQLKRRLF  EvSLSVLMET  IAHTKatRpE  .tDpDtDMSv  EAqEFKQvVD
    xp_469850 ARiQLKRRLF  EvSLSVLMET  IAHTKatRpE  .tDpDtDMSv  EAqEFKQvVD
   XP_469849  ApVQLKRRLF  ELSLSVLMET  IAqsKatRpE  ttDtDtDMSm  EAqEyKQvVe
  nsf_peptide ARVQLKRRLF  ELSLSVLMET  IAHTKTSRAE  .ADADSDMST  EAHEFKQIVD 451                                                                    500
   XP_469851  ELnPllGaAN  lWDYLPaLRv  FDVlGVkrKI  atlanRRDAF  vrRLIDaERq
   XP_469852  ELnPlIGaAN  lWDYLPaLRW  FDVFGVkrKI  vaAVnRRnAF  mrRLIDaERq
     aak38080 kLiPhlGaAN  mWDYLPVmRW  FDVFGVRNKI  LhAVSRRDAF  LrRLIDaERR
     aak38081 kLiPhlGaAN  mWDYLPVmRW  FDVFGVRNKI  LhAVSRRDAF  LrRLIDaERR
     BAD27508 kLiPhlGaAN  mWDYLPVmRW  FDVFGVRNKI  LhAVSRRDAF  LrRLIDaERR
     aak38079 kLiPhlGaAN  mWDYLPVmRW  FDVFGVRsKI  LhAVSRRDAF  LrRLInaERR
     BAD27507 kLiPhlGaAN  mWDYLPVmRW  FDVFGVRNKI  LhAVSRRDAF  LrRLIDaERR
     BAD27506 kpiPhlGaAN  mWDYLPVmRW  FDVFGVRNKI  LhAVSRRDAF  LrRLIDaERR
 rice_nsf_hom EiiPhIGaAN  lWDYLPaLRW  FDVFGVRrKI  LaAVSRRDAF  LrRLIDaERR
    xp_469850 EiiPhIGaAN  lWDYLPaLRW  FDVFGVRrKI  LaAVSRRDAF  LrRLIDaERR
   XP_469849  EilerIGTgN  lcDYLPaLRW  FDVFGVRNrI  LaAVSRRDAF  LrRLIyaaRw
  nsf_peptide ELVPYIGTAN  RWDYLPVLRW  FDVFGVRNKI  LDAVGRRDAF  LGRLIDGERR
```

Figure 1d

```
                501                                                           550
  XP_469851  Rmdng.vDgG  DdgEkKSvIs  VLLsLQKtEP  EVYkDivIvn  LCAaLFaAGT
  XP_469852  RmdnndvDgG  DdgEkKSMIs  VLLTLQKtqP  EVYTdTlImt  LCApLFGAGT
    aak38080 RL....aDgG  sdgdkKSMIA  VLLTLQKtEP  kVYTDTmITA  LCANLFGAGT
    aak38081 RL....aDgG  sdgdkKSMIA  VLLTLQKtEP  kVYTDTmITA  LCANLFGAGT
    BAD27508 RL....aDgG  sdgdkKSMIA  VLLTLQKtEP  kVYTDTmITA  LCANLFGAGT
    aak38079 RL....aDgG  sdgdkKSMIA  VLLTLQKtEP  kVYTDTmITA  LCANLFGAGT
    BAD27507 RL....aDgG  sdgdkKSMIA  VLLTLQKtEP  kVYTDTmITA  LCANLFGAGT
    BAD27506 RL....aDgG  sdgdkKSMIA  VLLTLQKtEP  kVYTDTmITA  LCANLFGAGT
rice_nsf_hom RL.....DdG  DEgEkKSMIA  VLLTLQKtEP  EVYTDnmITA  LtANLFGAGT
   xp_469850 RL.....DdG  DEgEkKSMIA  VLLTLQKtEP  eVYTDnmITA  LtANLFGAGT
  XP_469849  Rm......Dd. ..gEkKSMIA  VLLTLQKtqP  EVYTDnmITA  LCsNLlGAGT
 nsf_peptide RL.....DAG  DESESKSMIA  VLLTLQKSEP  EVYTDTVITA  LCANLFGAGT 551                                                           600
  XP_469851  ETTamTiEWA  MSLLLNHpki  LKKAkAEIDA  sVGnSRLing  DDmPHLsYLQ
  XP_469852  ETTSTTiEWA  MSLLLNHpEi  LKKAQAEIDm  sVGnSRLisv  vDVhrLgYLQ
    aak38080 ETTSTTTEWA  MSLLLNHpaA  LKKAQAEIDA  sVGTSRLVsv  DDVPsLaYLQ
    aak38081 ETTSTTTEWA  MSLLLNHpaA  LKKAQAEIDA  sVGTSRLVsv  DDVPsLaYLQ
    BAD27508 ETTSTTTEWA  MSLLLNHpaA  LKKAQAEIDA  sVGTSRLVsv  DDVPsLaYLQ
    aak38079 ETTSTTTEWA  MSLLLNHpaA  LKKAQAEIDA  sVGTSRLVsv  DDVPsLaYLQ
    BAD27507 ETTSTTTEWA  MSLLLNHpaA  LKKAQAEIDA  sVGTSRLVsv  DDVlsLaYLQ
    BAD27506 ETTSTTTErA  MSLLLNHpaA  LKKAQAEIDA  sVGTSRLVsv  DDmPsLaYLQ
rice_nsf_hom ETTSTTsEWA  MSLLLNHpdt  LKKAQAEIDA  sVGnSRLiTA  DDVtrLgYLQ
   xp_469850 ETTSTTsEWA  MSLLLNHpdt  LKKAQAEIDA  sVGnSRLiTA  DDVtrLgYLQ
  XP_469849  ETTSTTiEWA  MSLLLNHpEt  LKKAQAEIDA  sVGnSRLiTA  DDVPriTYLQ
 nsf_peptide ETTSTTTEWA  MSLLLNHREA  LKKAQAEIDA  AVGTSRLVTA  DDVPHLTYLQ 601                                                           650
  XP_469851  CIinETLRLy  PvAPLLiPHE  SsADCkVnGY  hiPsGTMLLV  NViAiqRDPm
  XP_469852  CIinETLRmy  PAAPLLLPHE  SsADCkVGGY  hiPsGaMLLV  NVaAiqRDPv
    aak38080 CIVsETLRLy  PAAPLLLPHE  SsADCkVGGY  nVPadTMLiV  NayAiHRDPA
    aak38081 CIVnETLRLy  PAAPLLLPHE  SsADCkVGGY  nVPadTMLiV  NayAiHRDPA
    BAD27508 CIVnETLRLy  PAAPLLLPHE  SsADCkVGGY  nVPadTMLiV  NayAiHRDPA
    aak38079 CIVsETLRLy  PAAPLLLPHE  SsADCkVGGY  nVPadTMLiV  NayAiHRDPA
    BAD27507 CIVsETLRLy  PAAPLLLPHE  SsADCkVGGY  nVPadTMLiV  NayAiHRDPA
    BAD27506 CIVnETLRLy  PAAPLLLPHE  SsADCkVGGY  nVPadTMLiV  NayAiHRDPA
rice_nsf_hom CIVrETLRLy  PAAPmLLPHE  SsADCkVGGY  niPRGsMLLi  NayAiHRDPA
   xp_469850 CIVrETLRLy  PAAPmLLPHE  SsADCkVGGY  niPRGsMLLi  NayAiHRDPA
  XP_469849  CIVrETLRLy  PAAPmLiPHE  SsADCeVGGY  sVPRGTMLLV  NayAiHRDPA
 nsf_peptide CIVDETLRLH  PAAPLLLPHE  SAADCTVGGY  DVPRGTMLLV  NVHAVHRDPA 651                                                           700
  XP_469851  VWkePneFkP  ERFE...nGes EGlfmiPFGM  GRRKCPGETm  ALqTiGLVLg
  XP_469852  iWkePseFkP  ERFE...nGrf EGlfmiPFGM  GRRrCPGEmL  ALqTiGLVLg
    aak38080 aWEdPleFrP  ERFE...dGKA EGlfmiPFGM  GRRrCPGETL  ALRTiGmVLA
    aak38081 aWEhPlvFrP  ERFE...dGKA EGlfmiPFGM  GRRrCPGETL  ALRTiGmVLA
    BAD27508 aWEhPleFrP  ERFE...dGKA EGlfmiPFGv  GRRrCPGETL  ALRTismVLA
    aak38079 aWEdPleFkP  ERFE...dGKA EGlfmiPFGM  GRRrCPGETL  ALRTiGmVLA
    BAD27507 aWEhPleFrP  ERFE...dGKA EGlfmiPFGM  GRRrCPGETL  ALRTiGmVLA
    BAD27506 aWEhPleFrP  ERFE...dGKA EGlfmiPFGM  GRRrCPGETL  ALRTiGmVLA
rice_nsf_hom VWEePekFmP  ERFE...dGgc dGnLLMPFGM  GRRrCPGETL  ALRTVGLVLg
   xp_469850 VWEePekFmP  ERFE...dGgc dGnLLMPFGM  GRRrCPGETL  ALRTVGLVLg
  XP_469849  aWEePeRFVP  ERFE...GGgc dGnLsMPFGM  GRRrCPGETL  ALhTVGLVLg
 nsf_peptide VWEDPDRFVP  ERFEGAGGKA  EGRLLMPFGM  GRRKCPGETL  ALRTVGLVLA
```

Figure 1e

```
                    701                                                            750
   XP_469851  aLiQCFDWDr  VDGAeVDMtq  gsGLTnPRAV  PLEAMCkPRe  AMsdVfReLl
   XP_469852  TmiQCFDWgr  VDdAmVDMtq  SnGLTslkvi  PLEAMCkPRe  AMcdVLRkfm
      aak38080  TLvQCFDWep  VDGvkVDMte  gGGfTiPkAV  PLEAvCRPRa  vMRdVLqnL~
      aak38081  TLvQCFDWep  VDGvnVDMte  gGGfTiPkAV  PLEAvCRPRa  vMRdVLqsi~
      BAD27508  TLvQCFDWep  VDGvkVDMte  gGGfTiPkAV  PLEAvCRPRa  vMRdVLqnL~
      aak38079  TLvQCFDWep  VDGvkVDMte  gGGfTiPkAV  PLEAvCRPRv  vMRdVLqnL~
      BAD27507  TLvQCFDWep  VDGvkVDMte  gGGfTiPkAV  PLEAvCRPRt  vMRdVLqnL~
      BAD27506  TLvQCFDWep  VDGvkVDMte  gGGfTiPkAV  PLEAvCRPRa  vMRdVLqnL~
  rice_nsf_hom  TLiQCFDWer  VDGveVDMte  gGGLTiPkvV  PLEAMCRPRd  AMgGVLReLv
     xp_469850  TLiQCFDWer  VDGveVDMte  gGGLTiPkvV  PLEAMCRPRd  AMgGVLReLv
     XP_469849  TLiQCFDWer  VDGveVDMae  gGGLTMPkvV  PLEAvCRPRd  AMgGVLReL~
   nsf_peptide  TLLQCFDWDT  VDGAQVDMKA  SGGLTMPRAV  PLEAMCRPRT  AMRGVLKRL~
```

Figure 2a

Multiple Sequence Alignment Results

```
Symbol comparison table: blosum62.cmp CompCheck: 1102

GapWeight: 8
        GapLengthWeight: 2

F2_peptide = SEQ ID NO: 22
nsf_peptide = SEQ ID NO: 2
BMS_peptide = SEQ ID NO: 20
Q66_Peptide = SEQ ID NO: 18
GA209_Peptid = SEQ ID NO: 24
W703A_Peptid = SEQ ID NO: 26

1                                                        50
  F2_peptide MDKAYIAALS AAALFLLHYL LGRRAGGEGK AKAKGSRRRL PPSPPAIPFL
 nsf_peptide MDKAYIAALS AAALFLLHYL LGRRAGGEGK AKAKGSRRRL PPSPPAIPFL
 BMS_peptide MDKAYIAALS AAALFLLHYL LGRRAGGEGK AKAKGSRRRL PPSPPAIPFL
 Q66_Peptide MDKAYIAALS AAALFLLHYL LGRRAGGEGK AKAKGSRRRL PPSPPAIPFL
GA209_Peptid MDKAYIAALS AAALFLLHYL LGRRAGVEG. .KAKGSRRRL PPSPPAIPFL
W703A_Peptid MDKAYIAALS AAALFLLHYL LGRRAGVEG. .KAKSSRRRL PPSPPAIPFL 51                                                       100
  F2_peptide GHLHLVKAPF HGALARLAAR HGPVFSMRLG TRRAVVVSSP DCARECFTEH
 nsf_peptide GHLHLVKAPF HGALARLAAR HGPVFSMRLG TRRAVVVSSP DCARECFTEH
 BMS_peptide GHLHLVKAPF HGALARLAAR HGPVFSMRLG TRRAVVVSSP DCARECFTEH
 Q66_Peptide GHLHLVKAPF HGALARLAAR HGPVFSMRLG TRRAVVVSSP DCARECFTEH
GA209_Peptid GHLHLVKAPF HGALARLAAR HGPVFSMRLG TRRAVVVSSP DCARECFTEH
W703A_Peptid GHLHLVKAPF HAALARLAAR HGPVFSMRLG TRRAVVVSSP DCARECFTEH 101                                                       150
  F2_peptide DVNFANRPLF PSMRLASFDG AMLSVSSYGP YWRNLRRVAA VQLLSAHRVG
 nsf_peptide DVNFANRPLF PSMRLASFDG AMLSVSSYGP YWRNLRRVAA VQLLSAHRVG
 BMS_peptide DVNFANRPLF PSMRLASFDG AMLSVSSYGP YWRNLRRVAA VQLLSAHRVG
 Q66_Peptide DVNFANRPLF PSMRLASFDG AMLSVSSYGP YWRNLRRVAA VQLLSAHRVG
GA209_Peptid DVNFANRPLF PSMRLASFDG AMLSVSSYGP YWRNLRRVAA VQLLSAHRVG
W703A_Peptid DVNFANRPLF PSMRLASFDG AMLSVSSYGP YWRNLRRVAA VQLLSAHRVA 151                                                       200
  F2_peptide CMAPAIEAQV RAMVRRMDRA AAAGGGGVAR VQLKRRLFEL SLSVLMETIA
 nsf_peptide CMAPAIEAQV RAMVRRMDRA AAAGGGGVAR VQLKRRLFEL SLSVLMETIA
 BMS_peptide CMAPAIEAQV RAMVRRMDRA AAAGGGGVAR VQLKRRLFEL SLSVLMETIA
 Q66_Peptide CMAPAIEAQV RAMVRRMDRA AAAGGGGVAR VQLKRRLFEL SLSVLMETIA
GA209_Peptid CMAPAIEAQV RAMVRRMDRA AAAGGGGVAR VQLKRRLFEL SLSVLMETIA
W703A_Peptid CMVPAIEAQV RAMVRRMDRA AAAGGARRAR PAQAAAVRAL PQRAHGNHRA 201                                                       250
  F2_peptide HTKTSRAEAD ADSDMSTEA. HEFKQIVDEL VPYIGTANRW DYLPVLRWFD
 nsf_peptide HTKTSRAEAD ADSDMSTEA. HEFKQIVDEL VPYIGTANRW DYLPVLRWFD
 BMS_peptide HTKTSRAEAD ADSDMSTEA. HEFKQIVDEL VPYIGTANRW DYLPVLRWFD
 Q66_Peptide HTKTSRAEAD A[N]SDMSTEA. HEFKQI[N]EL VPYIGTANRW DYLPVLRWFD
GA209_Peptid HTKTSRAEAD ANSDMSTEA. HEFKQIVNEL VPYIGTANCW DYLPVLRWFD
W703A_Peptid HQDVPRQLEX VDRGPRVQAX RQRARAVHRR GQPLG..... ..LPAGAAL.
```

Figure 2b

```
                   251                                                                    300
  F2_peptide       VFGVRNKILD AVG[T]RDAFLG RLIDGERRR. .LDAGDESES KSMIAVLLTL
 nsf_peptide       VFGVRNKILD AVGRRDAFLG RLIDGERRR. .LDAGDESES KSMIAVLLTL
 BMS_peptide       VFGVRNKILD AVGRR.AFLG RLIDGERRR. .LDAGDESES KSMIAVLLTL
  Q66_Peptide      VFGVRNKILD AVGRRDAFLG RLIDGERRR. .LDAGDESES KSMIAVLLTL
GA209_Peptid       VFGVRNKILD AVGRRDAFLG RLIDGERRR. .LDAGDESES KSMIAVLLTL
W703A_Peptid       VRRVRREEQD P..RRRGQKG RVPEAAHRRG AAEAGRWRRQ RK~~~~~~~~

301                                                                    350
  F2_peptide       QKSEPEVYTD TVITALCANL FGAGTETTST TTEWAMSLLL NHREALKKAQ
 nsf_peptide       QKSEPEVYTD TVITALCANL FGAGTETTST TTEWAMSLLL NHREALKKAQ
 BMS_peptide       QKSEPEVYTD TVITALCANL FGAGTETTST TTEWAMSLLL NHREALKKAQ
  Q66_Peptide      QKSEPEVYTD TVITALCANL FGAGTETTST TTEWAMSLLL NHREALKKAQ
GA209_Peptid       QKSEPEVYTD TVITALLATL SARARTTVAR DVENARG..V ENRKI~~~~~
W703A_Peptid       ~~~~~~~~~~ ~~~~~~~~~~ ~~~~~~~~~~ ~~~~~~~~~~ ~~~~~~~~~~

351                                                                    400
  F2_peptide       AEIDAAVGTS RLVTADDVPH LTYLQCIVDE TLRLHPAAPL LLPHESAADC
 nsf_peptide       AEIDAAVGTS RLVTADDVPH LTYLQCIVDE TLRLHPAAPL LLPHESAADC
 BMS_peptide       AEIDAAVGTS RLVTADDVPH LTYLQCIVDE TLRLHPAAPL LLPHESAADC
  Q66_Peptide      AEIDAAVG[A]S RLVTADDVPH LTYLQCIVDE TLRLHPAAPL LLPHESAADC
GA209_Peptid       ~~~~~~~~~~ ~~~~~~~~~~ ~~~~~~~~~~ ~~~~~~~~~~ ~~~~~~~~~~
W703A_Peptid       ~~~~~~~~~~ ~~~~~~~~~~ ~~~~~~~~~~ ~~~~~~~~~~ ~~~~~~~~~~

401                                                                    450
  F2_peptide       TVGGYDVPRG TMLLVNVHAV HRDPAVWEDP DRFVPERFEG AGGKAEGRLL
 nsf_peptide       TVGGYDVPRG TMLLVNVHAV HRDPAVWEDP DRFVPERFEG AGGKAEGRLL
 BMS_peptide       TVGGYDVPRG TMLLVNVHAV HRDPAVWEDP DRFVPERFEG AGGKAEGRLL
  Q66_Peptide      TVGGYDVPRG TMLLVNVHAV HRDPAVWEDP DRFVPERFEG AGGKAEGRLL
GA209_Peptid       ~~~~~~~~~~ ~~~~~~~~~~ ~~~~~~~~~~ ~~~~~~~~~~ ~~~~~~~~~~
W703A_Peptid       ~~~~~~~~~~ ~~~~~~~~~~ ~~~~~~~~~~ ~~~~~~~~~~ ~~~~~~~~~~

451                                                                    500
  F2_peptide       MP[FGMGRRKC PG]ETLALRTV GLVLATLLQC FDWDTVDGAQ VDMKASGGLT
 nsf_peptide       MP[FGMGRRKC PG]ETLALRTV GLVLATLLQC FDWDTVDGAQ VDMKASGGLT
 BMS_peptide       MP[FGMGRRKC PG]ETLALRTV GLVLATLLQC FDWDTVDGAQ VDMKASGGLT
  Q66_Peptide      MP[FGMGRRKC PG]ETLALRTV GLVLATLLQC FDWDTVDGAQ VDMKASGGLT
GA209_Peptid       ~~~~~~~~~~ ~~~~~~~~~~ ~~~~~~~~~~ ~~~~~~~~~~ ~~~~~~~~~~
W703A_Peptid       ~~~~~~~~~~ ~~~~~~~~~~ ~~~~~~~~~~ ~~~~~~~~~~ ~~~~~~~~~~

501              524
  F2_peptide       MPRAVPLEAM CRPRTAMRGV LKRL
 nsf_peptide       MPRAVPLEAM CRPRTAMRGV LKRL
 BMS_peptide       MPRAVPLEAM CRPRTAMRGV LKRL
  Q66_Peptide      MPRAVPLEAM CRPRTAMRGV LKRL
GA209_Peptid       ~~~~~~~~~~ ~~~~~~~~~~ ~~~~
W703A_Peptid       ~~~~~~~~~~ ~~~~~~~~~~ ~~~~
```

METHODS OF IDENTIFYING A PLANT WITH AN NSF1 LOCUS

CROSS-REFERENCE TO RELATED APPLICATIONS

This application is a divisional application of U.S. Utility application Ser. No. 11/683,737, filed Mar. 8, 2007, which claims the benefit of U.S. Provisional Application Ser. No. 60/780,946, filed Mar. 9, 2006 and U.S. Provisional Application Ser. No. 60/888,634 filed Feb. 7, 2007, the contents of which are herein incorporated by reference in their entirety.

FIELD OF THE INVENTION

This invention relates to compositions and methods useful in creating or enhancing herbicide resistance in plants. Additionally, the invention relates to plants that have been genetically transformed with the compositions of the invention.

BACKGROUND OF THE INVENTION

In the commercial production of crops, it is desirable to easily and quickly eliminate unwanted plants (i.e., "weeds") from a field of crop plants. An ideal treatment would be one which could be applied to an entire field but which would eliminate only the unwanted plants while leaving the crop plants unharmed. One such treatment system involves the use of crop plants that are tolerant to a herbicide. When the herbicide is sprayed on a field of herbicide-tolerant crop plants, the crop plants continue to thrive while non-herbicide-tolerant weeds are killed or severely damaged.

Crop tolerance to specific herbicides can be conferred by engineering genes into crops which encode appropriate herbicide metabolizing enzymes. In some cases these enzymes, and the nucleic acids that encode them, originate in a plant. In other cases, they are derived from other organisms, such as microbes. See, e.g., Padgette et al. (1996) "New weed control opportunities: Development of soybeans with a Round UP Ready™ gene" and Vasil (1996) "Phosphinothricin-resistant crops," both in *Herbicide-Resistant Crops*, ed. Duke (CRC Press, Boca Raton, Fla.) pp. 54-84 and pp. 85-91. Indeed, transgenic plants have been engineered to express a variety of herbicide tolerance genes from a variety of organisms, including a gene encoding a chimeric protein of rat cytochrome P4507A1 and yeast NADPH-cytochrome P450 oxidoreductase (Shiota et al. (1994) *Plant Physiol.* 106: 17), among other plant P450 genes (see, for example, Didierjean, L. et al. (2002) *Plant Physiol.* 130: 179-189; Morant, M. S. et al. (2003) *Opinion in Biotechnology* 14:151-162). Other genes that confer tolerance to herbicides include: acetohydroxy acid synthase ("AHAS"), which has been found to confer resistance to multiple types of ALS herbicides on plants expressing it and has been introduced into a variety of plants (see, e.g., Hattori et al. (1995) *Mol. Gen. Genet.* 246: 419); glutathione reductase and superoxide dismutase (Aono et al. (1995) *Plant Cell Physiol.* 36: 1687); and genes for various phosphotransferases (Datta et al. (1992) *Plant Mol. Biol.* 20: 619).

While herbicide-tolerant crop plants are presently commercially available, improvements in every aspect of crop production are continuously in demand. Herbicides and crops that are presently commercially available unfortunately have particular characteristics which can limit their usefulness in commercial crop production. Particularly, individual herbicides have different and incomplete spectra of activity against common weed species.

The acetolactate synthase, or ALS (also known as AHAS) family of herbicides control weeds by inhibiting the production of branch chain of amino acids that are essential to plant growth and development. Specifically, they bind to the plant ALS enzyme. Commonly used herbicides in this family include nicosulfuron, rimsulfuron, and chlorsulfuron, among others. Herbicides in this category can be quite crop-specific. Embodiments of the invention relate to plants that are resistant to members of the ALS-inhibiting class of herbicides, which encompasses 5 sub-classes of herbicides including, but not limited to, the sulfonylurea (SU) family of herbicides and the imidazolinone family of herbicides.

The pigment synthesis-inhibiting class of herbicides targets the enzymes that allow plants to synthesize pigments, such as carotenoid pigments or chlorophyll pigments. Loss of pigment results in photo-destruction of chlorophyll and whitening of plant tissues, which is why these herbicides are often called "bleaching" herbicides. An example of a sub-class of the bleaching herbicides is the HPPD-inhibiting class, which inhibits the 4-hydroxyphenylpyruvate dioxygenase (HPPD) enzyme (Lee et al. (1997) *Weed Sci.* 45:601-609). Herbicides in this family include, but are not limited to, mesotrione, tembotrione, topramezone and sulcotrione, among others. Corn is generally tolerant to mesotrione due to metabolism of the herbicide (Mitchell et al. (2001) *Pest Mgt. Sci.* 57:120-128). The same detoxification system may give tolerance to both mesotrione and some SU herbicides (Green & Williams (2004) *Proceedings Weed Science Society of America* 44:13). Embodiments of the invention relate to plants that are resistant to members of the pigment synthesis-inhibiting class of herbicides.

The protoporphyrinogen oxidase (PPO)-inhibiting class of herbicides interferes with the synthesis of chlorophyll, resulting in compounds that produce highly active compounds (free-radicals). These reactive compounds disrupt cell membranes which results in the leaf burning associated with post-emergence applications of these products. Herbicides in this family include, but are not limited to, acifluorfen, fomesafen, lactofen, sulfentrazone, carfentrazone, flumiclorac and flumioxazin, among others. Embodiments of the invention relate to plants that are resistant to members of the PPO-inhibiting class of herbicides.

Photosystem II (PSII)-inhibiting herbicides have a mode of action that involves interaction with components in the electron transfer chain of Photosystem II. Photosynthesis requires the transfer of electrons from Photosystem II to Photosystem I. A key step in this electron transfer chain is the reduction of plastoquinone (PQ) by the $D_1$ protein in the thylakoid membrane. PSII-inhibitor herbicides bind to the $D_1$ protein, thus inhibiting PQ binding and interrupting the electron transfer process. This results in the plants not being able to fix carbon dioxide and produce the carbohydrates needed for the plant to survive. The block in electron transfer also causes an oxidative stress and the generation of radicals which cause rapid cellular damage. PSII-inhibiting herbicides are represented by several herbicide families, including the symmetrical triazines, triazinones (asymmetrical triazines), substituted ureas, uracils, pyridazinones, phenyl carbamates, nitriles, benzothiadiazoles, phenyl pyridazines, and acid amides. Embodiments of the invention relate to plants that are resistant to members of the PS II-inhibiting class of herbicides.

Synthetic auxin herbicides are a widely used class of herbicides that mimic the natural auxin hormones produced by plants. Auxins regulate many plant processes, including cell growth and differentiation. Auxins are generally present at low concentrations in the plant. Synthetic auxin herbicides mimic natural auxins and cause relatively high concentrations in the cell that result in a rapid growth response. Susceptible plants treated with these herbicides exhibit symptoms that could be called 'auxin overdose', and eventually die as a result of increased rates of disorganized and uncontrolled growth. Embodiments of the invention relate to plants that are resistant to members of the synthetic auxin class of herbicides.

Some embodiments of this invention are based on the fine mapping, cloning and characterization of the gene responsible for an important herbicide resistance mechanism in maize.

It has been known since the early 1990s that natural tolerance in maize (Zea mays L.) to a subset of sulfonylurea herbicides (nicosulfuron [Dupont Accent® herbicide], rimsulfuron, primisulfuron, and thifensulfuron) is controlled by a single gene (named nsf by Kang (1993) *Journal of Heredity* 84(3): 216-217), with resistance dominant and sensitivity recessive (Harms et al. (1990) *Theor. Appl. Genet.* 80:353-358; Kang (1993) supra; Green & Uhlrich (1993) *Weed Sci.* 41:508-516; Green & Uhlrich (1994) *Pestic. Sci.* 40:187-191). It is also known that tolerant maize plants metabolize nicosulfuron by hydroxylation, with the characteristics of a cytochrome P450 (Forme-Pfister et al. (1990) *Pesticide Biochem. Physiol.* 37:165-173; Brown & Cotterman (1994) *Chem. Plant Prot.* 10:47-81). It has been suggested that the same corn gene responsible for determining tolerance to some sulfonylurea herbicides is also responsible for the tolerance to bentazon (Barrett et al. (1997) Role of cytochrome P-450 in herbicide metabolism and selectivity and multiple herbicide metabolizing cytochrome P-450 activities in maize. In K. K. Hatzios, ed. Regulation of Enzymatic Systems Detoxifying Xenobiotics in Plants. Dordrecht: Kluwer Academic. pp. 35-50; Green (1998) *Weed Technology* 12:474-477) and HPPD inhibitor herbicides such as mesotrione (Green & Williams (2004) supra; Williams et al. (2005) *HortScience* 40(6):1801-1805). Recent advances in the development of the maize physical map and integrated markers (Bortiri et al. (2006) *Curr Opin Plant Biol.* 9(2):164-71) has allowed a positional cloning approach to be used for identifying the Nsf1 locus.

The Nsf1 resistance gene of the embodiments of the present invention encodes a novel gene related to the cytochrome P450 family. While multiple cytochrome P450 genes have been described, they differ widely in their response to different pathogens and exact action. The novel cytochrome P450 gene described in this disclosure has been demonstrated to provide improved tolerance or resistance to numerous herbicides, including nicosulfuron, rimsulfuron, primisulfuron, thifensulfuron and mesotrione.

SUMMARY OF THE INVENTION

The present invention is directed to embodiments including an isolated polynucleotide comprising a nucleotide sequence encoding a polypeptide capable of conferring resistance to at least one herbicide, wherein the polypeptide has an amino acid sequence of at least 85, 90 or 95% identity, when compared to SEQ ID NO:1 based on the Needleman-Wunsch alignment algorithm, or a complement of the nucleotide sequence, wherein the complement and the nucleotide sequence consist of the same number of nucleotides and are 100% complementary. The herbicides to which the polynucleotide of the embodiments imparts resistance include members of the ALS-inhibiting class; the pigment synthesis-inhibiting class; the PPO-inhibiting class; the PS II-inhibiting class; and the synthetic auxin class of herbicides. The polynucleotide of the embodiments may impart resistance to one or more herbicides from the same class, or from different classes, including representative members from all 5 classes.

Additional embodiments of the present invention include a vector comprising the polynucleotide of the embodiments and a recombinant DNA construct comprising the polynucleotide of the embodiments, operably linked to at least one regulatory sequence. A plant cell, as well as a plant and a seed each comprising the recombinant DNA construct of an embodiment of the present invention are also encompassed. Also included are plants comprising additional polynucleotides encoding polypeptides responsible for traits of interest, such as polypeptides having glyphosate N-acetyltransferase activity, insecticidal Bt polypeptides, and other polypeptides of interest. Plants comprising these polynucleotides include monocots and dicots, including, but not limited to, maize, wheat, barley, oats, switchgrass, sorghum, rice, soybean, canola, potato, cotton, and sunflower.

The methods embodied by the present invention include 1) a method for transforming a cell, comprising transforming a cell with the polynucleotide of an embodiment of the present invention, 2) a method for producing a plant comprising transforming a plant cell with the recombinant DNA construct of an embodiment of the present invention and regenerating a plant from the transformed plant cell, and 3) methods of conferring or enhancing resistance to at least one herbicide, comprising transforming a plant with the recombinant DNA construct of an embodiment of the present invention, thereby conferring or enhancing resistance to at least one herbicide, such as a member of the ALS-inhibiting class; the pigment synthesis-inhibiting class; the PPO-inhibiting class; the PS II-inhibiting class; and the synthetic auxin class of herbicides.

In addition, an embodiment of the invention is a variant allele of the Nsf1 sequence in which a specific single amino acid change (see Example 2) renders the gene inoperative, resulting in sensitivity to at least one ALS or HPPD inhibitor herbicide to which most corn is resistant. Accordingly, an additional method embodied by the present invention is a method of using the variant of the Nsf1 gene as a marker in breeding strategies to avoid incorporating the sensitive allele.

Methods of altering the level of expression of a protein capable of conferring resistance to at least one herbicide in a plant cell comprising (a) transforming a plant cell with the recombinant DNA construct of an embodiment of the present invention and (b) growing the transformed plant cell under conditions that are suitable for expression of the recombinant DNA construct wherein expression of the recombinant DNA construct results in production of altered levels of a protein capable of conferring resistance to at least one herbicide in the transformed host are also embodied by the present invention. The herbicides for which resistance may be conferred include, for example, members of the ALS-inhibiting class; the pigment synthesis-inhibiting class; the PPO-inhibiting class; the PS II-inhibiting class; and the synthetic auxin class of herbicides.

Herbicides to which a polynucleotide of the embodiments may confer or enhance resistance include, but are not limited to, herbicides selected from the ALS-inhibiting class of herbicides such as nicosulfuron, rimsulfuron, primisulfuron, imazethapyr, chlorsulfuron, chlorimuron ethyl, triasulfuron, flumetsulam and imazaquin. Additionally, such herbicides may be selected from the pigment synthesis-inhibiting class of herbicides, such as isoxaflutole, topramezone, sulcatrione and tembotrione. Such herbicides may also be selected from the PPO-inhibiting class of herbicides, such as acifluorfen, flumioxan and sulfentrazone. Optionally, such herbicides may be selected from the PS II-inhibiting class of herbicides, such as diuron, linuron, bentazon and chlorotoluron. Such herbicides may also be selected from the synthetic auxin class of herbicides, such as dicamba.

Methods of the embodiments include a method of determining the presence of the polynucleotide of the embodiments or the Nsf1 locus in a plant, comprising at least one of: (a) isolating nucleic acid molecules from the plant and determining if an Nsf1 gene is present by attempting to amplify sequences homologous to the polynucleotide; or (b) isolating nucleic acid molecules from the plant and performing a Southern hybridization, or (c) isolating proteins from the plant and performing a western blot using antibodies to the NSF1 protein, or (d) isolating proteins from the plant and performing an ELISA assay using antibodies to the NSF1 protein, thereby determining the presence of the polynucleotide of claim 1 in the plant.

Also encompassed by the embodiments are plants with enhanced tolerance to at least one herbicide, comprising the Nsf1 gene in a recombinant DNA construct. Such plants further comprise a second herbicide resistance gene providing a certain level of tolerance to a herbicide selected from a class of herbicides selected from the group consisting of:
 (a) the ALS-inhibiting class;
 (b) the pigment synthesis-inhibiting class;
 (c) the PPO-inhibiting class;
 (d) the PS II-inhibiting class; and
 (e) the synthetic auxin class;

such that the presence of the Nsf1 gene confers upon the plant a higher level of tolerance to the same herbicide than the tolerance level exhibited by a plant comprising the second herbicide resistance gene but not comprising the Nsf1 gene.

Also encompassed by the embodiments are soybean plants comprising the Nsf1 gene, wherein such soybean plants also exhibit soybean cyst nematode resistance. Such plants may have been created through transformation or plant breeding techniques, and may have been bred from germplasm such as those selected from the group consisting of, Peking, PI88788, PI89772, PI90763, PI209332, PI404189A, PI437654, PI438489B, PI467312, PI468916, Hartwig, J87-233, and progeny derived from any of the listed sources.

BRIEF DESCRIPTION OF THE DRAWINGS

FIG. 1(a-e) is a multiple sequence alignment of the polypeptide sequence of the embodiments (SEQ ID NO: 2) comparing it to other known Cytochrome P450 polypeptides (SEQ ID NOs: 3-13). FIG. 1d also indicates the position of the most commonly conserved domain of the cytochrome P450 family (SEQ ID NO: 14). Identical residues in the alignment are indicated in upper case letters.

FIG. 2(a-b) is a multiple sequence alignment of the polypeptide sequences of several sensitive and resistant corn lines showing the commonly conserved domain of the cytochrome P450 family (SEQ ID NO: 14) as well as variations among the sequences.

DETAILED DESCRIPTION OF THE INVENTION

Embodiments of the present invention provide compositions and methods directed to inducing herbicide resistance in plants. The compositions are novel nucleotide and amino acid sequences that confer or enhance resistance to one or more members of one or more classes of herbicides, including the ALS-inhibiting, PPO-inhibiting, pigment synthesis-inhibiting, PS II-inhibiting and synthetic auxin herbicide classes, whose members include, but are not limited to, nicosulfuron, rimsulfuron, primisulfuron, and mesotrione. Specifically, certain embodiments provide polypeptides having the amino acid sequence set forth in SEQ ID NO: 2, and variants and fragments thereof. Isolated nucleic acid molecules, and variants and fragments thereof, comprising nucleotide sequences that encode the amino acid sequence shown in SEQ ID NO: 2 are further provided.

One example of the native nucleotide sequence that encodes the polypeptide of SEQ ID NO: 2 is set forth in SEQ ID NO: 1. Plants, plant cells, seeds, and microorganisms comprising a nucleotide sequence that encodes a polypeptide of the embodiments are also disclosed herein.

The full length polypeptide of the embodiments (SEQ ID NO: 2) shares varying degrees of homology with known polypeptides of the cytochrome P450 family. In particular, the novel polypeptide of the embodiments shares homology with cytochrome P450 proteins isolated from *Oryza sativa*: Accession Nos. XP_469850 (SEQ ID NO: 3), ABC69856 (SEQ ID NO: 4); XP_469849 (SEQ ID NO: 11) and XP_469851 (SEQ ID NO: 12); and XP_469852 (SEQ ID NO: 13) and *Lolium rigidum*: Accession Nos. AAK38080 (SEQ ID NO: 5); AAK38079 (SEQ ID NO: 6); AAK38081 (SEQ ID NO: 7); BAD27508 (SEQ ID NO: 8); BAD27507 (SEQ ID NO: 9) and BAD27506 (SEQ ID NO: 10). FIG. 1 provides an alignment of the amino acid sequence set forth in SEQ ID NO: 2 with the *O. sativa* and *L. rigidum* cytochrome P450 proteins (SEQ ID NOs: 3-13).

Amino acid alignments performed using the GAP program indicate that SEQ ID NO:2 shares the sequence similarities shown in Table 1 with the *O. sativa* and *L. rigidum* cytochrome P450 proteins.

TABLE 1

Comparison of NSF1 Peptide to other Cytochrome P450 peptides

| Other Cytochrome P450 Protein | Percent Identity | Percent Similarity |
|---|---|---|
| XP_469850 (SEQ ID NO: 3) | 67% | 76% |
| ABC69856 (SEQ ID NO: 4) | 67% | 76% |
| AAK38080 (SEQ ID NO: 5) | 68% | 76% |
| AAK38079 (SEQ ID NO: 6) | 67% | 77% |
| AAK38081 (SEQ ID NO: 7) | 67% | 76% |
| BAD27508 (SEQ ID NO: 8) | 67% | 76% |
| BAD27507 (SEQ ID NO: 9) | 67% | 76% |
| BAD27506 (SEQ ID NO: 10) | 67% | 76% |
| XP_469849 (SEQ ID NO: 11) | 66% | 75% |
| XP_469851 (SEQ ID NO: 12) | 61% | 71% |
| XP_469852 (SEQ ID NO: 13) | 60% | 72% |

The cytochrome P450 family of genes in plants catalyze extremely diverse and often complex regiospecific and/or stereospecific reactions in the biosynthesis or catabolism of plant bioactive molecules. (Morant et al. (2003) *Curr. Opin. Biotech.* 14(2): 151-162). P450s are heme proteins that catalyze the activation of molecular oxygen by using electrons from NADPH. In the *Arabidopsis thaliana* genome alone, there are an estimated over 300 cytochromes P450 (Werck-Reichhart et al. (2000) *Trends in Plant Science* 5(3): 116-123). Common structural features occur in plant cytochromes P450 and help identify them as such. These features include the F-X-X-G-X-R-X-C-X-G (SEQ ID NO: 14) motif generally found near the C-terminus (see FIG. 1d). About 150 residues upstream, another conserved motif generally found follows the A/G-G-X-D/E-T-T/S (SEQ ID NO: 15) motif and corresponds to the region of the peptide responsible for oxygen-binding and activation.

The nucleic acids and polypeptides of the embodiments find use in methods for conferring or enhancing herbicide resistance to a plant. Accordingly, the compositions and methods disclosed herein are useful in protecting plants from damage caused by herbicides. "Herbicide resistance" is intended to mean that a plant or plant cell has the ability to tolerate a higher concentration of a herbicide than plants or cells which are not resistant, or to tolerate a certain concentration of a herbicide for a longer time than cells or plants which are not resistant. That is, herbicides are prevented from causing plant injury, or the injury caused by the herbicide is minimized or lessened, such as, for example, the reduction of leaf yellowing and associated yield loss. One of skill in the art will appreciate that the compositions and methods disclosed herein can be used with other compositions and methods available in the art for increasing or enhancing plant herbicide resistance. The term "enhance" refers to improve, increase, amplify, multiply, elevate, raise, and the like.

In particular aspects, the embodiments include methods for conferring or enhancing herbicide resistance in a plant comprising introducing into a plant at least one DNA construct, wherein the DNA construct comprises a nucleotide sequence encoding a herbicide resistance polypeptide of the embodiments operably linked to a promoter that drives expression in the plant. The plant expresses the polypeptide, thereby conferring or enhancing herbicide resistance upon the plant, or improving the plant's inherent level of resistance. In particular embodiments, the gene confers or enhances resistance to at least one herbicide of the ALS-inhibiting, pigment synthesis-inhibiting, PPO-inhibiting, PS II-inhibiting or synthetic auxin herbicide classes, whose members include, but are not limited to, the herbicides nicosulfuron, rimsulfuron, primisulfuron, thifensulfuron, bentazon, and mesotrione.

Expression of a polypeptide of the embodiments may be targeted to specific plant tissues, but generally in the case of herbicide resistance, continuous expression is desired throughout the cells of a plant. Therefore, while many promoters could be used in the embodiments of the invention, generally constitutive promoters are utilized. A constitutive promoter is a promoter that directs expression of a gene throughout the various parts of a plant and continuously throughout plant development.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the embodiments can be produced either from a nucleic acid disclosed herein, or by the use of standard molecular biology techniques. For example, a truncated protein of the embodiments can be produced by expression of a recombinant nucleic acid of the embodiments in an appropriate host cell, or alternatively by a combination of ex vivo procedures, such as protease digestion and purification.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The embodiments of the invention encompass isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the protein of the embodiments, or a biologically active portion thereof, is recombinantly produced, optimally culture medium represents less than about 30%, about 20%, about 10%, about 5%, or about 1% (by dry weight) of chemical precursors or non-protein-of-interest chemicals.

Fragments and variants of the disclosed nucleotide sequences and proteins encoded thereby are also encompassed by the embodiments. By "fragment" is intended a portion of the nucleotide sequence or a portion of the amino acid sequence and hence protein encoded thereby. Fragments of a nucleotide sequence may encode protein fragments that retain the biological activity of the native protein and hence have the ability to confer or enhance resistance to at least one herbicide of the ALS-inhibiting, PPO-inhibiting, pigment synthesis-inhibiting, PS II-inhibiting or synthetic auxin herbicide class. Alternatively, fragments of a nucleotide sequence that are useful as hybridization probes do not necessarily encode fragment proteins retaining biological activity. Thus, fragments of a nucleotide sequence may range from at least about 15 nucleotides, about 50 nucleotides, about 100 nucleotides, and up to the full-length nucleotide sequence encoding the polypeptides of the embodiments.

A fragment of a nucleotide sequence that encodes a biologically active portion of a polypeptide of the embodiments will encode at least about 15, about 25, about 30, about 40, or about 50 contiguous amino acids, or up to the total number of amino acids present in a full-length polypeptide of the embodiments (for example, 521 amino acids for SEQ ID NO: 2). Fragments of a nucleotide sequence that are useful as hybridization probes or PCR primers generally need not encode a biologically active portion of a protein.

As used herein, "full-length sequence" in reference to a specified polynucleotide means having the entire nucleic acid sequence of a native sequence. By "native sequence" is intended an endogenous sequence, i.e., a non-engineered sequence found in an organism's genome.

Thus, a fragment of a nucleotide sequence of the embodiments may encode a biologically active portion of a polypeptide, or it may be a fragment that can be used as a hybridization probe or PCR primer using methods disclosed below. A biologically active portion of an herbicide resistance polypeptide can be prepared by isolating a portion of one of the nucleotide sequences of the embodiments, expressing the encoded portion of the protein and assessing the ability of the encoded portion of the protein to confer or enhance herbicide resistance in a plant. Nucleic acid molecules that are fragments of a nucleotide sequence of the embodiments comprise at least about 15, about 20, about 50, about 75, about 100, or about 150 nucleotides, or up to the number of nucleotides present in a full-length nucleotide sequence disclosed herein (for example, 1563 nucleotides for SEQ ID NO: 1).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode a protein of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein.

Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 2 are disclosed. Percent sequence identity between any two polypeptides can be calculated using sequence alignment programs and parameters described elsewhere herein. Where any given pair of polynucleotides of the embodiments is evaluated by comparison of the percent sequence identity shared by the two polypeptides they encode, the percent sequence identity between the two encoded polypeptides is at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the embodiments are biologically active, that is they continue to possess the desired biological activity of the native protein, that is, the ability to confer or enhance plant herbicide resistance as described herein. Such variants may result from, for example, genetic polymorphism or from human manipulation. Biologically active variants of a native protein of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the amino acid sequence for the native protein as determined by sequence alignment programs and parameters described elsewhere herein. A biologically active variant of a protein of the embodiments may differ from that protein by as few as about 1-15 amino acid residues, as few as about 1-10, such as about 6-10, as few as about 5, as few as 4, 3, 2, or even 1 amino acid residue.

The proteins of the embodiments may be altered in various ways including amino acid substitutions, deletions, truncations, and insertions. Methods for such manipulations are generally known in the art. For example, amino acid sequence variants and fragments of the herbicide resistance proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the embodiments include both the naturally occurring sequences as well as mutant forms. Likewise, the proteins of the embodiments encompass both naturally occurring proteins as well as variations and modified forms thereof. Such variants will continue to possess the desired ability to confer or enhance plant resistance to at least one herbicide of the ALS-inhibiting, PPO-inhibiting, pigment synthesis-inhibiting, PS II-inhibiting or synthetic auxin herbicide classes. Obviously, the mutations that will be made in the DNA encoding the variant must not place the sequence out of reading frame and optimally will not create complementary regions that could produce secondary mRNA structure. See, EP Patent No. 0075444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by screening transgenic plants which have been transformed with the variant protein to ascertain the effect on the herbicide resistance characteristics of the plant.

Variant polynucleotides and proteins also encompass sequences and proteins derived from mutagenic or recombinogenic procedures, including and not limited to procedures such as DNA shuffling. One of skill in the art could envision modifications that would alter the range of herbicides to which the protein responds. With such a procedure, one or more different protein coding sequences can be manipulated to create a new protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the protein gene of the embodiments and other known protein genes to obtain a new gene coding for a protein with an improved property of interest, such as increased ability to confer or enhance plant herbicide resistance. Strategies for such DNA shuffling are known in the art. See, for example, US 2002/0058249; Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the embodiments can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the embodiments. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least about 60%, about 70%, about 75%, about 80%, about 85%, about 90%, about 91%, about 92%, about 93%, about 94%, about 95%, about 96%, about 97%, about 98%, about 99%, or greater sequence identity. Functions of orthologs are often highly conserved among species. Thus, isolated polynucleotides that encode for a protein that confers or enhances plant herbicide resistance and that hybridize under stringent conditions to the sequences disclosed herein, or to variants or fragments thereof, are encompassed by the embodiments.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, and are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the embodiments.

Methods for preparation of probes for hybridization and for construction of cDNA and genomic libraries are generally known in the art and are disclosed in Sambrook et al. (1989) supra.

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique and are optimally at least about 10 nucleotides in length, at least about 15 nucleotides in length, or at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) supra.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least 30 minutes. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138: 267-284: $T_m$=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) supra.

Various procedures can be used to check for the presence or absence of a particular sequence of DNA, RNA, or a protein. These include, for example, Southern blots, northern blots, western blots, and ELISA analysis. Techniques such as these are well known to those of skill in the art and many references exist which provide detailed protocols. Such references include Sambrook et al. (1989) supra, and Crowther, J. R. (2001), *The ELISA Guidebook*, Humana Press, Totowa, N.J., USA.

The following terms are used to describe the sequence relationships between two or more polynucleotides or polypeptides: (a) "reference sequence," (b) "comparison window," (c) "sequence identity," and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least about 20 contiguous nucleotides in length, and optionally can be about 30, about 40, about 50, about 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, and are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using Gap Weight of 50 and Length Weight of 3, and the nwsgapdna.cmp scoring matrix; % identity and % similarity for an amino acid sequence using Gap Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, and no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the embodiments to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the embodiments also encompass all forms of sequences including, and not limited to, single-stranded forms, double-stranded forms, and the like.

Isolated polynucleotides of the present invention can be incorporated into recombinant DNA constructs capable of introduction into and replication in a host cell. A "vector" may be such a construct that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., *Cloning Vectors: A Laboratory Manual*, 1985, supp. 1987; Weissbach and Weissbach, *Methods for Plant Molecular Biology, Academic Press*, 1989; and Flevin et al., *Plant Molecular Biology Manual*, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a signal peptide sequence for targeted expression, a transcription termination site, and/or a polyadenylation signal.

The terms "recombinant construct," "expression cassette," "expression construct," "chimeric construct," "construct," "recombinant DNA construct," "DNA construct" and "recombinant DNA fragment" are used interchangeably herein and are nucleic acid fragments. A recombinant construct comprises an artificial combination of nucleic acid fragments, including, and not limited to, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. Screening to obtain lines displaying the desired expression level and pattern of the polynucleotides or of the Nsf1 locus may be accomplished by amplification, Southern analysis of DNA, Northern analysis of mRNA expression, immunoblotting analysis of protein expression, phenotypic analysis, and the like.

The term "recombinant DNA construct" refers to a DNA construct assembled from nucleic acid fragments obtained from different sources. The types and origins of the nucleic acid fragments may be very diverse.

In some embodiments, DNA constructs comprising a promoter operably linked to a heterologous nucleotide sequence of the embodiments are further provided. The DNA constructs of the embodiments find use in generating transformed plants, plant cells, and microorganisms and in practicing the methods for inducing ALS and HPPD inhibitor herbicide resistance disclosed herein. The DNA construct will include 5' and 3' regulatory sequences operably linked to a polynucleotide of the embodiments. "Operably linked" is intended to mean a functional linkage between two or more elements. "Regulatory sequences" refer to nucleotides located upstream (5' non-coding sequences), within, or downstream (3' non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences. For example, an operable linkage between a polynucleotide of interest and a regulatory sequence (a promoter, for example) is functional link that allows for expression of the polynucleotide of interest. Operably linked elements may be contiguous or non-contiguous. When used to refer to the joining of two protein coding regions, operably linked is intended to mean that the coding regions are in the same reading frame. The coding sequence may additionally contain a sequence used to target the protein to the chloroplast, the vacuole, the endoplasmic reticulum or to the outside of the cell. The cassette may additionally contain at least one additional gene to be cotransformed into the organism. Alternatively, the additional gene(s) can be provided on multiple DNA constructs. Such a DNA construct is provided with a plurality of restriction sites and/or recombination sites for insertion of the polynucleotide that encodes a herbicide resistance polypeptide to be under the transcriptional regulation of the regulatory regions. The DNA construct may additionally contain selectable marker genes.

The DNA construct will include in the 5'-3' direction of transcription, a transcriptional initiation region (i.e., a promoter), translational initiation region, a polynucleotide of the embodiments, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor 11 gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

A number of promoters can be used in the practice of the embodiments, including the native promoter of the polynucleotide sequence of interest. The promoters can be selected based on the desired outcome. A wide range of plant promoters are discussed in the recent review of Potenza et al. (2004) *In Vitro Cell Dev Biol—Plant* 40:1-22, herein incorporated by reference. For example, the nucleic acids can be combined with constitutive, tissue-preferred, pathogen-inducible, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV $^{35}$S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

DNA constructs may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the DNA construct, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The DNA construct can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the embodiments.

The gene of the embodiments can be expressed as a transgene in order to make plants resistant to at least one herbicide of the ALS-inhibiting, PPO-inhibiting, pigment synthesis-inhibiting, PS II-inhibiting or synthetic auxin herbicide classes. Using the different promoters described elsewhere in this disclosure, this will allow its expression in a modulated form in different circumstances. One can also insert the entire gene, both native promoter and coding sequence, as a transgene. Finally, using the gene of the embodiments as a transgene will allow quick combination with other traits, such as insect or fungal resistance.

In certain embodiments the nucleic acid sequences of the embodiments can be stacked with any combination of polynucleotide sequences of interest, which may be transgenic or non-transgenic, in order to create plants with a desired phenotype. For example, the polynucleotides of the embodiments may be stacked with any other polynucleotides of the embodiments, or with other genes. The combinations generated can also include multiple copies of any one of the polynucleotides of interest. The polynucleotides of the embodiments can also be stacked with any other gene or combination of genes to produce plants with a variety of desired trait combinations including and not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the embodiments can also be stacked with traits desirable for insect, disease or herbicide resistance (e.g., *Bacillus thuringiensis* toxin proteins (U.S. Pat. Nos. 5,366,892; 5,747,450; 5,737,514; 5723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations (Lee et al., (1988) *EMBO J.* 7(5):1241-1248), resistance to inhibitors of glutamine synthase such as phosphinothricin or basta (e.g., bar gene; De Block et al. (1987) *EMBO J.* 6:2513-2518); HPPD genes that confer tolerance to HPPD inhibiting herbicides such as mesotrione or isoxaflutole (Matringe et al. (2005) *Pest Management Science* 61:269-276; Dufourmantel et al., (2007) *Plant Biotech. J.* 5:118-133; see also WO1997049816), genes for tolerance to PPO inhibiting herbicides (Li and Nicholl (2005) *Pest Management Science* 61:277-285); synthetic auxin resistance genes (U.S. patent application 2005/014737 and Herman et al., (2005) *J. Biol. Chem.* 280: 24759-24767), and glyphosate resistance (epsps genes, gat genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, yield improvement, or transformation technology traits such as cell cycle regulation or gene targeting (e.g. WO 99/61619; WO 00/17364; WO 99/25821), the disclosures of which are herein incorporated by reference.

These stacked combinations can be created by any method including and not limited to cross breeding plants by any conventional or TopCross® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Further embodiments include plants obtainable by a method comprising: crossing a plant containing the Nsf1 gene as a first parent plant, with a different plant that lacks an Nsf1 gene as a second parent plant, thereby to obtain progeny comprising the Nsf1 gene of the first parent; and optionally further comprising one or more further breeding steps to obtain progeny of one or more further generations comprising the Nsf1 gene of the first parent. Such embodied plants can include both inbred and hybrid plants. Seeds of such plants, including those seeds which are homozygous and heterozygous for the Nsf1 gene, and methods of obtaining plant products resulting from the processing of those seeds are embodied in the invention. Using such seed in food or feed or the production of a corn product, such as flour, meal and oil is also an embodiment of the invention.

An "ancestral line" or "progenitor" is a parent line used as a source of genes, e.g., for the development of elite lines. "Progeny" are the descendents of the ancestral line, and may be separated from their ancestors by many generations of breeding. An "elite line" or "elite variety" is an agronomically superior line or variety that has resulted from many cycles of breeding and selection for superior agronomic performance. Similarly, "elite germplasm" is an agronomically superior germplasm, typically derived from and/or capable of giving rise to a plant with superior agronomic performance, such as an existing or newly developed elite line of corn or soybeans.

Also embodied in the invention is the use of molecular markers to move the gene or transgene into elite lines using breeding techniques. Molecular markers can be used in a variety of plant breeding applications (eg see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in the plants development, e.g. seed characteristics. Since DNA marker assays are less laborious, and take up less physical space, than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination can not occur between the marker and the gene. Such a marker is called a 'perfect marker'.

Optionally, the nucleic acids of the embodiments may be targeted to the chloroplast for expression. In this manner, where the nucleic acid is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6):789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36):27447-27457); and the light harvesting chlorophyll a/b binding protein (LHBP) (Lamppa et al. (1988) *J. Biol. Chem.* 263:14996-14999). See also Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The methods of the embodiments may involve, and are not limited to, introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the embodiments do not depend on a particular method for introducing a sequence into a plant, only that the polynucleotide gains access to the interior of at least one cell of the plant. Methods for introducing polynucleotides into plants are known in the art including, and not limited to, stable transformation methods, transient transformation methods, and virus-mediated methods.

"Transformation" refers to the transfer of a nucleic acid fragment into the genome of a host organism, resulting in genetically stable inheritance. Host organisms containing the transformed nucleic acid fragments are referred to as "transgenic" organisms. "Host cell" refers the cell into which transformation of the recombinant DNA construct takes place and may include a yeast cell, a bacterial cell, and a plant cell. Examples of methods of plant transformation include *Agrobacterium*-mediated transformation (De Blaere et al., 1987, *Meth. Enzymol.* 143:277) and particle-accelerated or "gene gun" transformation technology (Klein et al., 1987, *Nature* (London) 327:70-73; U.S. Pat. No. 4,945,050), among others.

"Stable transformation" is intended to mean that the nucleotide construct introduced into a plant integrates into the genome of the plant and is capable of being inherited by the progeny thereof. "Transient transformation" or "transient expression" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, Sanford et al., U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the embodiments provides transformed seed (also referred to as "transgenic seed") having a nucleotide construct of the embodiments, for example, a DNA construct of the embodiments, stably incorporated into their genome.

As used herein, the term plant includes plant cells, plant protoplasts, plant cell tissue cultures from which maize plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the embodiments, provided that these parts comprise the introduced polynucleotides.

The embodiments of the invention may be used to confer or enhance herbicide resistance in plants, especially soy (*Glycine max*). Other plant species may also be of interest in practicing the embodiments of the invention, including, and not limited to, other dicot and monocot crop plants. The maize gene of the embodiments is commonly found in the majority of commercial corn lines, most of which are naturally tolerant to at least one, and usually several, synthetic auxin, ALS-, PS II- and pigment synthesis-inhibitor herbicides, such as rimsulfuron, nicosulfuron and mesotrione.

It is therefore envisioned that the same tolerance to certain herbicides present in most corn lines can be extended to other crop plants by transgenic means though the use of the endogenous maize Nsf1 gene and variants thereof. Listings of maize lines with tolerance or sensitivity to selected SU herbicides are widely available, such as those provided by the USDA, ARS, National Genetic Resources Program. *Germplasm Resources Information Network*—(*GRIN*). [Online Database] National Germplasm Resources Laboratory, Beltsville, Md. [retrieved on Mar. 6, 2006]: Retrieved from the internet: <URL: http://www.ars-grin.gov/cgi-bin/npgs/html/dno_eval_acc.pl?89201+153002+21>; and the "Maize Germplasm Lines" listings available from the Buckler Laboratory website [retrieved on Mar. 6, 2006]: Retrieved from the internet: <URL: http://www.maizegenetics.net/ index.php?page=germplasm/lines.html>, and also in reference articles such as Kang (1993) *J. Heredity.* 84(3): 216-217.

Where appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats (*Avena* spp.), barley, palm, coconut, castor bean, olive, beans (for example guar, locust bean, fenugreek, soybean, garden beans, mung beans, lima beans, fava beans), peas (such as cowpeas, field peas, lentils, chickpeas, etc.), vegetables, ornamentals, and conifers.

Other plants of interest for the invention include those which have the potential for use as biofuel crops, including, but not limited to, prairie grasses such as switchgrass (*Panicum virgatum*), elephant grass (*Pennisetum purpureum*), Johnson grass (*Sorghum halepense*), *Miscanthus* spp., as well as hybrid poplar and hybrid willow trees.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

The embodiments provide not only a gene for use in transgenic applications, but sequences and methods that allow the resistance gene to be used as a marker in corn breeding strategies. For example, the gene of the embodiments, or the locus containing it, may be identified in a crop line intended to be used for breeding. Breeders would generally want to avoid using crop lines that are sensitive to herbicides where there is usually natural tolerance. Accordingly, the identification of the sequence of the Nsf1 gene will help breeders to identify and avoid creating herbicide-sensitive lines.

Nucleic acid based markers can be developed and applied using many different technologies. Such technologies include, and are not limited to, Restriction Fragment Length Polymorphism (RFLP), Simple Sequence Repeat (SSR), Random Amplified Polymorphic DNA (RAPD), Cleaved Amplified Polymorphic Sequences (CAPS) (Rafalski and Tingey, 1993, Trends in Genetics 9:275-280), Amplified Fragment Length Polymorphism (AFLP) (Vos et al., 1995, Nucleic Acids Res. 23:4407-4414), Single Nucleotide Polymorphism (SNP) (Brookes, 1999, Gene 234:177-186), Sequence Characterized Amplified Region (SCAR) (Paran and Michelmore, 1993, Theor. Appl. Genet. 85:985-993), Sequence Tagged Site (STS) (Onozaki et al., 2004, Euphytica 138:255-262), Single Stranded Conformation Polymorphism (SSCP) (Orita et al., 1989, Proc Natl Acad Sci USA 86:2766-2770), Inter-Simple Sequence Repeat (ISSR) (Blair et al., 1999, Theor. Appl. Genet. 98:780-792), Inter-Retrotransposon Amplified Polymorphism (IRAP), Retrotransposon-Microsatellite Amplified Polymorphism (REMAP) (Kalendar et al. (1999) Theor. Appl. Genet. 98:704-711) and the like.

As used herein, "locus" shall refer to a genetically defined region of a chromosome carrying a gene or, possibly, two or more genes so closely linked that genetically they behave as a single locus, responsible for a phenotype. A "gene" shall refer to a specific gene within that locus, including its associated regulatory sequences. Thus, the Nsf1 locus refers to the chromosomal region genetically defined as conferring resistance to at least one herbicide of the ALS-inhibiting, PPO-inhibiting, pigment synthesis-inhibiting, PS II-inhibiting and synthetic auxin herbicide class. One embodiment of the present invention is the isolation of the Nsf1 gene and the demonstration that it is the gene responsible for the phenotype conferred by the presence of the locus. Genetically defined loci are by their nature not as precisely defined in terms of size as genes, which can be delineated molecularly.

Units, prefixes, and symbols may be denoted in their Si accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

EXAMPLES

The embodiments of the invention are further defined in the following Examples, in which all parts and percentages are by weight and degrees are Celsius, unless otherwise stated. It should be understood that these Examples, while indicating embodiments of the invention, are given by way of illustration only. From the above discussion and these Examples, one skilled in the art can ascertain the essential characteristics of the embodiments of this invention, and without departing from the spirit and scope thereof, can make various changes and modifications to adapt it to various usages and conditions. Thus, various modifications of the embodiments of the invention in addition to those shown and described herein will be apparent to those skilled in the art from the foregoing description. Such modifications are also intended to fall within the scope of the appended claims. The disclosure of each reference set forth herein is incorporated by reference in its entirety

Example 1

Identification of the Nsf1 Gene Through Positional Cloning

A BC1 population (expected 50% Nsf1/nsf1, 50% nsf1/nsf1) was developed using the sensitive inbred W703A as the recurrent parent, and either B73 or Q66 as the resistant line. Plants were misted with a 2.3 mM nicosulfuron, 0.5% v/v Kinetic surfactant solution at approximately the V3 stage. Both resistant and sensitive parents were also grown and sprayed as controls. In order to avoid falsely classifying a plant which may have died due to reasons other than the herbicide application, only resistant progeny were sampled and analyzed. A total of 96 resistant plants were used for the initial mapping. This was sufficient to place Nsf1 between markers umc1766 and umc2036, and thus on contig 202 of the maizeB73-based physical map ((Retrieved on Mar. 6, 2006) Retrieved from the internet <URL: http://www.gramene.org/Zea_mays/cytoview?contig=ctg202&x=44&y=9>).

Based on BAC-end sequences of a maize Mo17-based contig, flanking CAPS (cleaved amplified polymorphic sequence) markers were identified on BACs of contig 202.

For finer mapping of this interval, a total of 388 resistant plants were used in the next step. Based on sequencing of subcloned fragments of BACs in this interval, two flanking CAPs markers were found on overlapping BACs. Both of these markers had 2/388 recombinants.

Both of these BACs were sequenced and analyzed. Within the 163 kb region of the 2 BACs flanked by two proprietary markers, P1 and P2, there were several putative genes. For the third round of mapping, a total of 2584 resistant plants were used, and markers were developed to separate some of the genes. One marker showed 11/2584 (0.4%) recombinants, helping to eliminate certain genes as being responsible for the resistance. Two other markers each had 2 (0.08%) recombinants, eliminating yet another gene. Finally, a marker between two genes had a single recombinant (0.04%), eliminating one of those two genes. Thus it was determined which gene was the gene of interest. The gene, Nsf1, was determined to have homology to some cytochrome P450 genes known in the art.

Example 2

Analysis of the Nsf1 Gene

Analysis of the Gene 18 (Nsf1) sequence in the B73-derived BAC shows an open reading frame of 521 amino acids, and containing the conserved heme-binding motif FXXGXXXCXG (SEQ ID NO: 14) found in all cytochrome P450s (FIGS. 1d and 2b).

In order to determine if the Nsf1 allele was consistent across maize lines, three corn lines with unknown sensitivity levels to nicosulfuron were tested to determine their reaction and then evaluate their sequences. Plants were misted with a 2.3 mM nicosulfuron, 0.5% v/v Kinetic surfactant solution at approximately the V3 stage. Both known resistant and sensitive lines were also grown and sprayed as controls. Results of the testing of the three lines showed that lines Q66 and Black Mexican Sweet (BMS) were resistant and line A188 was sensitive.

Of these two other resistant lines, Q66 and BMS, also possess this ORF, although Q66 differs from both B73 and BMS by 3 amino acids (FIGS. 2a and 2b) These three variant amino acids are marked with bold type and rectangles in FIGS. 2a and 2b in the Q66 sequence string to show their positions. Analysis of a sensitive line, GA209, shows an insertion of 392 bp relative to the resistant lines which results in a frameshift and an open reading frame of only 338 amino acids (FIG. 2b). A survey of numerous North American sensitive lines showed that many of the sensitive lines contain this same insertion of unknown DNA.

Analysis of the sequence from the F2 sensitive line showed that there is only one nucleotide difference between B73 (SEQ ID NO: 2) and F2 (SEQ ID NO: 22), which changes amino acid 263 from arginine to threonine (FIG. 2b). This single change therefore eliminates the resistance phenotype and variant sequences with such a change are expected not to retain biological activity. This change is useful in developing an SNP to assist corn breeders in avoiding the susceptible allele.

Nsf1 is 67% identical to a rice cytochrome P450 which has recently been reported to control sulfonylurea sensitivity in that plant (Accession No: ABC69856, SEQ ID NO: 4).

Genomic sequence from B73 shows a single intron with the expected GT left border and AG right border. The position of the intron is shown in the sequence listing in SEQ ID NO: 16.

The cloning of this gene has a number of potential applications. It could be used as a selectable marker for transformation in a sensitive transformable line such as A188 (Ishida et al., (1996) *Nature Biotechnology* 14:745-750). A transgene designed to suppress the Nsf1 gene function would function as a dominant negative selectable marker. Nsf1 could also be used to create transgenic resistance in other plants, such as soybean, which are sensitive to this subclass of sulfonylureas.

Example 3

Testing of Maize Plants for Sensitivity to Nicosulfuron

Three corn lines with unknown sensitivity levels to nicosulfuron were tested to determine their reaction. Plants were misted with a 2.3 mM nicosulfuron, 0.5% v/v Kinetic surfactant solution at approximately the V3 stage. Both known resistant and sensitive lines were also grown and sprayed as controls. Results of the testing of the three lines showed that lines Q66 and BMS were resistant and line A188 was sensitive.

Example 4

Preparation of Transgenic Soybean Plants

The following stock solutions and media were used for transformation and regeneration of soybean plants:

Stock Solutions

Sulfate 100× Stock: 37.0 g $MgSO_4·7H_2O$, 1.69 g $MnSO_4·H_2O$, 0.86 g $ZnSO_4·7H_2O$, 0.0025 g $CuSO_4·5H_2O$.

Halides 100× Stock: 30.0 g $CaCl_2·2H_2O$, 0.083 g KI, 0.0025 g $CoCl_2·6H_2O$,

P, B, Mo 100× Stock: 18.5 g $KH_2PO_4$, 0.62 g $H_3BO_3$, 0.025 g $Na_2MoO_4·2H_2O$ Fe EDTA 100× Stock: 3.724 g $Na_2EDTA$, 2.784 g $FeSO_4·7H_2O$.

2,4-D Stock: 10 mg/mL.

Vitamin B5 1000× Stock: 10.0 g myo-inositol, 0.10 g nicotinic acid, 0.10 g pyridoxine HCl, 1 g thiamine.

Media (Per Liter)

SB196: 10 mL of each of the above stock solutions, 1 mL B5 Vitamin stock, 0.463 g $(NH_4)_2 SO_4$, 2.83 g $KNO_3$, 1 mL 2,4-D stock, 1 g asparagine, 10 g sucrose, pH 5.7.

SB103: 1 pk. Murashige & Skoog salts mixture, 1 mL B5 Vitamin stock, 750 mg $MgCl_2$ hexahydrate, 60 g maltose, 2 g gelrite, pH 5.7.

SB166: SB103 supplemented with 5 g per liter activated charcoal.

SB71-4: Gamborg's B5 salts (Gibco-BRL catalog No. 21153-028), 1 mL B5 vitamin stock, 30 g sucrose, 5 g TC agar, pH 5.7.

Soybean embryogenic suspension cultures were maintained in 35 mL liquid medium (SB196) on a rotary shaker (150 rpm) at 28° C. with fluorescent lights providing a 16-hour day/8-hour night cycle. Cultures were subcultured every 2 weeks by inoculating approximately 35 mg of tissue into 35 mL of fresh liquid media.

Soybean embryogenic suspension cultures were transformed by particle gun bombardment (see Klein et al. (1987) Nature 327:70-73) using a DuPont Biolistic PDS1000/He instrument.

The recombinant DNA plasmid used to express Nsf1 was on a separate recombinant DNA plasmid from the selectable marker gene. Both recombinant DNA plasmids were co-precipitated onto gold particles as follows. The DNAs in suspension were added to 50 µL of a 20-60 mg/mL 0.6 µm gold particle suspension and then combined with 50 µL $CaCl_2$ (2.5 M) and 20 µL spermidine (0.1 M). The mixture was pulse vortexed 5 times, spun in a microfuge for 10 seconds, and the supernatant removed. The DNA-coated particles are then washed once with 150 µL of 100% ethanol, pulse vortexed and spun in a microfuge again, and resuspended in 85 µL of anhydrous ethanol. Five µL of the DNA-coated gold particles are then loaded on each macrocarrier disk.

Approximately 150 to 250 mg of two-week-old suspension culture was placed in an empty 60 mm×15 mm petri plate and the residual liquid is removed from the tissue using a pipette. The tissue was placed about 3.5 inches away from a retaining screen and each plate of tissue was bombarded once. Membrane rupture pressure was set at 650 psi and the chamber was evacuated to −28 inches of Hg. Eighteen plates were bombarded, and, following bombardment, the tissue from each plate was divided between two flasks, placed back into liquid media, and cultured as described above.

Seven days after bombardment, the liquid medium was exchanged with fresh SB196 medium supplemented with 50 mg/mL hygromycin. The selective medium was refreshed weekly or biweekly. Seven weeks post-bombardment, green, transformed tissue was observed growing from untransformed, necrotic embryogenic clusters. Isolated green tissue was removed and inoculated into individual flasks to generate new, clonally-propagated, transformed embryogenic suspension cultures. Thus, each new line was treated as an independent transformation event. These suspensions were then maintained as suspensions of embryos clustered in an immature developmental stage through subculture or were regenerated into whole plants by maturation and germination of individual somatic embryos.

Transformed embryogenic clusters were removed from liquid culture and placed on solid agar medium (SB166) containing no hormones or antibiotics for one week. Embryos were cultured at 26° C. with mixed fluorescent and incandescent lights on a 16-hour day: 8-hour night schedule. After one week, the cultures were then transferred to SB103 medium and maintained in the same growth conditions for 3 additional weeks. Prior to transfer from liquid culture to solid medium, tissue from selected lines was assayed by PCR for the presence of the chimeric gene. Somatic embryos became suitable for germination after 4 weeks and were then removed from the maturation medium and dried in empty petri dishes for one to five days. The dried embryos were then planted in SB71-4 medium and allowed to germinate under the same light and germination conditions described above. Germinated embryos were transferred to sterile soil and grown to maturity.

Example 5

T0 and T1 Transgenic Plant Analysis

T0 Testing

Two different constructs comprising the Nsf1 gene were created to examine herbicide efficacy of the gene when transformed into soybean. The Nsf1 constructs were co-bombarded with a 35S:HYG insert to permit event selection using hygromycin.

At the V2 to V6 growth stage, a total of 127 T0 plants were sprayed with 35 g/ha rimsulfuron. All rimsulfuron treatments were applied with 0.2% w/w nonionic surfactant in a spray volume of 287 L/ha. In addition to the T0 plants, replications of three different controls were included—two positive and one negative. Individual plants were evaluated for herbicide response at ten days after treatment, and assigned a visual response score from 1 to 9 (1=dead plant to 9=no effect observed). Based upon high tolerance scores to the initial rimsulfuron spray, five T0 events were sprayed with an additional 35 g/ha rimsulfuron. Plants were rated for visual tolerance using a 1 to 9 score at ten days after the second application.

In the T0 generation, 4 of 51 events had improved tolerance compared to the controls at ten days after treatment with 35 g/ha rimsulfuron. Three of 51 T0 events had improved level of tolerance after an additional application of 35 g/ha rimsulfuron. Two of these 51 events were advanced to the T1 generation for more extensive herbicide testing.

T1 Testing

Two events from the T0 generation were advanced to the T1 generation for additional herbicide efficacy testing of the Nsf1 gene. Replicates of two controls, as well as T1 plants, were grown in greenhouse experiments and sprayed with mesotrione at one of two rates (200 g/ha or 50 g/ha), nicosulfuron (70 g/ha), or rimsulfuron (35 g/ha) at the V3 growth stage. All herbicide treatments were applied with 1% w/w modified seed oil adjuvant in a spray volume of 374 L/ha. Plants were rated for herbicide response at eight days after application using a 1 to 9 score as used in the T0 testing.

An expanded herbicide efficacy test was developed in a second T1 plant experiment for the same two events advanced from the T0 generation. At the V3 growth stage, plants were sprayed with different treatments of herbicides that would typically cause substantial crop injury when applied to commodity soybean at the rates examined. All herbicide treatments were applied in a spray volume of 287 L/ha. Isoxaflutole (140 g/ha), topramezone (140 g/ha), and sulcotrione (140 g/ha) were applied with 1% w/w modified seed oil adjuvant. Diuron treatments (560 g/ha) were applied with 1% w/w petroleum crop oil adjuvant. Acifluorfen (4480 g/ha), sulfentrazone (140 g/ha), flumioxazine (140 g/ha), and dicamba (280 g/ha) were applied with 0.25% w/w nonionic surfactant. Rimsulfuron (35 g/ha) treatments were applied with 0.5% w/w basic blend adjuvant. At eight and fifteen days after treatment, plants were rated visually for crop injury using a 0 to 100 scale (0=no injury to 100=dead plant). Since the T1 events were segregating, only the plants with the best overall scores were selected, corresponding to the 75% that would be expected to possess the transgene.

One of the two events had significantly better tolerance compared to the controls at 8 DAT and 15 DAT after application of acifluorfen, dicamba, diuron, flumioxazine, isoxaflutole, mesotrione, rimsulfuron, sulcotrione, sulfentrazone, and topramezone treatments. The second event had significantly better tolerance compared to the controls at 15 DAT after application of acifluorfen, dicamba, isoxaflutole, mesotrione, rimsulfuron, sulcotrione, sulfentrazone, and topramezone treatments. Although the exact expression level of the Nsf1 gene in the events tested was not determined, transgenic soybean plants comprising the maize Nsf1 gene displayed better tolerance to a range of different herbicides when compared directly to control plants.

What is claimed is:

1. A method of identifying a plant with resistance to at least two herbicides, wherein each herbicide is a member of a different class of herbicides selected from the group consisting of:
 (i) the ALS-inhibiting class;
 (ii) the pigment synthesis-inhibiting class;
 (iii) the PPO-inhibiting class;
 (iv) the PS II-inhibiting class; and
 (v) the synthetic auxin class
comprising
 (a) detecting the presence of a nucleotide sequence encoding a polypeptide wherein the polypeptide has an amino acid sequence of at least 85% identity, when compared to SEQ ID NO:2 based on the Needleman-Wunsch alignment algorithm, and
 (b) selecting for a plant with resistance to the at least two herbicides in said group.

2. The method of claim 1, wherein said method comprises isolating nucleic acid molecules from said plant and determining if an Nsf1 gene is present by attempting to amplify sequences homologous to the nucleotide sequence.

3. The method of claim 1, wherein said method comprises isolating nucleic acid molecules from said plant and performing a Southern or northern hybridization.

4. A method of identifying a plant with an Nsf1 locus, wherein said Nsf1 locus confers resistance to at least two herbicides, wherein each herbicide is a member of a different class of herbicides selected from the group consisting of:
 (i) the ALS-inhibiting class;
 (ii) the pigment synthesis-inhibiting class;
 (iii) the PPO-inhibiting class;
 (iv) the PS II-inhibiting class; and
 (v) the synthetic auxin class
comprising
 (a) detecting the presence of said Nsf1 locus in said plant wherein said Nsf1 locus comprises a nucleotide sequence encoding a polypeptide wherein the polypeptide has an amino acid sequence of at least 85% identity, when compared to SEQ ID NO:2 based on the Needleman-Wunsch alignment algorithm, and
 (b) selecting for a plant with conferred resistance to the at least two herbicides in said group.

5. The method of claim 4, wherein said method comprises isolating nucleic acid molecules from said plant and determining if the Nsf1 locus is present by attempting to amplify sequences homologous to the nucleotide sequence.

6. The method of claim 4, wherein said method comprises isolating nucleic acid molecules from said plant and performing a Southern or northern hybridization.

7. The method of claim 1, wherein said method comprises the use of molecular markers to determine the presence of the nucleotide sequence in said plant.

8. The method of claim 4, wherein said method comprises the use of molecular markers to determine the presence of the Nsf1 locus in said plant.

9. The method of any of claims 1-8, wherein said plant is selected from the group consisting of corn, soybean, sunflower, sorghum, canola, wheat, alfalfa, cotton, rice, barley, millet, sugar cane and switchgrass.

* * * * *

SEQUENCE LISTING

<160> NUMBER OF SEQ ID NOS: 26

<210> SEQ ID NO 1
<211> LENGTH: 1563
<212> TYPE: DNA
<213> ORGANISM: Zea mays
<220> FEATURE:
<221> NAME/KEY: CDS
<222> LOCATION: (1)...(1563)

<400> SEQUENCE: 1

```
atg gat aag gcc tac atc gcc gcc ctc tcc gcc gcc gcc ctc ttc ttg      48
Met Asp Lys Ala Tyr Ile Ala Ala Leu Ser Ala Ala Ala Leu Phe Leu
1               5                   10                  15 ctc cac tac ctc ctg ggc cgg cgg gcc ggc ggc gag ggc aag gcc aag      96
Leu His Tyr Leu Leu Gly Arg Arg Ala Gly Gly Glu Gly Lys Ala Lys
            20                  25                  30 gcc aag ggc tcg cgg cgg cgg ctc ccg ccg agc cct ccg gcg atc ccg     144
Ala Lys Gly Ser Arg Arg Arg Leu Pro Pro Ser Pro Pro Ala Ile Pro
        35                  40                  45 ttc ctg ggc cac ctc cac ctc gtc aag gcc ccg ttc cac ggg gcg ctg     192
Phe Leu Gly His Leu His Leu Val Lys Ala Pro Phe His Gly Ala Leu
    50                  55                  60 gcc cgc ctc gcg gcg cgc cac ggc ccg gtg ttc tcc atg cgc ctg ggg     240
Ala Arg Leu Ala Ala Arg His Gly Pro Val Phe Ser Met Arg Leu Gly
65                  70                  75                  80 acc cgg cgc gcc gtg gtc gtg tcg tcg ccg gac tgc gcc agg gag tgc     288
Thr Arg Arg Ala Val Val Val Ser Ser Pro Asp Cys Ala Arg Glu Cys
                85                  90                  95 ttc acg gag cac gac gtg aac ttc gcg aac cgg ccg ctg ttc ccg tcg     336
Phe Thr Glu His Asp Val Asn Phe Ala Asn Arg Pro Leu Phe Pro Ser
            100                 105                 110 atg cgg ctg gcg tcc ttc gac ggc gcc atg ctc tcc gtg tcc agc tac     384
Met Arg Leu Ala Ser Phe Asp Gly Ala Met Leu Ser Val Ser Ser Tyr
        115                 120                 125 ggc ccg tac tgg cgc aac ctg cgc cgc gtc gcc gcc gtg cag ctc ctc     432
Gly Pro Tyr Trp Arg Asn Leu Arg Arg Val Ala Ala Val Gln Leu Leu
    130                 135                 140 tcc gcg cac cgc gtc ggg tgc atg gcc ccc gcc atc gaa gcg cag gtg     480
Ser Ala His Arg Val Gly Cys Met Ala Pro Ala Ile Glu Ala Gln Val
145                 150                 155                 160 cgc gcc atg gtg cgg agg atg gac cgc gcc gcg gcc ggc ggc ggc         528
Arg Ala Met Val Arg Arg Met Asp Arg Ala Ala Ala Gly Gly Gly
                165                 170                 175 ggc gtc gcg cgc gtc cag ctc aag cgg cgg ctg ttc gag ctc tcc ctc     576
Gly Val Ala Arg Val Gln Leu Lys Arg Arg Leu Phe Glu Leu Ser Leu
            180                 185                 190 agc gtg ctc atg gag acc atc gcg cac acc aag acg tcc cgc gcc gag     624
Ser Val Leu Met Glu Thr Ile Ala His Thr Lys Thr Ser Arg Ala Glu
        195                 200                 205
```

```
                                                         -continued gcc gac gcc gac tcg gac atg tcg acc gag gcc cac gag ttc aag cag        672
Ala Asp Ala Asp Ser Asp Met Ser Thr Glu Ala His Glu Phe Lys Gln
    210             215                 220 atc gtc gac gag ctc gtg ccg tac atc ggc acg gcc aac cgc tgg gac        720
Ile Val Asp Glu Leu Val Pro Tyr Ile Gly Thr Ala Asn Arg Trp Asp
225             230                 235                 240 tac ctg ccg gtg ctg cgc tgg ttc gac gtg ttc ggc gtg agg aac aag        768
Tyr Leu Pro Val Leu Arg Trp Phe Asp Val Phe Gly Val Arg Asn Lys
                245                 250                 255 atc ctc gac gcc gtg ggc aga agg gac gcg ttc ctg ggg cgg ctc atc        816
Ile Leu Asp Ala Val Gly Arg Arg Asp Ala Phe Leu Gly Arg Leu Ile
            260                 265                 270 gac ggg gag cgg cgg agg ctg gac gct ggc gac gag agc gaa agt aag        864
Asp Gly Glu Arg Arg Arg Leu Asp Ala Gly Asp Glu Ser Glu Ser Lys
        275                 280                 285 agc atg att gcg gtg ctg ctc act ctg cag aag tcc gag cca gag gtc        912
Ser Met Ile Ala Val Leu Leu Thr Leu Gln Lys Ser Glu Pro Glu Val
    290                 295                 300 tac act gac act gtg atc act gct ctt tgc gcg aac cta ttc ggc gcc        960
Tyr Thr Asp Thr Val Ile Thr Ala Leu Cys Ala Asn Leu Phe Gly Ala
305             310                 315                 320 gga acg gag acc acg tcc acc acg acg gaa tgg gcc atg tca ctg ctg       1008
Gly Thr Glu Thr Thr Ser Thr Thr Thr Glu Trp Ala Met Ser Leu Leu
                325                 330                 335 ctg aac cac cgg gag gcg ctc aag aag gcg cag gcc gag atc gac gcg       1056
Leu Asn His Arg Glu Ala Leu Lys Lys Ala Gln Ala Glu Ile Asp Ala
            340                 345                 350 gcg gtg ggc acc tcc cgc ctg gtg acc gcg gac gac gtg ccc cac ctc       1104
Ala Val Gly Thr Ser Arg Leu Val Thr Ala Asp Asp Val Pro His Leu
        355                 360                 365 acc tac ctg cag tgc atc gtc gac gag acg ctg cgc ctg cac ccg gcc       1152
Thr Tyr Leu Gln Cys Ile Val Asp Glu Thr Leu Arg Leu His Pro Ala
    370                 375                 380 gcg ccg ctg ctg ctg ccg cac gag tcc gcc gcg gac tgc acg gtc ggc       1200
Ala Pro Leu Leu Leu Pro His Glu Ser Ala Ala Asp Cys Thr Val Gly
385             390                 395                 400 ggc tac gac gtg ccg cgc ggc acg atg ctg ctg gtc aac gtg cac gcg       1248
Gly Tyr Asp Val Pro Arg Gly Thr Met Leu Leu Val Asn Val His Ala
                405                 410                 415 gtc cac agg gac ccc gcg gtg tgg gag gac ccg gac agg ttc gtg ccg       1296
Val His Arg Asp Pro Ala Val Trp Glu Asp Pro Asp Arg Phe Val Pro
            420                 425                 430 gag cgg ttc gag ggc gcc ggc ggc aag gcc gag ggg cgc ctg ctg atg       1344
Glu Arg Phe Glu Gly Ala Gly Gly Lys Ala Glu Gly Arg Leu Leu Met
        435                 440                 445 ccg ttc ggg atg ggg cgc gcc aag tgc ccc ggg gag acg ctc gcg ctg       1392
Pro Phe Gly Met Gly Arg Arg Lys Cys Pro Gly Glu Thr Leu Ala Leu
    450                 455                 460 cgg acc gtc ggg ctg gtg ctc gcc acg ctg ctc cag tgc ttc gac tgg       1440
Arg Thr Val Gly Leu Val Leu Ala Thr Leu Leu Gln Cys Phe Asp Trp
465             470                 475                 480 gac acg gtt gat gga gct cag gtt gac atg aag gct agc ggc ggg ctg       1488
Asp Thr Val Asp Gly Ala Gln Val Asp Met Lys Ala Ser Gly Gly Leu
                485                 490                 495 acc atg ccc cgg gcc gtc ccg ttg gag gcc atg tgc agg ccg cgt aca       1536
Thr Met Pro Arg Ala Val Pro Leu Glu Ala Met Cys Arg Pro Arg Thr
            500                 505                 510 gct atg cgt ggt gtt ctt aag agg ctc                                   1563
Ala Met Arg Gly Val Leu Lys Arg Leu
        515                 520
```

<210> SEQ ID NO 2
<211> LENGTH: 521
<212> TYPE: PRT
<213> ORGANISM: Zea mays

<400> SEQUENCE: 2

```
Met Asp Lys Ala Tyr Ile Ala Ala Leu Ser Ala Ala Leu Phe Leu
 1               5                  10                  15

Leu His Tyr Leu Leu Gly Arg Arg Ala Gly Gly Glu Gly Lys Ala Lys
                20                  25                  30

Ala Lys Gly Ser Arg Arg Leu Pro Pro Ser Pro Pro Ala Ile Pro
            35                  40                  45

Phe Leu Gly His Leu His Leu Val Lys Ala Pro Phe His Gly Ala Leu
 50                  55                  60

Ala Arg Leu Ala Ala Arg His Gly Pro Val Phe Ser Met Arg Leu Gly
 65                  70                  75                  80

Thr Arg Arg Ala Val Val Val Ser Ser Pro Asp Cys Ala Arg Glu Cys
                 85                  90                  95

Phe Thr Glu His Asp Val Asn Phe Ala Asn Arg Pro Leu Phe Pro Ser
                100                 105                 110

Met Arg Leu Ala Ser Phe Asp Gly Ala Met Leu Ser Val Ser Ser Tyr
            115                 120                 125

Gly Pro Tyr Trp Arg Asn Leu Arg Arg Val Ala Ala Val Gln Leu Leu
130                 135                 140

Ser Ala His Arg Val Gly Cys Met Ala Pro Ala Ile Glu Ala Gln Val
145                 150                 155                 160

Arg Ala Met Val Arg Arg Met Asp Arg Ala Ala Ala Gly Gly Gly
                165                 170                 175

Gly Val Ala Arg Val Gln Leu Lys Arg Arg Leu Phe Glu Leu Ser Leu
            180                 185                 190

Ser Val Leu Met Glu Thr Ile Ala His Thr Lys Thr Ser Arg Ala Glu
            195                 200                 205

Ala Asp Ala Asp Ser Asp Met Ser Thr Glu Ala His Glu Phe Lys Gln
210                 215                 220

Ile Val Asp Glu Leu Val Pro Tyr Ile Gly Thr Ala Asn Arg Trp Asp
225                 230                 235                 240

Tyr Leu Pro Val Leu Arg Trp Phe Asp Val Phe Gly Val Arg Asn Lys
                245                 250                 255

Ile Leu Asp Ala Val Gly Arg Arg Asp Ala Phe Leu Gly Arg Leu Ile
            260                 265                 270

Asp Gly Glu Arg Arg Arg Leu Asp Ala Gly Asp Glu Ser Glu Ser Lys
            275                 280                 285

Ser Met Ile Ala Val Leu Leu Thr Leu Gln Lys Ser Glu Pro Glu Val
290                 295                 300

Tyr Thr Asp Thr Val Ile Thr Ala Leu Cys Ala Asn Leu Phe Gly Ala
305                 310                 315                 320

Gly Thr Glu Thr Thr Ser Thr Thr Thr Glu Trp Ala Met Ser Leu Leu
                325                 330                 335

Leu Asn His Arg Glu Ala Leu Lys Lys Ala Gln Ala Glu Ile Asp Ala
            340                 345                 350

Ala Val Gly Thr Ser Arg Leu Val Thr Ala Asp Asp Val Pro His Leu
            355                 360                 365

Thr Tyr Leu Gln Cys Ile Val Asp Glu Thr Leu Arg Leu His Pro Ala
```

-continued

```
                   370                 375                 380

Ala Pro Leu Leu Pro His Glu Ser Ala Ala Asp Cys Thr Val Gly
385                 390                 395                 400

Gly Tyr Asp Val Pro Arg Gly Thr Met Leu Leu Val Asn Val His Ala
                405                 410                 415

Val His Arg Asp Pro Ala Val Trp Glu Asp Pro Asp Arg Phe Val Pro
                420                 425                 430

Glu Arg Phe Glu Gly Ala Gly Lys Ala Glu Gly Arg Leu Leu Met
                435                 440                 445

Pro Phe Gly Met Gly Arg Arg Lys Cys Pro Gly Glu Thr Leu Ala Leu
450                 455                 460

Arg Thr Val Gly Leu Val Leu Ala Thr Leu Leu Gln Cys Phe Asp Trp
465                 470                 475                 480

Asp Thr Val Asp Gly Ala Gln Val Asp Met Lys Ala Ser Gly Gly Leu
                485                 490                 495

Thr Met Pro Arg Ala Val Pro Leu Glu Ala Met Cys Arg Pro Arg Thr
                500                 505                 510

Ala Met Arg Gly Val Leu Lys Arg Leu
                515                 520

<210> SEQ ID NO 3
<211> LENGTH: 732
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Accession No. XP_469850

<400> SEQUENCE: 3

Met Ala Phe Leu Gly Trp Ala Val Asp Ile Ala Arg Asp Ser Gly Ala
1               5                   10                  15

Ser Ser Ser Val Val Leu Thr Cys Asp Gly Tyr Gly Ser Ala Leu Tyr
                20                  25                  30

Phe Ser Pro Trp Asp Ser Val Pro Leu Pro Ala Thr Ala Ser Pro Asp
            35                  40                  45

Asp Gly Phe Leu Leu Pro Arg Phe Pro Asp Val Cys Val Gln Arg Ser
        50                  55                  60

Gln Phe Thr Asn His Leu Ala Pro Ala Asn Gly Thr Gly Gly Gly Gly
65                  70                  75                  80

Ser Arg Thr Gly Val Lys Glu Glu Ala Ser Glu Val Leu Ser Trp Pro
                85                  90                  95

Pro Thr Ser Lys Gln Ser Val Arg Arg Leu Glu Val Ala Glu His Trp
            100                 105                 110

Tyr Arg Leu Tyr Lys Thr Asp Asn Gln Arg Leu Ser Pro Asp Ser Gln
        115                 120                 125

Gln Val Ser Val Leu Ala Glu Ser His Cys Asp Leu Ala Ser Gly Asn
    130                 135                 140

Trp Lys Glu Ile Ser Ile His His Lys Lys Met Pro Ser Ser Thr Thr
145                 150                 155                 160

Thr Lys Thr Thr Thr Pro Ser Arg Asp Ala Trp Ile Val Ser Ala Arg
                165                 170                 175

Ser Asp Pro Phe His Leu Leu Leu Glu Ala Gln Ala Pro Leu Gly Ile
            180                 185                 190

Lys Ala Asp Ala Leu Ser Gln Ile Ala Ala Val His Gln Ser His Arg
        195                 200                 205
```

-continued

```
Asn Thr Ser His Ile Arg Glu Leu Ser Leu Ala Met Asp Asn Ala Tyr
    210                 215                 220
Ile Ile Ala Ile Leu Ser Val Ala Ile Leu Phe Leu Leu His Tyr Tyr
225                 230                 235                 240
Leu Leu Gly Arg Gly Asn Gly Ala Ala Arg Leu Pro Pro Gly Pro
            245                 250                 255
Pro Ala Val Pro Ile Leu Gly His Leu His Leu Val Lys Lys Pro Met
            260                 265                 270
His Ala Thr Met Ser Arg Leu Ala Glu Arg Tyr Gly Pro Val Phe Ser
        275                 280                 285
Leu Arg Leu Gly Ser Arg Arg Ala Val Val Val Ser Pro Gly Cys
290                 295                 300
Ala Arg Glu Cys Phe Thr Glu His Asp Val Thr Phe Ala Asn Arg Pro
305                 310                 315                 320
Arg Phe Glu Ser Gln Leu Leu Val Ser Phe Asn Gly Ala Ala Leu Ala
                325                 330                 335
Thr Ala Ser Tyr Gly Ala His Trp Arg Asn Leu Arg Arg Ile Val Ala
            340                 345                 350
Val Gln Leu Leu Ser Ala His Arg Val Gly Leu Met Ser Gly Leu Ile
        355                 360                 365
Ala Gly Glu Val Arg Ala Met Val Arg Arg Met Tyr Arg Ala Ala Ala
370                 375                 380
Ala Ser Pro Ala Gly Ala Ala Arg Ile Gln Leu Lys Arg Arg Leu Phe
385                 390                 395                 400
Glu Val Ser Leu Ser Val Leu Met Glu Thr Ile Ala His Thr Lys Ala
                405                 410                 415
Thr Arg Pro Glu Thr Asp Pro Asp Thr Asp Met Ser Val Glu Ala Gln
            420                 425                 430
Glu Phe Lys Gln Val Val Asp Glu Ile Ile Pro His Ile Gly Ala Ala
        435                 440                 445
Asn Leu Trp Asp Tyr Leu Pro Ala Leu Arg Trp Phe Asp Val Phe Gly
    450                 455                 460
Val Arg Arg Lys Ile Leu Ala Ala Val Ser Arg Arg Asp Ala Phe Leu
465                 470                 475                 480
Arg Arg Leu Ile Asp Ala Glu Arg Arg Leu Asp Asp Gly Asp Glu
                485                 490                 495
Gly Glu Lys Lys Ser Met Ile Ala Val Leu Leu Thr Leu Gln Lys Thr
            500                 505                 510
Glu Pro Glu Val Tyr Thr Asp Asn Met Ile Thr Ala Leu Thr Ala Asn
        515                 520                 525
Leu Phe Gly Ala Gly Thr Glu Thr Thr Ser Thr Thr Ser Glu Trp Ala
    530                 535                 540
Met Ser Leu Leu Leu Asn His Pro Asp Thr Leu Lys Lys Ala Gln Ala
545                 550                 555                 560
Glu Ile Asp Ala Ser Val Gly Asn Ser Arg Leu Ile Thr Ala Asp Asp
                565                 570                 575
Val Thr Arg Leu Gly Tyr Leu Gln Cys Ile Val Arg Glu Thr Leu Arg
            580                 585                 590
Leu Tyr Pro Ala Ala Pro Met Leu Leu Pro His Glu Ser Ser Ala Asp
        595                 600                 605
Cys Lys Val Gly Gly Tyr Asn Ile Pro Arg Gly Ser Met Leu Leu Ile
    610                 615                 620
```

```
Asn Ala Tyr Ala Ile His Arg Asp Pro Ala Val Trp Glu Glu Pro Glu
625                 630                 635                 640

Lys Phe Met Pro Glu Arg Phe Glu Asp Gly Gly Cys Asp Gly Asn Leu
            645                 650                 655

Leu Met Pro Phe Gly Met Gly Arg Arg Cys Pro Gly Glu Thr Leu
        660                 665                 670

Ala Leu Arg Thr Val Gly Leu Val Leu Gly Thr Leu Ile Gln Cys Phe
        675                 680                 685

Asp Trp Glu Arg Val Asp Gly Val Glu Val Asp Met Thr Glu Gly Gly
        690                 695                 700

Gly Leu Thr Ile Pro Lys Val Val Pro Leu Glu Ala Met Cys Arg Pro
705                 710                 715                 720

Arg Asp Ala Met Gly Gly Val Leu Arg Glu Leu Val
                725                 730
```

<210> SEQ ID NO 4
<211> LENGTH: 513
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Accession No.: ABC69856

<400> SEQUENCE: 4

```
Met Asp Asn Ala Tyr Ile Ile Ala Ile Leu Ser Val Ala Ile Leu Phe
1               5                   10                  15

Leu Leu His Tyr Tyr Leu Leu Gly Arg Gly Asn Gly Gly Ala Ala Arg
            20                  25                  30

Leu Pro Pro Gly Pro Pro Ala Val Pro Ile Leu Gly His Leu His Leu
        35                  40                  45

Val Lys Lys Pro Met His Ala Thr Met Ser Arg Leu Ala Glu Arg Tyr
50                  55                  60

Gly Pro Val Phe Ser Leu Arg Leu Gly Ser Arg Arg Ala Val Val Val
65                  70                  75                  80

Ser Ser Pro Gly Cys Ala Arg Glu Cys Phe Thr Glu His Asp Val Thr
                85                  90                  95

Phe Ala Asn Arg Pro Arg Phe Glu Ser Gln Leu Leu Val Ser Phe Asn
            100                 105                 110

Gly Ala Ala Leu Ala Thr Ala Ser Tyr Gly Ala His Trp Arg Asn Leu
        115                 120                 125

Arg Arg Ile Val Ala Val Gln Leu Leu Ser Ala His Arg Val Gly Leu
        130                 135                 140

Met Ser Gly Leu Ile Ala Gly Glu Val Arg Ala Met Val Arg Arg Met
145                 150                 155                 160

Tyr Arg Ala Ala Ala Ser Pro Ala Gly Ala Ala Arg Ile Gln Leu
                165                 170                 175

Lys Arg Arg Leu Phe Glu Val Ser Leu Ser Val Leu Met Glu Thr Ile
            180                 185                 190

Ala His Thr Lys Ala Thr Arg Pro Glu Thr Asp Pro Asp Thr Asp Met
        195                 200                 205

Ser Val Glu Ala Gln Glu Phe Lys Gln Val Val Asp Glu Ile Ile Pro
        210                 215                 220

His Ile Gly Ala Ala Asn Leu Trp Asp Tyr Leu Pro Ala Leu Arg Trp
225                 230                 235                 240

Phe Asp Val Phe Gly Val Arg Arg Lys Ile Leu Ala Ala Val Ser Arg
```

-continued

```
                245                 250                 255
Arg Asp Ala Phe Leu Arg Arg Leu Ile Asp Ala Glu Arg Arg Leu
            260                 265                 270

Asp Asp Gly Asp Glu Gly Glu Lys Lys Ser Met Ile Ala Val Leu Leu
            275                 280                 285

Thr Leu Gln Lys Thr Glu Pro Glu Val Tyr Thr Asp Asn Met Ile Thr
            290                 295                 300

Ala Leu Thr Ala Asn Leu Phe Gly Ala Gly Thr Glu Thr Thr Ser Thr
305                 310                 315                 320

Thr Ser Glu Trp Ala Met Ser Leu Leu Leu Asn His Pro Asp Thr Leu
                325                 330                 335

Lys Lys Ala Gln Ala Glu Ile Asp Ala Ser Val Gly Asn Ser Arg Leu
            340                 345                 350

Ile Thr Ala Asp Asp Val Thr Arg Leu Gly Tyr Leu Gln Cys Ile Val
            355                 360                 365

Arg Glu Thr Leu Arg Leu Tyr Pro Ala Ala Pro Met Leu Leu Pro His
            370                 375                 380

Glu Ser Ser Ala Asp Cys Lys Val Gly Gly Tyr Asn Ile Pro Arg Gly
385                 390                 395                 400

Ser Met Leu Leu Ile Asn Ala Tyr Ala Ile His Arg Asp Pro Ala Val
                405                 410                 415

Trp Glu Glu Pro Glu Lys Phe Met Pro Glu Arg Phe Glu Asp Gly Gly
            420                 425                 430

Cys Asp Gly Asn Leu Leu Met Pro Phe Gly Met Gly Arg Arg Arg Cys
            435                 440                 445

Pro Gly Glu Thr Leu Ala Leu Arg Thr Val Gly Leu Val Leu Gly Thr
450                 455                 460

Leu Ile Gln Cys Phe Asp Trp Glu Arg Val Asp Gly Val Glu Val Asp
465                 470                 475                 480

Met Thr Glu Gly Gly Gly Leu Thr Ile Pro Lys Val Val Pro Leu Glu
                485                 490                 495

Ala Met Cys Arg Pro Arg Asp Ala Met Gly Gly Val Leu Arg Glu Leu
            500                 505                 510

Val
```

```
<210> SEQ ID NO 5
<211> LENGTH: 517
<212> TYPE: PRT
<213> ORGANISM: Lolium rigidum
<220> FEATURE:
<221> NAME/KEY: PEPTIDE
<222> LOCATION: (0)...(0)
<223> OTHER INFORMATION: Accession No.:  AAK38080

<400> SEQUENCE: 5
```

```
Met Asp Lys Ala Tyr Ile Ala Ile Leu Ser Cys Ala Phe Leu Phe Leu
 1               5                  10                  15

Val His Tyr Val Leu Gly Lys Val Ser Asp Gly Arg Arg Gly Lys Lys
            20                  25                  30

Gly Ala Val Gln Leu Pro Pro Ser Pro Ala Val Pro Phe Leu Gly
            35                  40                  45

His Leu His Leu Val Asp Lys Pro Ile His Ala Thr Met Cys Arg Leu
            50                  55                  60

Ala Ala Arg Leu Gly Pro Val Phe Ser Leu Arg Leu Gly Ser Arg Arg
65                  70                  75                  80
```

```
Ala Val Val Ser Ser Glu Cys Ala Arg Glu Cys Phe Thr Glu
            85              90              95

His Asp Val Thr Phe Ala Asn Arg Pro Lys Phe Pro Ser Gln Leu Leu
            100             105             110

Val Ser Phe Asn Gly Thr Ala Leu Val Thr Ser Ser Tyr Gly Pro His
            115             120             125

Trp Arg Asn Leu Arg Arg Val Ala Thr Val Gln Leu Leu Ser Ala His
130             135             140

Arg Val Ala Cys Met Ser Gly Val Ile Ala Ala Glu Val Arg Ala Met
145             150             155             160

Ala Arg Arg Leu Phe His Ala Thr Glu Ala Ser Pro Asp Gly Ala Ala
                165             170             175

Arg Val Gln Leu Lys Arg Leu Phe Glu Leu Ser Leu Ser Val Leu
            180             185             190

Met Glu Thr Ile Ala Gln Thr Lys Ala Thr Arg Ser Glu Ala Asp Ala
            195             200             205

Asp Thr Asp Met Ser Val Glu Ala Gln Glu Phe Lys Glu Val Val Asp
        210             215             220

Lys Leu Ile Pro His Leu Gly Ala Ala Asn Met Trp Asp Tyr Leu Pro
225             230             235             240

Val Met Arg Trp Phe Asp Val Phe Gly Val Arg Asn Lys Ile Leu His
                245             250             255

Ala Val Ser Arg Arg Asp Ala Phe Leu Arg Arg Leu Ile Asp Ala Glu
                260             265             270

Arg Arg Arg Leu Ala Asp Gly Gly Ser Asp Gly Asp Lys Lys Ser Met
        275             280             285

Ile Ala Val Leu Leu Thr Leu Gln Lys Thr Glu Pro Lys Val Tyr Thr
            290             295             300

Asp Thr Met Ile Thr Ala Leu Cys Ala Asn Leu Phe Gly Ala Gly Thr
305             310             315             320

Glu Thr Thr Ser Thr Thr Thr Glu Trp Ala Met Ser Leu Leu Leu Asn
                325             330             335

His Pro Ala Ala Leu Lys Lys Ala Gln Ala Glu Ile Asp Ala Ser Val
            340             345             350

Gly Thr Ser Arg Leu Val Ser Val Asp Asp Val Pro Ser Leu Ala Tyr
            355             360             365

Leu Gln Cys Ile Val Ser Glu Thr Leu Arg Leu Tyr Pro Ala Ala Pro
            370             375             380

Leu Leu Leu Pro His Glu Ser Ser Ala Asp Cys Lys Val Gly Gly Tyr
385             390             395             400

Asn Val Pro Ala Asp Thr Met Leu Ile Val Asn Ala Tyr Ala Ile His
            405             410             415

Arg Asp Pro Ala Ala Trp Glu Asp Pro Leu Glu Phe Arg Pro Glu Arg
            420             425             430

Phe Glu Asp Gly Lys Ala Glu Gly Leu Phe Met Ile Pro Phe Gly Met
            435             440             445

Gly Arg Arg Arg Cys Pro Gly Glu Thr Leu Ala Leu Arg Thr Ile Gly
            450             455             460

Met Val Leu Ala Thr Leu Val Gln Cys Phe Asp Trp Glu Pro Val Asp
465             470             475             480

Gly Val Lys Val Asp Met Thr Glu Gly Gly Phe Thr Ile Pro Lys
            485             490             495

Ala Val Pro Leu Glu Ala Val Cys Arg Pro Arg Ala Val Met Arg Asp
```

-continued

```
                500             505             510
Val Leu Gln Asn Leu
        515

<210> SEQ ID NO 6
<211> LENGTH: 517
<212> TYPE: PRT
<213> ORGANISM: Lolium rigidum
<220> FEATURE:
<221> NAME/KEY: PEPTIDE
<222> LOCATION: (0)...(0)
<223> OTHER INFORMATION: Accession No.: AAK38079

<400> SEQUENCE: 6

Met Asp Lys Ala Tyr Ile Ala Ile Leu Ser Ser Ala Phe Leu Phe Leu
1               5                   10                  15

Val His Tyr Val Leu Gly Lys Val Ser Asp Gly Arg Arg Gly Lys Lys
            20                  25                  30

Gly Ala Val Gln Leu Pro Pro Ser Pro Pro Ala Val Pro Phe Leu Gly
        35                  40                  45

His Leu His Leu Val Glu Lys Pro Ile His Ala Thr Met Cys Arg Leu
    50                  55                  60

Ala Ala Arg Leu Gly Pro Val Phe Ser Leu Arg Leu Gly Ser Arg Arg
65                  70                  75                  80

Ala Val Val Val Ser Ser Glu Cys Ala Arg Glu Cys Phe Thr Glu
                85                  90                  95

His Asp Val Thr Phe Ala Asn Arg Pro Lys Phe Pro Ser Gln Leu Leu
            100                 105                 110

Val Ser Phe Asn Gly Thr Ala Leu Val Thr Ser Ser Tyr Gly Pro His
        115                 120                 125

Trp Arg Asn Leu Arg Arg Val Ala Thr Val Gln Leu Leu Ser Ala His
130                 135                 140

Arg Val Thr Cys Met Ser Gly Val Ile Ala Ala Glu Val Arg Ala Met
145                 150                 155                 160

Ala Arg Arg Leu Phe His Ala Ala Glu Ala Ser Pro Asp Gly Ala Ala
                165                 170                 175

Arg Val Gln Leu Lys Arg Arg Leu Phe Glu Leu Ser Leu Ser Val Leu
            180                 185                 190

Met Glu Thr Ile Ala Gln Thr Lys Ala Thr Arg Ser Glu Ala Asp Ala
        195                 200                 205

Asp Thr Asp Met Ser Leu Glu Ala Gln Glu Phe Lys Glu Val Val Asp
    210                 215                 220

Lys Leu Ile Pro His Leu Gly Ala Ala Asn Met Trp Asp Tyr Leu Pro
225                 230                 235                 240

Val Met Arg Trp Phe Asp Val Phe Gly Val Arg Ser Lys Ile Leu His
                245                 250                 255

Ala Val Ser Arg Arg Asp Ala Phe Leu Arg Arg Leu Ile Asn Ala Glu
            260                 265                 270

Arg Arg Arg Leu Ala Asp Gly Gly Ser Asp Gly Asp Lys Lys Ser Met
        275                 280                 285

Ile Ala Val Leu Leu Thr Leu Gln Lys Thr Glu Pro Lys Val Tyr Thr
    290                 295                 300

Asp Thr Met Ile Thr Ala Leu Cys Ala Asn Leu Phe Gly Ala Gly Thr
305                 310                 315                 320

Glu Thr Thr Ser Thr Thr Thr Glu Trp Ala Met Ser Leu Leu Leu Asn
                325                 330                 335
```

```
His Pro Ala Ala Leu Lys Lys Ala Gln Ala Glu Ile Asp Ala Ser Val
                340                 345                 350
Gly Thr Ser Arg Leu Val Ser Val Asp Asp Val Pro Ser Leu Ala Tyr
            355                 360                 365
Leu Gln Cys Ile Val Ser Glu Thr Leu Arg Leu Tyr Pro Ala Ala Pro
        370                 375                 380
Leu Leu Leu Pro His Glu Ser Ala Asp Cys Lys Val Gly Gly Tyr
385                 390                 395                 400
Asn Val Pro Ala Asp Thr Met Leu Ile Val Asn Ala Tyr Ala Ile His
                405                 410                 415
Arg Asp Pro Ala Ala Trp Glu Asp Pro Leu Glu Phe Lys Pro Glu Arg
            420                 425                 430
Phe Glu Asp Gly Lys Ala Glu Gly Leu Phe Met Ile Pro Phe Gly Met
        435                 440                 445
Gly Arg Arg Arg Cys Pro Gly Glu Thr Leu Ala Leu Arg Thr Ile Gly
    450                 455                 460
Met Val Leu Ala Thr Leu Val Gln Cys Phe Asp Trp Glu Pro Val Asp
465                 470                 475                 480
Gly Val Lys Val Asp Met Thr Glu Gly Gly Phe Thr Ile Pro Lys
                485                 490                 495
Ala Val Pro Leu Glu Ala Val Cys Arg Pro Arg Val Val Met Arg Asp
            500                 505                 510
Val Leu Gln Asn Leu
        515
```

<210> SEQ ID NO 7
<211> LENGTH: 517
<212> TYPE: PRT
<213> ORGANISM: Lolium rigidum
<220> FEATURE:
<221> NAME/KEY: PEPTIDE
<222> LOCATION: (0)...(0)
<223> OTHER INFORMATION: AAK38081

<400> SEQUENCE: 7

```
Met Asp Lys Ala Tyr Ile Ala Ile Leu Ser Cys Ala Phe Leu Phe Leu
 1               5                  10                  15
Val His Tyr Val Leu Gly Lys Val Ser Asp Gly Arg Arg Gly Lys Lys
                20                  25                  30
Gly Ala Val Gln Leu Pro Pro Ser Pro Ala Val Pro Phe Leu Gly
            35                  40                  45
His Leu His Leu Val Asp Lys Pro Ile His Ala Thr Met Cys Arg Leu
        50                  55                  60
Ala Ala Arg Leu Gly Pro Val Phe Ser Leu Arg Leu Gly Ser Arg Arg
65                  70                  75                  80
Ala Val Val Val Ser Ser Glu Cys Ala Arg Glu Cys Phe Thr Glu
                85                  90                  95
His Asp Val Thr Phe Ala Asn Arg Pro Lys Phe Pro Ser Gln Leu Leu
                100                 105                 110
Val Ser Phe Asn Gly Thr Ala Leu Val Thr Ser Ser Tyr Gly Pro His
            115                 120                 125
Trp Arg Asn Leu Arg Arg Val Ala Thr Val Gln Leu Leu Ser Ala His
        130                 135                 140
Arg Val Ala Cys Met Ser Gly Val Ile Ala Ala Glu Val Arg Ala Met
145                 150                 155                 160
```

Ala Arg Arg Leu Phe His Ala Glu Ala Ser Pro Asp Gly Ala Ala
            165                 170                 175

Arg Val Gln Leu Lys Arg Arg Leu Phe Glu Leu Ser Leu Ser Val Leu
        180                 185                 190

Met Glu Thr Ile Ala Gln Thr Lys Ala Thr Arg Ser Glu Ala Asp Ala
    195                 200                 205

Asp Thr Asp Met Ser Val Glu Ala Gln Glu Phe Lys Glu Val Val Asp
210                 215                 220

Lys Leu Ile Pro His Leu Gly Ala Ala Asn Met Trp Asp Tyr Leu Pro
225                 230                 235                 240

Val Met Arg Trp Phe Asp Val Phe Gly Val Arg Asn Lys Ile Leu His
                245                 250                 255

Ala Val Ser Arg Arg Asp Ala Phe Leu Arg Arg Leu Ile Asp Ala Glu
            260                 265                 270

Arg Arg Arg Leu Ala Asp Gly Gly Ser Asp Gly Asp Lys Lys Ser Met
        275                 280                 285

Ile Ala Val Leu Leu Thr Leu Gln Lys Thr Glu Pro Lys Val Tyr Thr
    290                 295                 300

Asp Thr Met Ile Thr Ala Leu Cys Ala Asn Leu Phe Gly Ala Gly Thr
305                 310                 315                 320

Glu Thr Thr Ser Thr Thr Thr Glu Trp Ala Met Ser Leu Leu Leu Asn
                325                 330                 335

His Pro Ala Ala Leu Lys Lys Ala Gln Ala Glu Ile Asp Ala Ser Val
            340                 345                 350

Gly Thr Ser Arg Leu Val Ser Val Asp Asp Val Pro Ser Leu Ala Tyr
        355                 360                 365

Leu Gln Cys Ile Val Asn Glu Thr Leu Arg Leu Tyr Pro Ala Ala Pro
    370                 375                 380

Leu Leu Leu Pro His Glu Ser Ser Ala Asp Cys Lys Val Gly Gly Tyr
385                 390                 395                 400

Asn Val Pro Ala Asp Thr Met Leu Ile Val Asn Ala Tyr Ala Ile His
                405                 410                 415

Arg Asp Pro Ala Ala Trp Glu His Pro Leu Val Phe Arg Pro Glu Arg
            420                 425                 430

Phe Glu Asp Gly Lys Ala Glu Gly Leu Phe Met Ile Pro Phe Gly Met
        435                 440                 445

Gly Arg Arg Arg Cys Pro Gly Glu Thr Leu Ala Leu Arg Thr Ile Gly
    450                 455                 460

Met Val Leu Ala Thr Leu Val Gln Cys Phe Asp Trp Glu Pro Val Asp
465                 470                 475                 480

Gly Val Asn Val Asp Met Thr Glu Gly Gly Phe Thr Ile Pro Lys
                485                 490                 495

Ala Val Pro Leu Glu Ala Val Cys Arg Pro Arg Ala Val Met Arg Asp
            500                 505                 510

Val Leu Gln Ser Ile
        515

<210> SEQ ID NO 8
<211> LENGTH: 517
<212> TYPE: PRT
<213> ORGANISM: Lolium rigidum
<220> FEATURE:
<221> NAME/KEY: PEPTIDE
<222> LOCATION: (0)...(0)
<223> OTHER INFORMATION: Accession No.: BAD27508

```
<400> SEQUENCE: 8

Met Asp Lys Ala Tyr Ile Ala Ile Leu Ser Cys Ala Phe Leu Phe Leu
  1               5                  10                  15

Val His Tyr Val Leu Gly Lys Val Ser Asp Gly Arg Arg Gly Lys Lys
             20                  25                  30

Gly Ala Val Gln Leu Pro Pro Ser Pro Ala Ile Pro Phe Ile Gly
         35                  40                  45

His Leu His Leu Val Glu Lys Pro Ile His Ala Thr Met Cys Arg Leu
     50                  55                  60

Ala Ala Arg Leu Gly Pro Val Phe Ser Leu Arg Leu Gly Ser Arg Arg
 65              70                  75                      80

Ala Val Val Val Pro Ser Ser Glu Cys Ala Arg Glu Cys Phe Thr Glu
                 85                  90                  95

His Asp Val Thr Phe Ala Asn Arg Pro Lys Phe Pro Ser Gln Leu Leu
             100                 105                 110

Ala Ser Phe Asn Gly Thr Ala Leu Val Thr Ser Ser Tyr Gly Pro His
         115                 120                 125

Trp Arg Asn Leu Arg Arg Val Ala Thr Val Gln Leu Leu Ser Ala His
    130                 135                 140

Arg Val Ala Cys Met Ser Gly Val Ile Ala Ala Glu Val Arg Ala Met
145                 150                 155                 160

Ala Arg Arg Leu Phe His Ala Glu Ala Ser Pro Asp Gly Ala Ala
                165                 170                 175

Arg Val Gln Leu Lys Arg Leu Phe Glu Leu Ser Leu Ser Val Leu
            180                 185                 190

Met Glu Thr Ile Ala Gln Thr Lys Ala Thr Arg Ser Glu Ala Asp Ala
        195                 200                 205

Asp Thr Asp Met Ser Val Glu Ala Gln Glu Phe Lys Glu Val Val Asp
210                 215                 220

Lys Leu Ile Pro His Leu Gly Ala Ala Asn Met Trp Asp Tyr Leu Pro
225                 230                 235                 240

Val Met Arg Trp Phe Asp Val Phe Gly Val Arg Asn Lys Ile Leu His
                245                 250                 255

Ala Val Ser Arg Arg Asp Ala Phe Leu Arg Arg Leu Ile Asp Ala Glu
            260                 265                 270

Arg Arg Arg Leu Ala Asp Gly Ser Asp Gly Asp Lys Lys Ser Met
        275                 280                 285

Ile Ala Val Leu Leu Thr Leu Gln Lys Thr Glu Pro Lys Val Tyr Thr
    290                 295                 300

Asp Thr Met Ile Thr Ala Leu Cys Ala Asn Leu Phe Gly Ala Gly Thr
305                 310                 315                 320

Glu Thr Thr Ser Thr Thr Glu Trp Ala Met Ser Leu Leu Leu Asn
                325                 330                 335

His Pro Ala Ala Leu Lys Lys Ala Gln Ala Glu Ile Asp Ala Ser Val
            340                 345                 350

Gly Thr Ser Arg Leu Val Ser Val Asp Asp Val Pro Ser Leu Ala Tyr
        355                 360                 365

Leu Gln Cys Ile Val Asn Glu Thr Leu Arg Leu Tyr Pro Ala Ala Pro
370                 375                 380

Leu Leu Leu Pro His Glu Ser Ser Ala Asp Cys Lys Val Gly Gly Tyr
385                 390                 395                 400

Asn Val Pro Ala Asp Thr Met Leu Ile Val Asn Ala Tyr Ala Ile His
                405                 410                 415
```

```
Arg Asp Pro Ala Ala Trp Glu His Pro Leu Glu Phe Arg Pro Glu Arg
            420                 425                 430

Phe Glu Asp Gly Lys Ala Glu Gly Leu Phe Met Ile Pro Phe Gly Val
            435                 440                 445

Gly Arg Arg Arg Cys Pro Gly Glu Thr Leu Ala Leu Arg Thr Ile Ser
            450                 455                 460

Met Val Leu Ala Thr Leu Val Gln Cys Phe Asp Trp Glu Pro Val Asp
465                 470                 475                 480

Gly Val Lys Val Asp Met Thr Glu Gly Gly Phe Thr Ile Pro Lys
            485                 490                 495

Ala Val Pro Leu Glu Ala Val Cys Arg Pro Arg Ala Val Met Arg Asp
            500                 505                 510

Val Leu Gln Asn Leu
            515

<210> SEQ ID NO 9
<211> LENGTH: 517
<212> TYPE: PRT
<213> ORGANISM: Lolium rigidum
<220> FEATURE:
<221> NAME/KEY: PEPTIDE
<222> LOCATION: (0)...(0)
<223> OTHER INFORMATION: Accession No.: BAD27507

<400> SEQUENCE: 9

Met Asp Lys Ala Tyr Ile Ala Ile Leu Ser Cys Ala Phe Leu Phe Leu
1               5                   10                  15

Val His Tyr Val Leu Gly Lys Val Ser His Gly Arg Arg Gly Lys Lys
            20                  25                  30

Gly Ala Val Gln Leu Pro Pro Ser Pro Pro Ala Ile Pro Phe Ile Gly
            35                  40                  45

His Leu His Leu Val Glu Lys Pro Ile His Ala Thr Met Cys Arg Leu
            50                  55                  60

Ala Ala Arg Leu Gly Pro Val Phe Ser Leu Arg Leu Gly Ser Arg Arg
65                  70                  75                  80

Ala Val Val Val Ser Ser Ser Glu Cys Ala Arg Glu Cys Phe Thr Glu
            85                  90                  95

His Asp Val Thr Phe Ala Asn Arg Pro Ser Ser Arg Arg Lys Leu Leu
            100                 105                 110

Ala Ser Phe Asn Gly Thr Ala Leu Val Thr Ser Ser Tyr Gly Pro His
            115                 120                 125

Trp Arg Asn Leu Arg Arg Val Ala Thr Val Gln Leu Leu Ser Ala His
            130                 135                 140

Arg Val Ala Cys Met Ser Gly Val Ile Ala Ala Glu Val Arg Ala Met
145                 150                 155                 160

Ala Arg Arg Leu Phe His Ala Ala Glu Ala Ser Pro Asp Gly Ala Thr
            165                 170                 175

Arg Val Gln Leu Lys Arg Arg Leu Phe Glu Leu Ser Leu Ser Val Leu
            180                 185                 190

Met Glu Thr Ile Ala Gln Thr Lys Ala Thr Arg Ser Glu Ala Asp Ala
            195                 200                 205

Asp Thr Asp Met Ser Val Glu Ala Gln Glu Phe Lys Glu Val Val Asp
            210                 215                 220

Lys Leu Ile Pro His Leu Gly Ala Ala Asn Met Trp Asp Tyr Leu Pro
225                 230                 235                 240
```

```
Val Met Arg Trp Phe Asp Val Phe Gly Val Arg Asn Lys Ile Leu His
                245                 250                 255

Ala Val Ser Arg Arg Asp Ala Phe Leu Arg Arg Leu Ile Asp Ala Glu
            260                 265                 270

Arg Arg Arg Leu Ala Asp Gly Gly Ser Asp Gly Asp Lys Lys Ser Met
        275                 280                 285

Ile Ala Val Leu Leu Thr Leu Gln Lys Thr Glu Pro Lys Val Tyr Thr
    290                 295                 300

Asp Thr Met Ile Thr Ala Leu Cys Ala Asn Leu Phe Gly Ala Gly Thr
305                 310                 315                 320

Glu Thr Thr Ser Thr Thr Thr Glu Trp Ala Met Ser Leu Leu Leu Asn
                325                 330                 335

His Pro Ala Ala Leu Lys Lys Ala Gln Ala Glu Ile Asp Ala Ser Val
            340                 345                 350

Gly Thr Ser Arg Leu Val Ser Val Asp Asp Val Leu Ser Leu Ala Tyr
        355                 360                 365

Leu Gln Cys Ile Val Ser Glu Thr Leu Arg Leu Tyr Pro Ala Ala Pro
    370                 375                 380

Leu Leu Leu Pro His Glu Ser Ser Ala Asp Cys Lys Val Gly Gly Tyr
385                 390                 395                 400

Asn Val Pro Ala Asp Thr Met Leu Ile Val Asn Ala Tyr Ala Ile His
                405                 410                 415

Arg Asp Pro Ala Ala Trp Glu His Pro Leu Glu Phe Arg Pro Glu Arg
            420                 425                 430

Phe Glu Asp Gly Lys Ala Glu Gly Leu Phe Met Ile Pro Phe Gly Met
        435                 440                 445

Gly Arg Arg Arg Cys Pro Gly Glu Thr Leu Ala Leu Arg Thr Ile Gly
    450                 455                 460

Met Val Leu Ala Thr Leu Val Gln Cys Phe Asp Trp Glu Pro Val Asp
465                 470                 475                 480

Gly Val Lys Val Asp Met Thr Glu Gly Gly Phe Thr Ile Pro Lys
                485                 490                 495

Ala Val Pro Leu Glu Ala Val Cys Arg Pro Arg Thr Val Met Arg Asp
            500                 505                 510

Val Leu Gln Asn Leu
        515

<210> SEQ ID NO 10
<211> LENGTH: 517
<212> TYPE: PRT
<213> ORGANISM: Lolium rigidum
<220> FEATURE:
<221> NAME/KEY: PEPTIDE
<222> LOCATION: (0)...(0)
<223> OTHER INFORMATION: Accession No.:  BAD27506

<400> SEQUENCE: 10

Met Asp Lys Ala Tyr Ile Ala Ile Leu Ser Cys Ala Phe Leu Phe Leu
  1               5                  10                  15

Val His Tyr Val Leu Gly Lys Val Ser His Gly Arg Gly Lys Lys
                 20                  25                  30

Gly Ala Val Gln Leu Pro Ser Pro Ala Ile Pro Phe Ile Gly
            35                  40                  45

His Leu His Leu Val Glu Lys Pro Ile His Ala Thr Met Cys Arg Leu
        50                  55                  60

Ala Ala Arg Leu Gly Pro Val Phe Ser Leu Arg Leu Gly Ser Arg Arg
```

```
                65                  70                  75                  80
Ala Val Val Val Ser Ser Glu Cys Ala Arg Glu Cys Phe Thr Glu
                        85                  90                  95
His Asp Val Thr Phe Ala Asn Arg Pro Lys Phe Pro Ser Gln Leu Leu
                100                 105                 110
Ala Ser Phe Asn Gly Thr Ala Leu Val Thr Pro Ser Tyr Gly Pro His
            115                 120                 125
Trp Arg Asn Leu Arg Arg Val Ala Thr Val Gln Leu Leu Ser Ala His
        130                 135                 140
Arg Val Ala Cys Met Ser Gly Val Ile Ala Ala Glu Val Arg Ala Met
145                 150                 155                 160
Ala Arg Arg Leu Phe His Ala Ala Glu Ala Ser Pro Gly Gly Ala Ala
                165                 170                 175
Arg Val Gln Leu Lys Arg Gly Pro Phe Glu Leu Ser Leu Ser Val Leu
                180                 185                 190
Met Glu Thr Ile Ala Gln Thr Lys Ala Thr Arg Ser Glu Ala Asp Ala
                195                 200                 205
Asp Thr Asp Met Ser Val Glu Ala Gln Glu Phe Lys Glu Val Val Asp
    210                 215                 220
Lys Pro Ile Pro His Leu Gly Ala Ala Asn Met Trp Asp Tyr Leu Pro
225                 230                 235                 240
Val Met Arg Trp Phe Asp Val Phe Gly Val Arg Asn Lys Ile Leu His
                245                 250                 255
Ala Val Ser Arg Arg Asp Ala Phe Leu Arg Leu Ile Asp Ala Glu
                260                 265                 270
Arg Arg Arg Leu Ala Asp Gly Gly Ser Asp Gly Asp Lys Lys Ser Met
        275                 280                 285
Ile Ala Val Leu Leu Thr Leu Gln Lys Thr Glu Pro Lys Val Tyr Thr
    290                 295                 300
Asp Thr Met Ile Thr Ala Leu Cys Ala Asn Leu Phe Gly Ala Gly Thr
305                 310                 315                 320
Glu Thr Thr Ser Thr Thr Glu Arg Ala Met Ser Leu Leu Leu Asn
                325                 330                 335
His Pro Ala Ala Leu Lys Lys Ala Gln Ala Glu Ile Asp Ala Ser Val
                340                 345                 350
Gly Thr Ser Arg Leu Val Ser Val Asp Asp Met Pro Ser Leu Ala Tyr
            355                 360                 365
Leu Gln Cys Ile Val Asn Glu Thr Leu Arg Leu Tyr Pro Ala Ala Pro
        370                 375                 380
Leu Leu Leu Pro His Glu Ser Ser Ala Asp Cys Lys Val Gly Gly Tyr
385                 390                 395                 400
Asn Val Pro Ala Asp Thr Met Leu Ile Val Asn Ala Tyr Ala Ile His
                405                 410                 415
Arg Asp Pro Ala Ala Trp Glu His Pro Leu Glu Phe Arg Pro Glu Arg
                420                 425                 430
Phe Glu Asp Gly Lys Ala Glu Gly Leu Phe Met Ile Pro Phe Gly Met
            435                 440                 445
Gly Arg Arg Arg Cys Pro Gly Glu Thr Leu Ala Leu Arg Thr Ile Gly
        450                 455                 460
Met Val Leu Ala Thr Leu Val Gln Cys Phe Asp Trp Glu Pro Val Asp
465                 470                 475                 480
Gly Val Lys Val Asp Met Thr Glu Gly Gly Phe Thr Ile Pro Lys
                485                 490                 495
```

Ala Val Pro Leu Glu Ala Val Cys Arg Pro Arg Ala Val Met Arg Asp
            500                 505                 510

Val Leu Gln Asn Leu
        515

<210> SEQ ID NO 11
<211> LENGTH: 512
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Accession No.: XP_469849

<400> SEQUENCE: 11

Met Asp Lys Ala Tyr Ile Ala Val Phe Ser Ile Val Ile Leu Phe Leu
 1               5                   10                  15

Leu Val Asp Tyr Leu Arg Arg Leu Arg Gly Gly Gly Thr Ser Asn Gly
            20                  25                  30

Lys Asn Lys Gly Met Arg Leu Pro Pro Gly Leu Pro Ala Val Pro Ile
        35                  40                  45

Ile Gly His Leu His Leu Val Lys Lys Pro Met His Ala Thr Leu Ser
    50                  55                  60

Arg Leu Ala Ala Arg His Gly Pro Val Phe Ser Leu Arg Leu Gly Ser
65                  70                  75                  80

Arg Arg Ala Val Val Ser Ser Pro Gly Cys Ala Arg Glu Cys Phe
                85                  90                  95

Thr Glu His Asp Val Ala Phe Ala Asn Arg Pro Arg Phe Glu Ser Gln
                100                 105                 110

Leu Leu Met Ser Phe Asp Gly Thr Ala Leu Ala Met Ala Ser Tyr Gly
            115                 120                 125

Pro His Trp Arg Asn Leu Arg Arg Val Ala Ala Val Gln Leu Leu Ser
        130                 135                 140

Ala Arg Arg Val Gly Leu Met Ser Gly Leu Ile Ala Gly Glu Val Arg
145                 150                 155                 160

Ala Met Val Arg Ser Leu Cys Arg Arg Pro Ala Ala Ala Pro Val
                165                 170                 175

Gln Leu Lys Arg Arg Leu Phe Glu Leu Ser Leu Ser Val Leu Met Glu
            180                 185                 190

Thr Ile Ala Gln Ser Lys Ala Thr Arg Pro Glu Thr Thr Asp Thr Asp
        195                 200                 205

Thr Asp Met Ser Met Glu Ala Gln Glu Tyr Lys Gln Val Val Glu Glu
    210                 215                 220

Ile Leu Glu Arg Ile Gly Thr Gly Asn Leu Cys Asp Tyr Leu Pro Ala
225                 230                 235                 240

Leu Arg Trp Phe Asp Val Phe Gly Val Arg Asn Arg Ile Leu Ala Ala
                245                 250                 255

Val Ser Arg Arg Asp Ala Phe Leu Arg Arg Leu Ile Tyr Ala Ala Arg
            260                 265                 270

Trp Arg Met Asp Asp Gly Glu Lys Lys Ser Met Ile Ala Val Leu Leu
        275                 280                 285

Thr Leu Gln Lys Thr Gln Pro Glu Val Tyr Thr Asp Asn Met Ile Thr
    290                 295                 300

Ala Leu Cys Ser Asn Leu Leu Gly Ala Gly Thr Glu Thr Thr Ser Thr
305                 310                 315                 320

-continued

```
Thr Ile Glu Trp Ala Met Ser Leu Leu Leu Asn His Pro Glu Thr Leu
            325                 330                 335

Lys Lys Ala Gln Ala Glu Ile Asp Ala Ser Val Gly Asn Ser Arg Leu
            340                 345                 350

Ile Thr Ala Asp Asp Val Pro Arg Ile Thr Tyr Leu Gln Cys Ile Val
            355                 360                 365

Arg Glu Thr Leu Arg Leu Tyr Pro Ala Ala Pro Met Leu Ile Pro His
370                 375                 380

Glu Ser Ser Ala Asp Cys Glu Val Gly Gly Tyr Ser Val Pro Arg Gly
385                 390                 395                 400

Thr Met Leu Leu Val Asn Ala Tyr Ala Ile His Arg Asp Pro Ala Ala
            405                 410                 415

Trp Glu Glu Pro Glu Arg Phe Val Pro Glu Arg Phe Glu Gly Gly Gly
            420                 425                 430

Cys Asp Gly Asn Leu Ser Met Pro Phe Gly Met Gly Arg Arg Arg Cys
            435                 440                 445

Pro Gly Glu Thr Leu Ala Leu His Thr Val Gly Leu Val Leu Gly Thr
450                 455                 460

Leu Ile Gln Cys Phe Asp Trp Glu Arg Val Asp Gly Val Glu Val Asp
465                 470                 475                 480

Met Ala Glu Gly Gly Leu Thr Met Pro Lys Val Val Pro Leu Glu
            485                 490                 495

Ala Val Cys Arg Pro Arg Asp Ala Met Gly Gly Val Leu Arg Glu Leu
            500                 505                 510
```

<210> SEQ ID NO 12
<211> LENGTH: 527
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Accession No.: XP_469851

<400> SEQUENCE: 12

```
Met Asp Lys Ala Tyr Ile Ala Val Phe Ser Ile Ala Ile Leu Phe Leu
1               5                   10                  15

Leu Val Asp Tyr Phe Arg Cys Arg Arg Arg Gly Ser Gly Ser Asn
            20                  25                  30

Asn Gly Glu Asn Lys Gly Met Leu Gln Leu Pro Pro Ser Pro Ala
            35                  40                  45

Ile Pro Phe Phe Gly His Leu His Leu Ile Asp Lys Pro Leu His Ala
50                  55                  60

Ala Leu Ser Arg Leu Ala Glu Arg His Gly Pro Val Phe Ser Leu Arg
65                  70                  75                  80

Leu Gly Ser Arg Asn Ala Val Val Val Ser Ser Pro Glu Cys Ala Arg
            85                  90                  95

Glu Cys Phe Thr Asp Asn Asp Val Cys Phe Ala Asn Arg Pro Gln Phe
            100                 105                 110

Pro Ser Gln Met Pro Ala Thr Phe Tyr Gly Ala Gly Phe Gly Phe Ala
            115                 120                 125

Asn Tyr Gly Ala His Trp Arg Asn Leu Arg Arg Ile Ala Thr Val His
130                 135                 140

Leu Leu Ser Ala His Arg Val Arg Gly Met Ala Gly Val Val Ser Gly
145                 150                 155                 160

Glu Ile Arg Pro Met Val Gln Arg Met Tyr Arg Ala Ala Ala Ala Ala
```

```
                165                 170                 175
Gly Val Gly Val Ala Arg Val Gln Leu Lys Arg Arg Leu Phe Glu Leu
            180                 185                 190

Ser Leu Ser Val Leu Met Glu Ala Ile Ala Gln Thr Lys Thr Thr Arg
            195                 200                 205

Pro Glu Ala Asp Asp Ala Asp Thr Asp Met Ser Val Glu Ala Gln Glu
            210                 215                 220

Phe Lys Asn Val Leu Asp Glu Leu Asn Pro Leu Leu Gly Ala Ala Asn
225                 230                 235                 240

Leu Trp Asp Tyr Leu Pro Ala Leu Arg Val Phe Asp Val Leu Gly Val
                245                 250                 255

Lys Arg Lys Ile Ala Thr Leu Ala Asn Arg Arg Asp Ala Phe Val Arg
                260                 265                 270

Arg Leu Ile Asp Ala Glu Arg Gln Arg Met Asp Asn Gly Val Asp Gly
            275                 280                 285

Gly Asp Asp Gly Glu Lys Lys Ser Val Ile Ser Val Leu Leu Ser Leu
            290                 295                 300

Gln Lys Thr Glu Pro Glu Val Tyr Lys Asp Ile Val Ile Val Asn Leu
305                 310                 315                 320

Cys Ala Ala Leu Phe Ala Ala Gly Thr Glu Thr Thr Ala Met Thr Ile
                325                 330                 335

Glu Trp Ala Met Ser Leu Leu Leu Asn His Pro Lys Ile Leu Lys Lys
                340                 345                 350

Ala Lys Ala Glu Ile Asp Ala Ser Val Gly Asn Ser Arg Leu Ile Asn
            355                 360                 365

Gly Asp Asp Met Pro His Leu Ser Tyr Leu Gln Cys Ile Ile Asn Glu
            370                 375                 380

Thr Leu Arg Leu Tyr Pro Val Ala Pro Leu Leu Ile Pro His Glu Ser
385                 390                 395                 400

Ser Ala Asp Cys Lys Val Asn Gly Tyr His Ile Pro Ser Gly Thr Met
                405                 410                 415

Leu Leu Val Asn Val Ile Ala Ile Gln Arg Asp Pro Met Val Trp Lys
                420                 425                 430

Glu Pro Asn Glu Phe Lys Pro Glu Arg Phe Glu Asn Gly Glu Ser Glu
            435                 440                 445

Gly Leu Phe Met Ile Pro Phe Gly Met Gly Arg Arg Lys Cys Pro Gly
            450                 455                 460

Glu Thr Met Ala Leu Gln Thr Ile Gly Leu Val Leu Gly Ala Leu Ile
465                 470                 475                 480

Gln Cys Phe Asp Trp Asp Arg Val Asp Gly Ala Glu Val Asp Met Thr
                485                 490                 495

Gln Gly Ser Gly Leu Thr Asn Pro Arg Ala Val Pro Leu Glu Ala Met
            500                 505                 510

Cys Lys Pro Arg Glu Ala Met Ser Asp Val Phe Arg Glu Leu Leu
            515                 520                 525

<210> SEQ ID NO 13
<211> LENGTH: 518
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Accession No.: XP_469852

<400> SEQUENCE: 13
```

```
Met Val Lys Ala Tyr Ile Ala Ile Phe Ser Ile Ala Val Leu Leu Leu
 1               5                  10                  15

Ile His Phe Leu Phe Arg Arg Gly Arg Ser Asn Gly Met Pro Leu
             20                  25                  30

Pro Pro Ser Pro Pro Ala Ile Pro Phe Gly His Leu His Leu Ile
             35                  40                  45

Asp Lys Pro Phe His Ala Ala Leu Ser Arg Leu Ala Glu Arg His Gly
 50                  55                  60

Pro Val Phe Ser Leu Arg Leu Gly Ser Arg Asn Ala Val Val Ser
 65                  70                  75                  80

Ser Pro Glu Cys Ala Arg Glu Cys Phe Thr Asp Asn Asp Val Cys Phe
                 85                  90                  95

Ala Asn Arg Pro Arg Phe Pro Ser Gln Met Leu Ala Thr Phe Asn Gly
             100                 105                 110

Thr Ser Leu Gly Ser Ala Asn Tyr Gly Pro His Trp Arg Asn Leu Arg
             115                 120                 125

Arg Ile Ala Thr Val His Leu Leu Ser Ser His Arg Val Ser Gly Met
 130                 135                 140

Ser Gly Ile Ile Ser Gly Gln Ala Arg His Met Val Arg Arg Met Tyr
145                 150                 155                 160

Arg Ala Ala Thr Ala Ser Ala Ala Gly Val Ala Arg Val Gln Leu Asn
                 165                 170                 175

Arg Arg Leu Phe Glu Leu Ser Leu Ser Val Leu Met Glu Ala Ile Ala
             180                 185                 190

Gln Ser Lys Thr Thr Arg Arg Glu Ala Pro Asp Ala Asp Thr Asp Met
             195                 200                 205

Ser Met Glu Ala Gln Glu Leu Arg His Val Leu Asp Glu Leu Asn Pro
210                 215                 220

Leu Ile Gly Ala Ala Asn Leu Trp Asp Tyr Leu Pro Ala Leu Arg Trp
225                 230                 235                 240

Phe Asp Val Phe Gly Val Lys Arg Lys Ile Val Ala Ala Val Asn Arg
                 245                 250                 255

Arg Asn Ala Phe Met Arg Arg Leu Ile Asp Ala Glu Arg Gln Arg Met
             260                 265                 270

Asp Asn Asn Asp Val Asp Gly Gly Asp Gly Glu Lys Lys Ser Met
             275                 280                 285

Ile Ser Val Leu Leu Thr Leu Gln Lys Thr Gln Pro Glu Val Tyr Thr
 290                 295                 300

Asp Thr Leu Ile Met Thr Leu Cys Ala Pro Leu Phe Gly Ala Gly Thr
305                 310                 315                 320

Glu Thr Thr Ser Thr Thr Ile Glu Trp Ala Met Ser Leu Leu Leu Asn
                 325                 330                 335

His Pro Glu Ile Leu Lys Lys Ala Gln Ala Glu Ile Asp Met Ser Val
             340                 345                 350

Gly Asn Ser Arg Leu Ile Ser Val Val Asp Val His Arg Leu Gly Tyr
             355                 360                 365

Leu Gln Cys Ile Ile Asn Glu Thr Leu Arg Met Tyr Pro Ala Ala Pro
 370                 375                 380

Leu Leu Leu Pro His Glu Ser Ser Ala Asp Cys Lys Val Gly Gly Tyr
385                 390                 395                 400

His Ile Pro Ser Gly Ala Met Leu Leu Val Asn Val Ala Ala Ile Gln
                 405                 410                 415
```

Arg Asp Pro Val Ile Trp Lys Glu Pro Ser Glu Phe Lys Pro Glu Arg
            420                 425                 430

Phe Glu Asn Gly Arg Phe Glu Gly Leu Phe Met Ile Pro Phe Gly Met
        435                 440                 445

Gly Arg Arg Arg Cys Pro Gly Glu Met Leu Ala Leu Gln Thr Ile Gly
    450                 455                 460

Leu Val Leu Gly Thr Met Ile Gln Cys Phe Asp Trp Gly Arg Val Asp
465                 470                 475                 480

Asp Ala Met Val Asp Met Thr Gln Ser Asn Gly Leu Thr Ser Leu Lys
                485                 490                 495

Val Ile Pro Leu Glu Ala Met Cys Lys Pro Arg Glu Ala Met Cys Asp
            500                 505                 510

Val Leu Arg Lys Phe Met
        515

<210> SEQ ID NO 14
<211> LENGTH: 10
<212> TYPE: PRT
<213> ORGANISM: Artificial Sequence
<220> FEATURE:
<223> OTHER INFORMATION: Motif common to all Cytochrome P450
      sequences
<221> NAME/KEY: VARIANT
<222> LOCATION: 2, 3, 5, 6, 7, 9
<223> OTHER INFORMATION: Xaa = Any Amino Acid

<400> SEQUENCE: 14

Phe Xaa Xaa Gly Xaa Xaa Xaa Cys Xaa Gly
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Motif common to all Cytochrome P450
      sequences
<221> NAME/KEY: VARIANT
<222> LOCATION: (1)...(1)
<223> OTHER INFORMATION: Xaa = Ala or Gly
<221> NAME/KEY: VARIANT
<222> LOCATION: (3)...(3)
<223> OTHER INFORMATION: Xaa = any amino acid
<221> NAME/KEY: VARIANT
<222> LOCATION: (4)...(4)
<223> OTHER INFORMATION: Xaa = Asp or Glu
<221> NAME/KEY: VARIANT
<222> LOCATION: (6)...(6)
<223> OTHER INFORMATION: Xaa = Thr or Ser

<400> SEQUENCE: 15

Xaa Gly Xaa Xaa Thr Xaa
1               5

<210> SEQ ID NO 16
<211> LENGTH: 1859
<212> TYPE: DNA
<213> ORGANISM: Zea mays
<220> FEATURE:
<221> NAME/KEY: misc_feature
<222> LOCATION: (0)...(0)
<223> OTHER INFORMATION: Maize B73 genomic sequence for Nsf1 gene
<221> NAME/KEY: intron
<222> LOCATION: (946)...(1238)
<223> OTHER INFORMATION: intron

<400> SEQUENCE: 16

```
atggataagg cctacatcgc cgccctctcc gccgccgccc tcttcttgct ccactacctc    60
ctgggccgcc gggccggcgg cgagggcaag gccaaggcca agggctcgcg gcggcggctc   120
ccgccgagcc ctccggcgat cccgttcctg ggccacctcc acctcgtcaa ggccccgttc   180
cacggggcgc tggcccgcct cgcggcgcgc acggcccggg tgttctccat cgcgctgggg   240
acccggcgcg ccgtggtcgt gtcgtcgccg gactgcgcca gggagtgctt cacggagcac   300
gacgtgaact cgcgaaccg gccgctgttc cgtcgatgc ggctggcgtc cttcgacggc   360
gccatgctct ccgtgtccag ctacggcccg tactggcgca acctgcgccg cgtcgccgcc   420
gtgcagctcc tctccgcgca ccgcgtcggg tgcatggccc cgccatcga agcgcaggtg   480
cgcgccatgg tgcggaggat ggaccgcgcc gccgcggccg gcggcggcgg cgtcgcgcgc   540
gtccagctca gcggcggct gttcgagctc tccctcagcg tgctcatgga gaccatcgcg   600
cacaccaaga cgtcccgcgc cgaggccgac gccgactcgg acatgtcgac cgaggcccac   660
gagttcaagc agatcgtcga cgagctcgtg ccgtacatcg gcacggccaa ccgctgggac   720
tacctgccgg tgctgcgctg gttcgacgtg ttcggcgtga ggaacaagat cctcgacgcc   780
gtgggcagaa gggacgcgtt cctggggcgg ctcatcgacg gggagcggcg gaggctggac   840
gctggcgacg agagcgaaag taagagcatg attgcggtgc tgctcactct gcagaagtcc   900
gagccagagg tctacactga cactgtgatc actgctcttt gcgcggtgag tgcttcttct   960
tctaccatac gtcactctct tatcctcaca aaatacaaaa aaagttgccc gttttctcag  1020
tttagtcgtc aacactccgg actctactat ccgccaaagt ataggattcg ctaaaaattt  1080
aggtgtcttt tttaatacta aaattagata ttgaatttgt tgtgctttat gttgacatag  1140
tctgtaattc ttttttcccg aggataaaaa atgttagaca tggatctgga tatttgaacc  1200
atgagaaaga ctgactgcaa ttttgttctg tgataaagaa cctattcggc gccggaacgg  1260
agaccacgtc caccacgacg gaatgggcca tgtcactgct gctgaaccac cgggaggcgc  1320
tcaagaaggc gcaggccgag atcgacgcgg cggtgggcac ctcccgcctg gtgaccgcgg  1380
acgacgtgcc ccacctcacc tacctgcagt gcatcgtcga cgagacgctg cgcctgcacc  1440
cggccgcgcc gctgctgctg ccgcacgagt ccgccgcgga ctgcacggtc ggcggctacg  1500
acgtgccgcg cggcacgatg ctgctggtca cgtgcacgc ggtccacagg accccgcgg  1560
tgtgggagga cccggacagg ttcgtgccgg agcggttcga gggcgccggc ggcaaggccg  1620
aggggcgcct gctgatgccg ttcgggatgg ggcggcgcaa gtgccccggg agacgctcg  1680
cgctgcggac cgtcgggctg gtgctcgcca cgctgctcca gtgcttcgac tgggacacgg  1740
ttgatggagc tcaggttgac atgaaggcta gcggcgggct gaccatgccc cgggccgtcc  1800
cgttggaggc catgtgcagg ccgcgtacag ctatgcgtgg tgttcttaag aggctctga   1859
```

<210> SEQ ID NO 17
<211> LENGTH: 1566
<212> TYPE: DNA
<213> ORGANISM: Zea mays
<220> FEATURE:
<221> NAME/KEY: misc_feature
<222> LOCATION: (0)...(0)
<223> OTHER INFORMATION: Q66 maize line ORF for Nsf1
<221> NAME/KEY: CDS
<222> LOCATION: (1)...(1566)

<400> SEQUENCE: 17

```
atg gat aag gcc tac atc gcc gcc ctc tcc gcc gcc gcc ctc ttc ttg     48
Met Asp Lys Ala Tyr Ile Ala Ala Leu Ser Ala Ala Ala Leu Phe Leu
1               5                   10                  15
```

| | | |
|---|---|---|
| ctc cac tac ctc ctg ggc cgg cgg gcc ggc ggc gag ggc aag gcc aag<br>Leu His Tyr Leu Leu Gly Arg Arg Ala Gly Gly Glu Gly Lys Ala Lys<br>20 25 30 | | 96 |
| gcc aag ggc tcg cgg cgg cgg ctc ccg ccg agc cct ccg gcg atc ccg<br>Ala Lys Gly Ser Arg Arg Arg Leu Pro Pro Ser Pro Pro Ala Ile Pro<br>35 40 45 | | 144 |
| ttc ctg ggc cac ctc cac ctc gtc aag gcc ccg ttc cac ggg gcg ctg<br>Phe Leu Gly His Leu His Leu Val Lys Ala Pro Phe His Gly Ala Leu<br>50 55 60 | | 192 |
| gcc cgc ctc gcg gcg cgc cac ggc ccg gtg ttc tcc atg cgc ctg ggg<br>Ala Arg Leu Ala Ala Arg His Gly Pro Val Phe Ser Met Arg Leu Gly<br>65 70 75 80 | | 240 |
| acc cgg cgc gcc gtg gtc gtg tcg tcg ccg gac tgc gcc agg gag tgc<br>Thr Arg Arg Ala Val Val Val Ser Ser Pro Asp Cys Ala Arg Glu Cys<br>85 90 95 | | 288 |
| ttc acg gag cac gac gtg aac ttc gcg aac cgg ccg ctg ttc ccg tcg<br>Phe Thr Glu His Asp Val Asn Phe Ala Asn Arg Pro Leu Phe Pro Ser<br>100 105 110 | | 336 |
| atg cgg ctg gcg tcc ttc gac ggc gcc atg ctc tcc gtg tcc agc tac<br>Met Arg Leu Ala Ser Phe Asp Gly Ala Met Leu Ser Val Ser Ser Tyr<br>115 120 125 | | 384 |
| ggc ccg tac tgg cgc aac ctg cgc cgc gtc gcc gcc gtg cag ctc ctc<br>Gly Pro Tyr Trp Arg Asn Leu Arg Arg Val Ala Ala Val Gln Leu Leu<br>130 135 140 | | 432 |
| tcc gcg cac cgc gtc ggg tgc atg gcc ccc gcc atc gaa gcg cag gtg<br>Ser Ala His Arg Val Gly Cys Met Ala Pro Ala Ile Glu Ala Gln Val<br>145 150 155 160 | | 480 |
| cgc gcc atg gtg cgg agg atg gac cgc gcc gcc gcg gcc ggc ggc ggc<br>Arg Ala Met Val Arg Arg Met Asp Arg Ala Ala Ala Ala Gly Gly Gly<br>165 170 175 | | 528 |
| ggc gtc gcg cgc gtc cag ctc aag cgg cgg ctg ttc gag ctc tcc ctc<br>Gly Val Ala Arg Val Gln Leu Lys Arg Arg Leu Phe Glu Leu Ser Leu<br>180 185 190 | | 576 |
| agc gtg ctc atg gag acc atc gcg cac acc aag acg tcc cgc gcc gag<br>Ser Val Leu Met Glu Thr Ile Ala His Thr Lys Thr Ser Arg Ala Glu<br>195 200 205 | | 624 |
| gcc gac gcc aac tcg gac atg tcg acc gag gcc cac gag ttc aag cag<br>Ala Asp Ala Asn Ser Asp Met Ser Thr Glu Ala His Glu Phe Lys Gln<br>210 215 220 | | 672 |
| atc gtc aac gag ctc gtg ccg tac atc ggc acg gcc aac cgc tgg gac<br>Ile Val Asn Glu Leu Val Pro Tyr Ile Gly Thr Ala Asn Arg Trp Asp<br>225 230 235 240 | | 720 |
| tac ctg ccg gtg ctg cgc tgg ttc gac gtg ttc ggc gtg agg aac aag<br>Tyr Leu Pro Val Leu Arg Trp Phe Asp Val Phe Gly Val Arg Asn Lys<br>245 250 255 | | 768 |
| atc ctc gac gcc gtg ggc aga agg gac gcg ttc ctg ggg cgg ctc atc<br>Ile Leu Asp Ala Val Gly Arg Arg Asp Ala Phe Leu Gly Arg Leu Ile<br>260 265 270 | | 816 |
| gac ggg gag cgg cgg agg ctg gac gct ggc gac gag agc gaa agt aag<br>Asp Gly Glu Arg Arg Arg Leu Asp Ala Gly Asp Glu Ser Glu Ser Lys<br>275 280 285 | | 864 |
| agc atg att gcg gtg ctg ctc act ctg cag aag tcc gag cca gag gtc<br>Ser Met Ile Ala Val Leu Leu Thr Leu Gln Lys Ser Glu Pro Glu Val<br>290 295 300 | | 912 |
| tac act gac act gtg atc act gct ctt tgc gcg aac cta ttc ggc gcc<br>Tyr Thr Asp Thr Val Ile Thr Ala Leu Cys Ala Asn Leu Phe Gly Ala<br>305 310 315 320 | | 960 |
| gga acg gag acc acg tcc acc acg acg gaa tgg gcc atg tca ctg ctg<br>Gly Thr Glu Thr Thr Ser Thr Thr Thr Glu Trp Ala Met Ser Leu Leu | | 1008 |

```
                     325                 330                 335
ctg aac cac cgg gag gcg ctc aag aag gcg cag gcc gag atc gac gcg      1056
Leu Asn His Arg Glu Ala Leu Lys Lys Ala Gln Ala Glu Ile Asp Ala
            340                 345                 350 gcg gtg ggc gcc tcc cgc ctg gtg acc gcg gac gac gtg ccc cac ctc      1104
Ala Val Gly Ala Ser Arg Leu Val Thr Ala Asp Asp Val Pro His Leu
        355                 360                 365 acc tac ctg cag tgc atc gtc gac gag acg ctg cgc ctg cac ccg gcc      1152
Thr Tyr Leu Gln Cys Ile Val Asp Glu Thr Leu Arg Leu His Pro Ala
    370                 375                 380 gcg ccg ctg ctg ctg ccg cac gag tcc gcc gcg gac tgc acg gtc ggc      1200
Ala Pro Leu Leu Leu Pro His Glu Ser Ala Ala Asp Cys Thr Val Gly
385                 390                 395                 400 ggc tac gac gtg ccg cgc ggc acg atg ctg ctg gtc aac gtg cac gcg      1248
Gly Tyr Asp Val Pro Arg Gly Thr Met Leu Leu Val Asn Val His Ala
                405                 410                 415 gtc cac agg gac ccc gcg gtg tgg gag gac ccg gac agg ttc gtg ccg      1296
Val His Arg Asp Pro Ala Val Trp Glu Asp Pro Asp Arg Phe Val Pro
            420                 425                 430 gag cgg ttc gag ggc gcc ggc ggc aag gcc gag ggg cgc ctg ctg atg      1344
Glu Arg Phe Glu Gly Ala Gly Gly Lys Ala Glu Gly Arg Leu Leu Met
        435                 440                 445 ccg ttc ggg atg ggg cgg cgc aag tgc ccc ggg gag acg ctc gcg ctg      1392
Pro Phe Gly Met Gly Arg Arg Lys Cys Pro Gly Glu Thr Leu Ala Leu
    450                 455                 460 cgg acc gtc ggg ctg gtg ctc gcc acg ctg ctc cag tgc ttc gac tgg      1440
Arg Thr Val Gly Leu Val Leu Ala Thr Leu Leu Gln Cys Phe Asp Trp
465                 470                 475                 480 gac acg gtt gat gga gct cag gtt gac atg aag gct agc ggg ggg ctg      1488
Asp Thr Val Asp Gly Ala Gln Val Asp Met Lys Ala Ser Gly Gly Leu
                485                 490                 495 acc atg ccc cgg gcc gtc ccg ttg gag gcc atg tgc agg ccg cgt aca      1536
Thr Met Pro Arg Ala Val Pro Leu Glu Ala Met Cys Arg Pro Arg Thr
            500                 505                 510 gct atg cgt ggt gtt ctt aag agg ctc tga                              1566
Ala Met Arg Gly Val Leu Lys Arg Leu *
        515                 520

<210> SEQ ID NO 18
<211> LENGTH: 521
<212> TYPE: PRT
<213> ORGANISM: Zea mays
<220> FEATURE:
<221> NAME/KEY: PEPTIDE
<222> LOCATION: (0)...(0)
<223> OTHER INFORMATION: Q66 maize line Nsf1 peptide

<400> SEQUENCE: 18

Met Asp Lys Ala Tyr Ile Ala Ala Leu Ser Ala Ala Ala Leu Phe Leu
 1               5                  10                  15

Leu His Tyr Leu Leu Gly Arg Arg Ala Gly Gly Glu Gly Lys Ala Lys
            20                  25                  30

Ala Lys Gly Ser Arg Arg Leu Pro Pro Ser Pro Pro Ala Ile Pro
        35                  40                  45

Phe Leu Gly His Leu His Leu Val Lys Ala Pro Phe His Gly Ala Leu
    50                  55                  60

Ala Arg Leu Ala Ala Arg His Gly Pro Val Phe Ser Met Arg Leu Gly
65                  70                  75                  80

Thr Arg Arg Ala Val Val Val Ser Ser Pro Asp Cys Ala Arg Glu Cys
                85                  90                  95
```

```
Phe Thr Glu His Asp Val Asn Phe Ala Asn Arg Pro Leu Phe Pro Ser
            100                 105                 110

Met Arg Leu Ala Ser Phe Asp Gly Ala Met Leu Ser Val Ser Ser Tyr
        115                 120                 125

Gly Pro Tyr Trp Arg Asn Leu Arg Arg Val Ala Ala Val Gln Leu Leu
    130                 135                 140

Ser Ala His Arg Val Gly Cys Met Ala Pro Ala Ile Glu Ala Gln Val
145                 150                 155                 160

Arg Ala Met Val Arg Arg Met Asp Arg Ala Ala Ala Gly Gly Gly
                165                 170                 175

Gly Val Ala Arg Val Gln Leu Lys Arg Arg Leu Phe Glu Leu Ser Leu
                180                 185                 190

Ser Val Leu Met Glu Thr Ile Ala His Thr Lys Thr Ser Arg Ala Glu
        195                 200                 205

Ala Asp Ala Asn Ser Asp Met Ser Thr Glu Ala His Glu Phe Lys Gln
210                 215                 220

Ile Val Asn Glu Leu Val Pro Tyr Ile Gly Thr Ala Asn Arg Trp Asp
225                 230                 235                 240

Tyr Leu Pro Val Leu Arg Trp Phe Asp Val Phe Gly Val Arg Asn Lys
                245                 250                 255

Ile Leu Asp Ala Val Gly Arg Arg Asp Ala Phe Leu Gly Arg Leu Ile
            260                 265                 270

Asp Gly Glu Arg Arg Arg Leu Asp Ala Gly Asp Glu Ser Glu Ser Lys
                275                 280                 285

Ser Met Ile Ala Val Leu Leu Thr Leu Gln Lys Ser Glu Pro Glu Val
        290                 295                 300

Tyr Thr Asp Thr Val Ile Thr Ala Leu Cys Ala Asn Leu Phe Gly Ala
305                 310                 315                 320

Gly Thr Glu Thr Thr Ser Thr Thr Thr Glu Trp Ala Met Ser Leu Leu
                325                 330                 335

Leu Asn His Arg Glu Ala Leu Lys Lys Ala Gln Ala Glu Ile Asp Ala
            340                 345                 350

Ala Val Gly Ala Ser Arg Leu Val Thr Ala Asp Asp Val Pro His Leu
        355                 360                 365

Thr Tyr Leu Gln Cys Ile Val Asp Glu Thr Leu Arg Leu His Pro Ala
    370                 375                 380

Ala Pro Leu Leu Leu Pro His Glu Ser Ala Ala Asp Cys Thr Val Gly
385                 390                 395                 400

Gly Tyr Asp Val Pro Arg Gly Thr Met Leu Leu Val Asn Val His Ala
                405                 410                 415

Val His Arg Asp Pro Ala Val Trp Glu Asp Pro Asp Arg Phe Val Pro
            420                 425                 430

Glu Arg Phe Glu Gly Ala Gly Gly Lys Ala Glu Gly Arg Leu Leu Met
        435                 440                 445

Pro Phe Gly Met Gly Arg Arg Lys Cys Pro Gly Glu Thr Leu Ala Leu
    450                 455                 460

Arg Thr Val Gly Leu Val Leu Ala Thr Leu Leu Gln Cys Phe Asp Trp
465                 470                 475                 480

Asp Thr Val Asp Gly Ala Gln Val Asp Met Lys Ala Ser Gly Gly Leu
                485                 490                 495

Thr Met Pro Arg Ala Val Pro Leu Glu Ala Met Cys Arg Pro Arg Thr
            500                 505                 510
```

-continued

```
Ala Met Arg Gly Val Leu Lys Arg Leu
        515                 520

<210> SEQ ID NO 19
<211> LENGTH: 1566
<212> TYPE: DNA
<213> ORGANISM: Zea mays
<220> FEATURE:
<221> NAME/KEY: misc_feature
<222> LOCATION: (0)...(0)
<223> OTHER INFORMATION: Black Mexican Sweet (BMS) maize line ORF for
      Nsf1
<221> NAME/KEY: CDS
<222> LOCATION: (1)...(1566)

<400> SEQUENCE: 19 atg gat aag gcc tac atc gcc gcc ctc tcc gcc gcc gcc ctc ttc ttg      48
Met Asp Lys Ala Tyr Ile Ala Ala Leu Ser Ala Ala Ala Leu Phe Leu
1               5                   10                  15 ctc cac tac ctc ctg ggc cgg cgg gcc ggc ggc gag ggc aag gcc aag      96
Leu His Tyr Leu Leu Gly Arg Arg Ala Gly Gly Glu Gly Lys Ala Lys
            20                  25                  30 gcc aag ggc tcg cgg cgg cgg ctc ccg ccg agc cct ccg gcg atc ccg     144
Ala Lys Gly Ser Arg Arg Arg Leu Pro Pro Ser Pro Pro Ala Ile Pro
        35                  40                  45 ttc ctg ggc cac ctc cac ctc gtc aag gcc ccg ttc cac ggg gcg ctg     192
Phe Leu Gly His Leu His Leu Val Lys Ala Pro Phe His Gly Ala Leu
    50                  55                  60 gcc cgc ctc gcg gcg cgc cac ggc ccg gtg ttc tcc atg cgc ctg ggg     240
Ala Arg Leu Ala Ala Arg His Gly Pro Val Phe Ser Met Arg Leu Gly
65                  70                  75                  80 acc cgg cgc gcc gtg gtc gtg tcg tcg ccg gac tgc gcc agg gag tgc     288
Thr Arg Arg Ala Val Val Val Ser Ser Pro Asp Cys Ala Arg Glu Cys
                85                  90                  95 ttc acg gag cac gac gtg aac ttc gcg aac cgg ccg ctg ttc ccg tcg     336
Phe Thr Glu His Asp Val Asn Phe Ala Asn Arg Pro Leu Phe Pro Ser
            100                 105                 110 atg cgg ctg gcg tcc ttc gac ggc gcc atg ctc tcc gtg tcc agc tac     384
Met Arg Leu Ala Ser Phe Asp Gly Ala Met Leu Ser Val Ser Ser Tyr
        115                 120                 125 ggc ccg tac tgg cgc aac ctg cgc cgc gtc gcc gcc gtg cag ctc ctc     432
Gly Pro Tyr Trp Arg Asn Leu Arg Arg Val Ala Ala Val Gln Leu Leu
    130                 135                 140 tcc gcg cac cgc gtc ggg tgc atg gcc ccc gcc atc gaa gcg cag gtg     480
Ser Ala His Arg Val Gly Cys Met Ala Pro Ala Ile Glu Ala Gln Val
145                 150                 155                 160 cgc gcc atg gtg cgg agg atg gac cgc gcc gcc gcg gcc ggc ggc ggc     528
Arg Ala Met Val Arg Arg Met Asp Arg Ala Ala Ala Ala Gly Gly Gly
                165                 170                 175 ggc gtc gcg cgc gtc cag ctc aag cgg cgg ctg ttc gag ctc tcc ctc     576
Gly Val Ala Arg Val Gln Leu Lys Arg Arg Leu Phe Glu Leu Ser Leu
            180                 185                 190 agc gtg ctc atg gag acc atc gcg cac acc aag acg tcc cgc gcc gag     624
Ser Val Leu Met Glu Thr Ile Ala His Thr Lys Thr Ser Arg Ala Glu
        195                 200                 205 gcc gac gcc gac tcg gac atg tcg acc gag gcc cac gag ttc aag cag     672
Ala Asp Ala Asp Ser Asp Met Ser Thr Glu Ala His Glu Phe Lys Gln
    210                 215                 220 atc gtc gac gag ctc gtg ccg tac atc ggc acg gcc aac cgc tgg gac     720
Ile Val Asp Glu Leu Val Pro Tyr Ile Gly Thr Ala Asn Arg Trp Asp
225                 230                 235                 240 tac ctg ccg gtg ctg cgc tgg ttc gac gtg ttc ggc gtg agg aac aag     768
```

```
                Tyr Leu Pro Val Leu Arg Trp Phe Asp Val Phe Gly Val Arg Asn Lys
                                245                 250                 255 atc ctc gac gcc gtg ggc aga agg gac gcg ttc ctg ggg cgg ctc atc          816
Ile Leu Asp Ala Val Gly Arg Arg Asp Ala Phe Leu Gly Arg Leu Ile
            260                 265                 270 gac ggg gag cgg cgg agg ctg gac gct ggc gac gag agc gaa agt aag          864
Asp Gly Glu Arg Arg Arg Leu Asp Ala Gly Asp Glu Ser Glu Ser Lys
        275                 280                 285 agc atg att gcg gtg ctg ctc act ctg cag aag tcc gag cca gag gtc          912
Ser Met Ile Ala Val Leu Leu Thr Leu Gln Lys Ser Glu Pro Glu Val
    290                 295                 300 tac act gac act gtg atc act gct ctt tgc gcg aac cta ttc ggc gcc          960
Tyr Thr Asp Thr Val Ile Thr Ala Leu Cys Ala Asn Leu Phe Gly Ala
305                 310                 315                 320 gga acg gag acc acg tcc acc acg acg gaa tgg gcc atg tca ctg ctg         1008
Gly Thr Glu Thr Thr Ser Thr Thr Thr Glu Trp Ala Met Ser Leu Leu
                325                 330                 335 ctg aac cac cgg gag gcg ctc aag aag gcg cag gcc gag atc gac gcg         1056
Leu Asn His Arg Glu Ala Leu Lys Lys Ala Gln Ala Glu Ile Asp Ala
            340                 345                 350 gcg gtg ggc acc tcc cgc ctg gtg acc gcg gac gac gtg ccc cac ctc         1104
Ala Val Gly Thr Ser Arg Leu Val Thr Ala Asp Asp Val Pro His Leu
        355                 360                 365 acc tac ctg cag tgc atc gtc gac gag acg ctg cgc ctg cac ccg gcc         1152
Thr Tyr Leu Gln Cys Ile Val Asp Glu Thr Leu Arg Leu His Pro Ala
    370                 375                 380 gcg ccg ctg ctg ctg ccg cac gag tcc gcc gcg gac tgc acg gtc ggc         1200
Ala Pro Leu Leu Leu Pro His Glu Ser Ala Ala Asp Cys Thr Val Gly
385                 390                 395                 400 ggc tac gac gtg ccg cgc ggc acg atg ctg ctg gtc aac gtg cac gcg         1248
Gly Tyr Asp Val Pro Arg Gly Thr Met Leu Leu Val Asn Val His Ala
                405                 410                 415 gtc cac agg gac ccc gcg gtg tgg gag gac ccg gac agg ttc gtg ccg         1296
Val His Arg Asp Pro Ala Val Trp Glu Asp Pro Asp Arg Phe Val Pro
            420                 425                 430 gag cgg ttc gag ggc gcc ggc ggc aag gcc gag ggg cgc ctg ctg atg         1344
Glu Arg Phe Glu Gly Ala Gly Gly Lys Ala Glu Gly Arg Leu Leu Met
        435                 440                 445 ccg ttc ggg atg ggg cgg cgc aag tgc ccc ggg gag acg ctc gcg ctg         1392
Pro Phe Gly Met Gly Arg Arg Lys Cys Pro Gly Glu Thr Leu Ala Leu
    450                 455                 460 cgg acc gtc ggg ctg gtg ctc gcc acg ctg ctc cag tgc ttc gac tgg         1440
Arg Thr Val Gly Leu Val Leu Ala Thr Leu Leu Gln Cys Phe Asp Trp
465                 470                 475                 480 gac acg gtt gat gga gct cag gtt gac atg aag gct agc ggg ggc ctg         1488
Asp Thr Val Asp Gly Ala Gln Val Asp Met Lys Ala Ser Gly Gly Leu
                485                 490                 495 acc atg ccc cgg gcc gtc ccg ttg gag gcc atg tgc agg ccg cgt aca         1536
Thr Met Pro Arg Ala Val Pro Leu Glu Ala Met Cys Arg Pro Arg Thr
            500                 505                 510 gct atg cgt ggt gtt ctt aag agg ctc tga                                 1566
Ala Met Arg Gly Val Leu Lys Arg Leu *
        515                 520

<210> SEQ ID NO 20
<211> LENGTH: 521
<212> TYPE: PRT
<213> ORGANISM: Zea mays
<220> FEATURE:
<221> NAME/KEY: PEPTIDE
<222> LOCATION: (0)...(0)
```

<223> OTHER INFORMATION: BMS maize line Nsf1 peptide

<400> SEQUENCE: 20

```
Met Asp Lys Ala Tyr Ile Ala Ala Leu Ser Ala Ala Leu Phe Leu
 1               5                  10                  15

Leu His Tyr Leu Leu Gly Arg Arg Ala Gly Gly Glu Gly Lys Ala Lys
                 20                  25                  30

Ala Lys Gly Ser Arg Arg Leu Pro Pro Ser Pro Pro Ala Ile Pro
             35                  40                  45

Phe Leu Gly His Leu His Leu Val Lys Ala Pro Phe His Gly Ala Leu
 50                  55                  60

Ala Arg Leu Ala Ala Arg His Gly Pro Val Phe Ser Met Arg Leu Gly
 65                  70                  75                  80

Thr Arg Arg Ala Val Val Val Ser Ser Pro Asp Cys Ala Arg Glu Cys
                 85                  90                  95

Phe Thr Glu His Asp Val Asn Phe Ala Asn Arg Pro Leu Phe Pro Ser
                100                 105                 110

Met Arg Leu Ala Ser Phe Asp Gly Ala Met Leu Ser Val Ser Ser Tyr
                115                 120                 125

Gly Pro Tyr Trp Arg Asn Leu Arg Arg Val Ala Ala Val Gln Leu Leu
130                 135                 140

Ser Ala His Arg Val Gly Cys Met Ala Pro Ala Ile Glu Ala Gln Val
145                 150                 155                 160

Arg Ala Met Val Arg Arg Met Asp Arg Ala Ala Ala Gly Gly Gly
                165                 170                 175

Gly Val Ala Arg Val Gln Leu Lys Arg Leu Phe Glu Leu Ser Leu
            180                 185                 190

Ser Val Leu Met Glu Thr Ile Ala His Thr Lys Thr Ser Arg Ala Glu
                195                 200                 205

Ala Asp Ala Asp Ser Asp Met Ser Thr Glu Ala His Glu Phe Lys Gln
210                 215                 220

Ile Val Asp Glu Leu Val Pro Tyr Ile Gly Thr Ala Asn Arg Trp Asp
225                 230                 235                 240

Tyr Leu Pro Val Leu Arg Trp Phe Asp Val Phe Gly Val Arg Asn Lys
                245                 250                 255

Ile Leu Asp Ala Val Gly Arg Arg Asp Ala Phe Leu Gly Arg Leu Ile
                260                 265                 270

Asp Gly Glu Arg Arg Arg Leu Asp Ala Gly Asp Glu Ser Glu Ser Lys
            275                 280                 285

Ser Met Ile Ala Val Leu Leu Thr Leu Gln Lys Ser Glu Pro Glu Val
290                 295                 300

Tyr Thr Asp Thr Val Ile Thr Ala Leu Cys Ala Asn Leu Phe Gly Ala
305                 310                 315                 320

Gly Thr Glu Thr Thr Ser Thr Thr Thr Glu Trp Ala Met Ser Leu Leu
                325                 330                 335

Leu Asn His Arg Glu Ala Leu Lys Lys Ala Gln Ala Glu Ile Asp Ala
                340                 345                 350

Ala Val Gly Thr Ser Arg Leu Val Thr Ala Asp Val Pro His Leu
            355                 360                 365

Thr Tyr Leu Gln Cys Ile Val Asp Glu Thr Leu Arg Leu His Pro Ala
    370                 375                 380

Ala Pro Leu Leu Leu Pro His Glu Ser Ala Ala Asp Cys Thr Val Gly
385                 390                 395                 400
```

```
Gly Tyr Asp Val Pro Arg Gly Thr Met Leu Leu Val Asn Val His Ala
                405                 410                 415
Val His Arg Asp Pro Ala Val Trp Glu Asp Pro Asp Arg Phe Val Pro
            420                 425                 430
Glu Arg Phe Glu Gly Ala Gly Gly Lys Ala Glu Gly Arg Leu Leu Met
        435                 440                 445
Pro Phe Gly Met Gly Arg Arg Lys Cys Pro Gly Glu Thr Leu Ala Leu
    450                 455                 460
Arg Thr Val Gly Leu Val Leu Ala Thr Leu Leu Gln Cys Phe Asp Trp
465                 470                 475                 480
Asp Thr Val Asp Gly Ala Gln Val Asp Met Lys Ala Ser Gly Gly Leu
                485                 490                 495
Thr Met Pro Arg Ala Val Pro Leu Glu Ala Met Cys Arg Pro Arg Thr
            500                 505                 510
Ala Met Arg Gly Val Leu Lys Arg Leu
        515                 520

<210> SEQ ID NO 21
<211> LENGTH: 1566
<212> TYPE: DNA
<213> ORGANISM: Zea mays
<220> FEATURE:
<221> NAME/KEY: misc_feature
<222> LOCATION: (0)...(0)
<223> OTHER INFORMATION: F2 maize line ORF for Nsf1
<221> NAME/KEY: CDS
<222> LOCATION: (1)...(1566)

<400> SEQUENCE: 21 atg gat aag gcc tac atc gcc gcc ctc tcc gcc gcc gcc ctc ttc ttg      48
Met Asp Lys Ala Tyr Ile Ala Ala Leu Ser Ala Ala Ala Leu Phe Leu
1               5                  10                  15 ctc cac tac ctc ctg ggc cgc cgg gcc ggc ggc gag ggc aag gcc aag      96
Leu His Tyr Leu Leu Gly Arg Arg Ala Gly Gly Glu Gly Lys Ala Lys
            20                  25                  30 gcc aag ggc tcg cgg cgg cgg ctc ccg ccg agc cct ccg gcg atc ccg     144
Ala Lys Gly Ser Arg Arg Arg Leu Pro Pro Ser Pro Pro Ala Ile Pro
        35                  40                  45 ttc ctg ggc cac ctc cac ctc gtc aag gcc ccg ttc cac ggg gcg ctg     192
Phe Leu Gly His Leu His Leu Val Lys Ala Pro Phe His Gly Ala Leu
    50                  55                  60 gcc cgc ctc gcg gcg cgc cac ggc ccg gtg ttc tcc atg cgc ctg ggg     240
Ala Arg Leu Ala Ala Arg His Gly Pro Val Phe Ser Met Arg Leu Gly
65                  70                  75                  80 acc cgg cgc gcc gtg gtc gtg tcg tcg ccg gac tgc gcc agg gag tgc     288
Thr Arg Arg Ala Val Val Val Ser Ser Pro Asp Cys Ala Arg Glu Cys
                85                  90                  95 ttc acg gag cac gac gtg aac ttc gcg aac cgg ccg ctg ttc ccg tcg     336
Phe Thr Glu His Asp Val Asn Phe Ala Asn Arg Pro Leu Phe Pro Ser
            100                 105                 110 atg cgg ctg gcg tcc ttc gac ggc gcc atg ctc tcc gtg tcc agc tac     384
Met Arg Leu Ala Ser Phe Asp Gly Ala Met Leu Ser Val Ser Ser Tyr
        115                 120                 125 ggc ccg tac tgg cgc aac ctg cgc cgc gtc gcc gcc gtg cag ctc ctc     432
Gly Pro Tyr Trp Arg Asn Leu Arg Arg Val Ala Ala Val Gln Leu Leu
    130                 135                 140 tcc gcg cac cgc gtc ggg tgc atg gcc ccc gcc atc gaa gcg cag gtg     480
Ser Ala His Arg Val Gly Cys Met Ala Pro Ala Ile Glu Ala Gln Val
145                 150                 155                 160 cgc gcc atg gtg cgg agg atg gac cgc gcc gcc gcg gcc ggc ggc ggc     528
```

```
                Arg Ala Met Val Arg Met Asp Arg Ala Ala Ala Gly Gly Gly
                                165                 170                 175 ggc gtc gcg cgc gtc cag ctc aag cgg cgg ctg ttc gag ctc tcc ctc         576
Gly Val Ala Arg Val Gln Leu Lys Arg Arg Leu Phe Glu Leu Ser Leu
            180                 185                 190 agc gtg ctc atg gag acc atc gcg cac acc aag acg tcc cgc gcc gag         624
Ser Val Leu Met Glu Thr Ile Ala His Thr Lys Thr Ser Arg Ala Glu
            195                 200                 205 gcc gac gcc gac tcg gac atg tcg acc gag gcc cac gag ttc aag cag         672
Ala Asp Ala Asp Ser Asp Met Ser Thr Glu Ala His Glu Phe Lys Gln
            210                 215                 220 atc gtc gac gag ctc gtg ccg tac atc ggc acg gcc aac cgc tgg gac         720
Ile Val Asp Glu Leu Val Pro Tyr Ile Gly Thr Ala Asn Arg Trp Asp
225                 230                 235                 240 tac ctg ccg gtg ctg cgc tgg ttc gac gtg ttc ggc gtg agg aac aag         768
Tyr Leu Pro Val Leu Arg Trp Phe Asp Val Phe Gly Val Arg Asn Lys
                245                 250                 255 atc ctc gac gcc gtg ggc aca agg gac gcg ttc ctg ggg cgg ctc atc         816
Ile Leu Asp Ala Val Gly Thr Arg Asp Ala Phe Leu Gly Arg Leu Ile
            260                 265                 270 gac ggg gag cgg cgg agg ctg gac gct ggc gac gag agc gaa agt aag         864
Asp Gly Glu Arg Arg Arg Leu Asp Ala Gly Asp Glu Ser Glu Ser Lys
            275                 280                 285 agc atg att gcg gtg ctc ctc act ctg cag aag tcc gag cca gag gtc         912
Ser Met Ile Ala Val Leu Leu Thr Leu Gln Lys Ser Glu Pro Glu Val
            290                 295                 300 tac act gac act gtg atc act gct ctt tgc gcg aac cta ttc ggc gcc         960
Tyr Thr Asp Thr Val Ile Thr Ala Leu Cys Ala Asn Leu Phe Gly Ala
305                 310                 315                 320 gga acg gag acc acg tcc acg acg gaa tgg gcc atg tca ctg ctg            1008
Gly Thr Glu Thr Thr Ser Thr Thr Glu Trp Ala Met Ser Leu Leu
                325                 330                 335 ctg aac cac cgg gag gcg ctc aag aag gcg cag gcc gag atc gac gcg        1056
Leu Asn His Arg Glu Ala Leu Lys Lys Ala Gln Ala Glu Ile Asp Ala
            340                 345                 350 gcg gtg ggc acc tcc cgc ctg gtg acc gcg gac gac gtg ccc cac ctc        1104
Ala Val Gly Thr Ser Arg Leu Val Thr Ala Asp Asp Val Pro His Leu
            355                 360                 365 acc tac ctg cag tgc atc gtc gac gag acg ctg cgc ctg cac ccg gcc        1152
Thr Tyr Leu Gln Cys Ile Val Asp Glu Thr Leu Arg Leu His Pro Ala
            370                 375                 380 gcg ccg ctg ctg ctg ccg cac gag tcc gcc gcg gac tgc acg gtc ggc        1200
Ala Pro Leu Leu Leu Pro His Glu Ser Ala Ala Asp Cys Thr Val Gly
385                 390                 395                 400 ggc tac gac gtg ccg cgc ggc acg atg ctg ctg gtc aac gtg cac gcg        1248
Gly Tyr Asp Val Pro Arg Gly Thr Met Leu Leu Val Asn Val His Ala
                405                 410                 415 gtc cac agg gac ccc gcg gtg tgg gag gac ccg gac agg ttc gtg ccg        1296
Val His Arg Asp Pro Ala Val Trp Glu Asp Pro Asp Arg Phe Val Pro
            420                 425                 430 gag cgg ttc gag ggc gcc ggc ggc aag gcc gag ggg cgc ctg ctg atg        1344
Glu Arg Phe Glu Gly Ala Gly Gly Lys Ala Glu Gly Arg Leu Leu Met
            435                 440                 445 ccg ttc ggg atg ggg cgg cgc aag tgc ccc ggg gag acg ctc gcg ctg        1392
Pro Phe Gly Met Gly Arg Arg Lys Cys Pro Gly Glu Thr Leu Ala Leu
450                 455                 460 cgg acc gtc ggg ctg gtg ctc gcc acg ctg ctc cag tgc ttc gac tgg        1440
Arg Thr Val Gly Leu Val Leu Ala Thr Leu Leu Gln Cys Phe Asp Trp
465                 470                 475                 480
```

-continued

```
gac acg gtt gat gga gct cag gtt gac atg aag gct agc ggc ggg ctg    1488
Asp Thr Val Asp Gly Ala Gln Val Asp Met Lys Ala Ser Gly Gly Leu
            485                 490                 495 acc atg ccc cgg gcc gtc ccg ttg gag gcc atg tgc agg ccg cgt aca    1536
Thr Met Pro Arg Ala Val Pro Leu Glu Ala Met Cys Arg Pro Arg Thr
        500                 505                 510 gct atg cgt ggt gtt ctt aag agg ctc tga                            1566
Ala Met Arg Gly Val Leu Lys Arg Leu *
        515                 520
```

<210> SEQ ID NO 22
<211> LENGTH: 521
<212> TYPE: PRT
<213> ORGANISM: Zea mays
<220> FEATURE:
<221> NAME/KEY: PEPTIDE
<222> LOCATION: (0)...(0)
<223> OTHER INFORMATION: F2 maize line Nsf1 peptide

<400> SEQUENCE: 22

```
Met Asp Lys Ala Tyr Ile Ala Ala Leu Ser Ala Ala Ala Leu Phe Leu
 1               5                  10                  15

Leu His Tyr Leu Leu Gly Arg Arg Ala Gly Gly Glu Gly Lys Ala Lys
             20                  25                  30

Ala Lys Gly Ser Arg Arg Leu Pro Pro Ser Pro Pro Ala Ile Pro
         35                  40                  45

Phe Leu Gly His Leu His Leu Val Lys Ala Pro Phe His Gly Ala Leu
     50                  55                  60

Ala Arg Leu Ala Ala Arg His Gly Pro Val Phe Ser Met Arg Leu Gly
 65                  70                  75                  80

Thr Arg Arg Ala Val Val Val Ser Ser Pro Asp Cys Ala Arg Glu Cys
                 85                  90                  95

Phe Thr Glu His Asp Val Asn Phe Ala Asn Arg Pro Leu Phe Pro Ser
            100                 105                 110

Met Arg Leu Ala Ser Phe Asp Gly Ala Met Leu Ser Val Ser Ser Tyr
        115                 120                 125

Gly Pro Tyr Trp Arg Asn Leu Arg Arg Val Ala Ala Val Gln Leu Leu
    130                 135                 140

Ser Ala His Arg Val Gly Cys Met Ala Pro Ala Ile Glu Ala Gln Val
145                 150                 155                 160

Arg Ala Met Val Arg Arg Met Asp Arg Ala Ala Ala Gly Gly Gly
                165                 170                 175

Gly Val Ala Arg Val Gln Leu Lys Arg Arg Leu Phe Glu Leu Ser Leu
            180                 185                 190

Ser Val Leu Met Glu Thr Ile Ala His Thr Lys Thr Ser Arg Ala Glu
        195                 200                 205

Ala Asp Ala Asp Ser Asp Met Ser Thr Glu Ala His Glu Phe Lys Gln
    210                 215                 220

Ile Val Asp Glu Leu Val Pro Tyr Ile Gly Thr Ala Asn Arg Trp Asp
225                 230                 235                 240

Tyr Leu Pro Val Leu Arg Trp Phe Asp Val Phe Gly Val Arg Asn Lys
                245                 250                 255

Ile Leu Asp Ala Val Gly Thr Arg Asp Ala Phe Leu Gly Arg Leu Ile
            260                 265                 270

Asp Gly Glu Arg Arg Arg Leu Asp Ala Gly Asp Glu Ser Glu Ser Lys
        275                 280                 285

Ser Met Ile Ala Val Leu Leu Thr Leu Gln Lys Ser Glu Pro Glu Val
```

```
                    290                 295                 300
Tyr Thr Asp Thr Val Ile Thr Ala Leu Cys Ala Asn Leu Phe Gly Ala
305                 310                 315                 320

Gly Thr Glu Thr Thr Ser Thr Thr Thr Glu Trp Ala Met Ser Leu Leu
                325                 330                 335

Leu Asn His Arg Glu Ala Leu Lys Lys Ala Gln Ala Glu Ile Asp Ala
                340                 345                 350

Ala Val Gly Thr Ser Arg Leu Val Thr Ala Asp Asp Val Pro His Leu
                355                 360                 365

Thr Tyr Leu Gln Cys Ile Val Asp Glu Thr Leu Arg Leu His Pro Ala
370                 375                 380

Ala Pro Leu Leu Leu Pro His Glu Ser Ala Ala Asp Cys Thr Val Gly
385                 390                 395                 400

Gly Tyr Asp Val Pro Arg Gly Thr Met Leu Leu Val Asn Val His Ala
                405                 410                 415

Val His Arg Asp Pro Ala Val Trp Glu Asp Pro Asp Arg Phe Val Pro
                420                 425                 430

Glu Arg Phe Glu Gly Ala Gly Gly Lys Ala Glu Gly Arg Leu Leu Met
                435                 440                 445

Pro Phe Gly Met Gly Arg Arg Lys Cys Pro Gly Glu Thr Leu Ala Leu
                450                 455                 460

Arg Thr Val Gly Leu Val Leu Ala Thr Leu Leu Gln Cys Phe Asp Trp
465                 470                 475                 480

Asp Thr Val Asp Gly Ala Gln Val Asp Met Lys Ala Ser Gly Gly Leu
                485                 490                 495

Thr Met Pro Arg Ala Val Pro Leu Glu Ala Met Cys Arg Pro Arg Thr
                500                 505                 510

Ala Met Arg Gly Val Leu Lys Arg Leu
                515                 520

<210> SEQ ID NO 23
<211> LENGTH: 1952
<212> TYPE: DNA
<213> ORGANISM: Zea mays
<220> FEATURE:
<221> NAME/KEY: misc_feature
<222> LOCATION: (0)...(0)
<223> OTHER INFORMATION: GA209 maize line ORF for Nsf1
<221> NAME/KEY: CDS
<222> LOCATION: (1)...(1017)

<400> SEQUENCE: 23 atg gat aag gcc tac atc gcc gcc ctc tcc gcc gcc gcc ctc ttc ttg      48
Met Asp Lys Ala Tyr Ile Ala Ala Leu Ser Ala Ala Ala Leu Phe Leu
1               5                   10                  15 ctc cac tac ctc ctg ggc cgg cgg gcc ggc gtc gag ggc aag gcc aag      96
Leu His Tyr Leu Leu Gly Arg Arg Ala Gly Val Glu Gly Lys Ala Lys
            20                  25                  30 ggc tcg cgg cgg cgg ctc ccg ccg agc cct ccg gcg atc ccg ttc ctg     144
Gly Ser Arg Arg Arg Leu Pro Pro Ser Pro Pro Ala Ile Pro Phe Leu
        35                  40                  45 ggc cac ctc cac ctc gtc aag gcc ccg ttc cac ggg gcg ctg gcc cgc     192
Gly His Leu His Leu Val Lys Ala Pro Phe His Gly Ala Leu Ala Arg
    50                  55                  60 ctc gcg gcg cgc cac ggc ccg gtg ttc tcc atg cgc ctg ggg acc cgg     240
Leu Ala Ala Arg His Gly Pro Val Phe Ser Met Arg Leu Gly Thr Arg
65                  70                  75                  80 cgc gcc gtg gtc gtg tcg tcg ccg gac tgc gcc agg gag tgc ttc acg     288
```

-continued

| | | |
|---|---|---|
| Arg Ala Val Val Val Ser Ser Pro Asp Cys Ala Arg Glu Cys Phe Thr<br>                            85                            90                            95 | | |
| gag cac gac gtg aac ttc gcg aac cgg ccg ctg ttc ccg tcg atg cgg<br>Glu His Asp Val Asn Phe Ala Asn Arg Pro Leu Phe Pro Ser Met Arg<br>                       100                     105                     110 | 336 |
| ctg gcg tcc ttc gac ggc gcc atg ctc tcc gtg tcc agc tac ggc ccg<br>Leu Ala Ser Phe Asp Gly Ala Met Leu Ser Val Ser Ser Tyr Gly Pro<br>                       115                     120                     125 | 384 |
| tac tgg cgc aac ctg cgc cgc gtc gcc gcc gtg cag ctc ctc tcc gcg<br>Tyr Trp Arg Asn Leu Arg Arg Val Ala Ala Val Gln Leu Leu Ser Ala<br>               130                     135                     140 | 432 |
| cac cgc gtc ggg tgc atg gcc ccc gcc atc gaa gcg cag gtg cgc gcc<br>His Arg Val Gly Cys Met Ala Pro Ala Ile Glu Ala Gln Val Arg Ala<br>145                     150                     155                     160 | 480 |
| atg gtg cgg agg atg gac cgc gcc gcc gcg gcc ggc ggc ggc ggc gtc<br>Met Val Arg Arg Met Asp Arg Ala Ala Ala Ala Gly Gly Gly Gly Val<br>                     165                     170                     175 | 528 |
| gcg cgc gtc cag ctc aag cgg cgg ctg ttc gag ctc tcc ctc agc gtg<br>Ala Arg Val Gln Leu Lys Arg Arg Leu Phe Glu Leu Ser Leu Ser Val<br>               180                     185                     190 | 576 |
| ctc atg gaa acc atc gcg cac acc aag acg tcc cgc gcc gag gcc gac<br>Leu Met Glu Thr Ile Ala His Thr Lys Thr Ser Arg Ala Glu Ala Asp<br>         195                     200                     205 | 624 |
| gcc aac tcg gac atg tcg acc gag gcc cac gag ttc aag caa atc gtc<br>Ala Asn Ser Asp Met Ser Thr Glu Ala His Glu Phe Lys Gln Ile Val<br>210                     215                     220 | 672 |
| aac gag ctc gtg ccg tac atc ggc acg gcc aac tgc tgg gac tac ctg<br>Asn Glu Leu Val Pro Tyr Ile Gly Thr Ala Asn Cys Trp Asp Tyr Leu<br>225                     230                     235                     240 | 720 |
| ccg gtg ctg cgc tgg ttc gac gtg ttc ggc gtg agg aac aag atc ctc<br>Pro Val Leu Arg Trp Phe Asp Val Phe Gly Val Arg Asn Lys Ile Leu<br>               245                     250                     255 | 768 |
| gac gcc gtg ggc aga agg gac gcg ttc cta ggg cgg ctc atc gac ggg<br>Asp Ala Val Gly Arg Arg Asp Ala Phe Leu Gly Arg Leu Ile Asp Gly<br>                     260                     265                     270 | 816 |
| gag cgg cgc agg ctg gac gct ggc gac gag agc gaa agt aag agc atg<br>Glu Arg Arg Arg Leu Asp Ala Gly Asp Glu Ser Glu Ser Lys Ser Met<br>         275                     280                     285 | 864 |
| att gcg gtg ctg ctc act ctg cag aag tcc gag cca gag gtc tac act<br>Ile Ala Val Leu Leu Thr Leu Gln Lys Ser Glu Pro Glu Val Tyr Thr<br>290                     295                     300 | 912 |
| gac act gtg atc act gct ctg tta gca act ctg tcg gct agg gca cga<br>Asp Thr Val Ile Thr Ala Leu Leu Ala Thr Leu Ser Ala Arg Ala Arg<br>305                     310                     315                     320 | 960 |
| aca aca gtc gct aga gat gta gag aac gct aga ggt gtg gag aac agg<br>Thr Thr Val Ala Arg Asp Val Glu Asn Ala Arg Gly Val Glu Asn Arg<br>                     325                     330                     335 | 1008 |
| aaa ata tga cgtggggaag aagaacaagc cgccagagaa cgcagaacct<br>Lys Ile  * | 1057 |
| gatgtttgtt attttctcga tagcccttc cctcggccac caatccctat atatggtttc | 1117 |
| tggtatgcca ttcttacagt atggaataca cggcccaatt agcagtccag tctatttcgt | 1177 |
| atttgggctc ctttgacgct cctcggcttc tcgccttagc tgctcacatc ggctcctttc | 1237 |
| ttctctcgtc gtccttgtgc tcactcggat gagggatgtt gacattttta gtgaaacact | 1297 |
| acatttttag tccagtctat ttcgtatttg cgcgaaccta ttcggcgccg aacggagac | 1357 |
| cacgtccacc acgacggaat gggccatgtc actgctgctg aaccaccggg aggcgctcaa | 1417 |
| gaaggcgcag gccgagatcg acgcggcggt gggcacctcc cgcctggtga ccgcggacga | 1477 |

-continued

```
cgtgccccac tcacctacc tgcagtgcat cgtcgacgag acgctgcgcc tgcacccggc    1537
cgcgccgctg ctgctgccgc acgagtccgc cgcggactgc acggtcggcg gctacgacgt    1597
gccgcgcggc acgatgctgc tggtcaacgt gcacgcggtc cacagggacc ccgcggtgtg    1657
ggaggacccg gacaggttcg tgccggagcg gttcgagggc gccggcggca aggccgaggg    1717
gcgcctgctg atgccgttcg ggatggggcg gcgcaagtgc cccggggaga cgctcgcgct    1777
gcggaccgtc gggctggtgc tcgccacgct gctccagtgc ttcgactggg acacggttga    1837
tggagctcag gttgacatga aggctagcgg cgggctgacc atgccccggg ccgtcccgtt    1897
ggaggccatg tgcaggccgc gtacagctat gcgtggtgtt cttaagaggc tctga          1952
```

<210> SEQ ID NO 24
<211> LENGTH: 338
<212> TYPE: PRT
<213> ORGANISM: Zea mays
<220> FEATURE:
<221> NAME/KEY: PEPTIDE
<222> LOCATION: (0)...(0)
<223> OTHER INFORMATION: GA209 maize line Nsf1 peptide

<400> SEQUENCE: 24

```
Met Asp Lys Ala Tyr Ile Ala Ala Leu Ser Ala Ala Ala Leu Phe Leu
 1               5                  10                  15

Leu His Tyr Leu Leu Gly Arg Arg Ala Gly Val Glu Gly Lys Ala Lys
             20                  25                  30

Gly Ser Arg Arg Arg Leu Pro Pro Ser Pro Pro Ala Ile Pro Phe Leu
         35                  40                  45

Gly His Leu His Leu Val Lys Ala Pro Phe His Gly Ala Leu Ala Arg
     50                  55                  60

Leu Ala Ala Arg His Gly Pro Val Phe Ser Met Arg Leu Gly Thr Arg
 65                  70                  75                  80

Arg Ala Val Val Val Ser Ser Pro Asp Cys Ala Arg Glu Cys Phe Thr
                 85                  90                  95

Glu His Asp Val Asn Phe Ala Asn Arg Pro Leu Phe Pro Ser Met Arg
            100                 105                 110

Leu Ala Ser Phe Asp Gly Ala Met Leu Ser Val Ser Ser Tyr Gly Pro
        115                 120                 125

Tyr Trp Arg Asn Leu Arg Arg Val Ala Ala Val Gln Leu Leu Ser Ala
    130                 135                 140

His Arg Val Gly Cys Met Ala Pro Ala Ile Glu Ala Gln Val Arg Ala
145                 150                 155                 160

Met Val Arg Arg Met Asp Arg Ala Ala Ala Gly Gly Gly Gly Val
                165                 170                 175

Ala Arg Val Gln Leu Lys Arg Arg Leu Phe Glu Leu Ser Leu Ser Val
            180                 185                 190

Leu Met Glu Thr Ile Ala His Thr Lys Thr Ser Arg Ala Glu Ala Asp
        195                 200                 205

Ala Asn Ser Asp Met Ser Thr Glu Ala His Glu Phe Lys Gln Ile Val
    210                 215                 220

Asn Glu Leu Val Pro Tyr Ile Gly Thr Ala Asn Cys Trp Asp Tyr Leu
225                 230                 235                 240

Pro Val Leu Arg Trp Phe Asp Val Phe Gly Val Arg Asn Lys Ile Leu
                245                 250                 255

Asp Ala Val Gly Arg Arg Asp Ala Phe Leu Gly Arg Leu Ile Asp Gly
            260                 265                 270
```

```
Glu Arg Arg Arg Leu Asp Ala Gly Asp Glu Ser Glu Ser Lys Ser Met
            275                 280                 285

Ile Ala Val Leu Leu Thr Leu Gln Lys Ser Glu Pro Glu Val Tyr Thr
            290                 295                 300

Asp Thr Val Ile Thr Ala Leu Leu Ala Thr Leu Ser Ala Arg Ala Arg
305             310                 315                 320

Thr Thr Val Ala Arg Asp Val Glu Asn Ala Arg Gly Val Glu Asn Arg
            325                 330                 335

Lys Ile

<210> SEQ ID NO 25
<211> LENGTH: 1932
<212> TYPE: DNA
<213> ORGANISM: Zea mays
<220> FEATURE:
<221> NAME/KEY: misc_feature
<222> LOCATION: (0)...(0)
<223> OTHER INFORMATION: W703A maize line ORF for Nsf1
<221> NAME/KEY: CDS
<222> LOCATION: (1)...(843)

<400> SEQUENCE: 25
```

| | | | | | | | | | | | | | | | | |
|---|---|---|---|---|---|---|---|---|---|---|---|---|---|---|---|---|
| atg | gat | aag | gcc | tac | atc | gcc | gcc | ctc | tcc | gcc | gcc | gcc | ctc | ttc | ttg | 48 |
| Met | Asp | Lys | Ala | Tyr | Ile | Ala | Ala | Leu | Ser | Ala | Ala | Ala | Leu | Phe | Leu | |
| 1 | | | | 5 | | | | | 10 | | | | | 15 | | |
| ctc | cac | tac | ctc | ctg | ggc | cgg | cgg | gcc | ggc | gtc | gag | ggc | aag | gcc | aag | 96 |
| Leu | His | Tyr | Leu | Leu | Gly | Arg | Arg | Ala | Gly | Val | Glu | Gly | Lys | Ala | Lys | |
| | | | 20 | | | | | 25 | | | | | 30 | | | |
| agc | tcg | cgg | cgg | cgg | ctc | ccg | ccg | agc | cct | ccg | gcg | atc | ccg | ttc | ctg | 144 |
| Ser | Ser | Arg | Arg | Arg | Leu | Pro | Pro | Ser | Pro | Pro | Ala | Ile | Pro | Phe | Leu | |
| | | 35 | | | | | 40 | | | | | 45 | | | | |
| ggc | cac | ctc | cac | ctc | gtc | aag | gcc | ccg | ttc | cac | gcg | gcg | ctg | gcc | cgc | 192 |
| Gly | His | Leu | His | Leu | Val | Lys | Ala | Pro | Phe | His | Ala | Ala | Leu | Ala | Arg | |
| | 50 | | | | | 55 | | | | | 60 | | | | | |
| ctc | gcg | gcg | cgc | cac | ggc | ccg | gtg | ttc | tcc | atg | cgc | ctg | ggg | acc | cgc | 240 |
| Leu | Ala | Ala | Arg | His | Gly | Pro | Val | Phe | Ser | Met | Arg | Leu | Gly | Thr | Arg | |
| 65 | | | | | 70 | | | | | 75 | | | | | 80 | |
| cgc | gcc | gtg | gtc | gtg | tcg | tcg | ccg | gac | tgc | gcc | agg | gag | tgc | ttc | acg | 288 |
| Arg | Ala | Val | Val | Val | Ser | Ser | Pro | Asp | Cys | Ala | Arg | Glu | Cys | Phe | Thr | |
| | | | | 85 | | | | | 90 | | | | | 95 | | |
| gag | cac | gac | gtg | aac | ttc | gcg | aac | cgg | ccg | ctg | ttc | ccg | tcg | atg | cgg | 336 |
| Glu | His | Asp | Val | Asn | Phe | Ala | Asn | Arg | Pro | Leu | Phe | Pro | Ser | Met | Arg | |
| | | | 100 | | | | | 105 | | | | | 110 | | | |
| ctg | gcg | tcc | ttc | gac | ggc | gcc | atg | ctc | tcc | gtg | tcc | agc | tac | ggc | ccg | 384 |
| Leu | Ala | Ser | Phe | Asp | Gly | Ala | Met | Leu | Ser | Val | Ser | Ser | Tyr | Gly | Pro | |
| | | 115 | | | | | 120 | | | | | 125 | | | | |
| tac | tgg | cgc | aac | ctg | cgc | cgc | gtc | gcc | gcc | gtg | cag | ctc | ctc | tcc | gcg | 432 |
| Tyr | Trp | Arg | Asn | Leu | Arg | Arg | Val | Ala | Ala | Val | Gln | Leu | Leu | Ser | Ala | |
| | 130 | | | | | 135 | | | | | 140 | | | | | |
| cac | cgc | gtc | gcg | tgc | atg | gtc | ccc | gcc | atc | gaa | gcg | cag | gtg | cgc | gcc | 480 |
| His | Arg | Val | Ala | Cys | Met | Val | Pro | Ala | Ile | Glu | Ala | Gln | Val | Arg | Ala | |
| 145 | | | | | 150 | | | | | 155 | | | | | 160 | |
| atg | gtg | cgg | agg | atg | gac | cgc | gcc | gcc | gcg | gcc | ggc | ggc | gcg | cgt | cgc | 528 |
| Met | Val | Arg | Arg | Met | Asp | Arg | Ala | Ala | Ala | Ala | Gly | Gly | Ala | Arg | Arg | |
| | | | | 165 | | | | | 170 | | | | | 175 | | |
| gcg | cgt | cca | gct | caa | gcg | gcg | gct | gtt | cga | gct | ctc | cct | cag | cgt | gct | 576 |
| Ala | Arg | Pro | Ala | Gln | Ala | Ala | Ala | Val | Arg | Ala | Leu | Pro | Gln | Arg | Ala | |
| | | | 180 | | | | | 185 | | | | | 190 | | | |
| cat | gga | aac | cat | cgc | gca | cac | caa | gac | gtc | ccg | cgc | caa | ctc | gaa | yat | 624 |
| His | Gly | Asn | His | Arg | Ala | His | Gln | Asp | Val | Pro | Arg | Gln | Leu | Glu | Xaa | |

-continued

```
            195                 200                 205
gtc gac cga ggc cca cga gtt caa gca rrt cgt caa cga gct cgt gcc      672
Val Asp Arg Gly Pro Arg Val Gln Ala Xaa Arg Gln Arg Ala Arg Ala
        210                 215                 220 gta cat cgg cgc ggc caa ccg ctg gga cta cct gcc ggt gct gcg ctg      720
Val His Arg Arg Gly Gln Pro Leu Gly Leu Pro Ala Gly Ala Ala Leu
225                 230                 235                 240 gtt cga cgt gtt cgg cgt gag gaa caa gat cct cga cgc cgt ggg cag      768
Val Arg Arg Val Arg Arg Glu Glu Gln Asp Pro Arg Arg Arg Gly Gln
                245                 250                 255 aag gga cgc gtt cct gag gcg gct cat cga cgg gga gcg gcg gag gct      816
Lys Gly Arg Val Pro Glu Ala Ala His Arg Arg Gly Ala Ala Glu Ala
            260                 265                 270 gga cgc tgg cga cga cag cga aag taa gagcatgatt gcggtgctgc            863
Gly Arg Trp Arg Arg Gln Arg Lys  *
        275                 280 tcactctgca gaagtccgag ccagaggtct acactgacac tgtgatcact gctctgttag    923
caactctgtc ggctagrgca cgaacaacag tcgctagaga tgtagagaac gctagaggtg    983
tggagaacag gaaatatga cgtggggaag aagaacaagc cgccagagaa cgcagaacct    1043
gatgtttgtt attttctcga tagccccttc cctcggccac caatccctat atatggtttc    1103
tggtatgcca ttcwtacagt atggaataca cggccyaatt agcagtccag tctatttcgt    1163
atttgggctc ctttgacgct cctcggcttc tcgccttagc tgctcacatc ggctcctttc    1223
ttctctcgtc gtccttgtgc tcactcggat gagggatgtt gacatttta gtgaaacatt    1283 acattttag tccagtctat ttcgtatttg cgcgaaccta ttcggcgccg gaacggagac    1343
cacgtccacc acgacggaat gggccatgtc gctgctgctg aaccaccggg aggcgctcaa    1403
gaaggcgcag gccgagatcg acgcggcggt gggcacctcc cgcctggtga ccgcggacga    1463
cgtgccccac ctcacctacc tgcagtgcat cgtcgacgag acgctgcgcc tgcaccccgc    1523
cgcgccgctg ctgctgccgc acgagtccgc cgcggactgc acggtcggcg gctacgacgt    1583
gccgcgcggc acgatgctgc tggtcaacgt gcacgcggtc cacagggacc ccgcggtgtg    1643
ggacgacccg gacaggttcg tgccggagcg gttcgagggc ggcaaggccg aggggcgcct    1703
gctgatgccg ttcgggatgg ggcggcgcaa gtgccccggg gagacgctcg cgctgcggac    1763
cgtcgggctg gtgctcggca cgctgctcca gtgcttcgac tgggacacgg ttgatggagc    1823
tcaggttgac atgaaggcta gcggcgggct gaccatgccc cgggccgtcc cgttggaggc    1883
catgtgcagg ccgcgtacag ctatgcgtga tgttcttaag aggctctga            1932
```

<210> SEQ ID NO 26
<211> LENGTH: 280
<212> TYPE: PRT
<213> ORGANISM: Zea mays
<220> FEATURE:
<221> NAME/KEY: PEPTIDE
<222> LOCATION: (0)...(0)
<223> OTHER INFORMATION: W703A maize line Nsf1 peptide
<221> NAME/KEY: VARIANT
<222> LOCATION: 208, 218
<223> OTHER INFORMATION: Xaa = Any Amino Acid

<400> SEQUENCE: 26

Met Asp Lys Ala Tyr Ile Ala Ala Leu Ser Ala Ala Leu Phe Leu
 1               5                  10                  15

Leu His Tyr Leu Leu Gly Arg Arg Ala Gly Val Glu Gly Lys Ala Lys
            20                  25                  30

-continued

```
Ser Ser Arg Arg Arg Leu Pro Pro Ser Pro Pro Ala Ile Pro Phe Leu
        35                  40                  45

Gly His Leu His Leu Val Lys Ala Pro Phe His Ala Ala Leu Ala Arg
    50                  55                  60

Leu Ala Ala Arg His Gly Pro Val Phe Ser Met Arg Leu Gly Thr Arg
65                  70                  75                  80

Arg Ala Val Val Val Ser Ser Pro Asp Cys Ala Arg Glu Cys Phe Thr
                85                  90                  95

Glu His Asp Val Asn Phe Ala Asn Arg Pro Leu Phe Pro Ser Met Arg
                100                 105                 110

Leu Ala Ser Phe Asp Gly Ala Met Leu Ser Val Ser Ser Tyr Gly Pro
            115                 120                 125

Tyr Trp Arg Asn Leu Arg Arg Val Ala Ala Val Gln Leu Leu Ser Ala
        130                 135                 140

His Arg Val Ala Cys Met Val Pro Ala Ile Glu Ala Gln Val Arg Ala
145                 150                 155                 160

Met Val Arg Arg Met Asp Arg Ala Ala Ala Ala Gly Gly Ala Arg Arg
                165                 170                 175

Ala Arg Pro Ala Gln Ala Ala Ala Val Arg Ala Leu Pro Gln Arg Ala
                180                 185                 190

His Gly Asn His Arg Ala His Gln Asp Val Pro Arg Gln Leu Glu Xaa
            195                 200                 205

Val Asp Arg Gly Pro Arg Val Gln Ala Xaa Arg Gln Arg Ala Arg Ala
        210                 215                 220

Val His Arg Arg Gly Gln Pro Leu Gly Leu Pro Ala Gly Ala Ala Leu
225                 230                 235                 240

Val Arg Arg Val Arg Arg Glu Glu Gln Asp Pro Arg Arg Arg Gly Gln
                245                 250                 255

Lys Gly Arg Val Pro Glu Ala Ala His Arg Arg Gly Ala Ala Glu Ala
                260                 265                 270

Gly Arg Trp Arg Arg Gln Arg Lys
        275                 280
```